(12) United States Patent
Tanuma et al.

(10) Patent No.: US 7,660,677 B2
(45) Date of Patent: Feb. 9, 2010

(54) METHOD OF DESIGNING PHYSIOLOGICALLY ACTIVE PEPTIDE AND USE THEREOF

(75) Inventors: Sei-ichi Tanuma, 2-21-8-707, Bessho, Hachioji-shi, Tokyo 192-0363 (JP); Atsushi Yoshimori, Noda (JP)

(73) Assignee: Sei-ichi Tanuma, Hachioji (JP)

( * ) Notice: Subject to any disclaimer, the term of this patent is extended or adjusted under 35 U.S.C. 154(b) by 666 days.

(21) Appl. No.: 10/526,406

(22) PCT Filed: Sep. 3, 2003

(86) PCT No.: PCT/JP03/11237

§ 371 (c)(1),
(2), (4) Date: Apr. 14, 2006

(87) PCT Pub. No.: WO2004/022737

PCT Pub. Date: Mar. 18, 2004

(65) Prior Publication Data

US 2006/0217891 A1    Sep. 28, 2006

(30) Foreign Application Priority Data

Sep. 3, 2002    (JP) .............................. 2002-258305

(51) Int. Cl.
  *G06F 19/00*    (2006.01)
  *G06F 15/00*    (2006.01)
  *G11C 17/00*    (2006.01)
(52) U.S. Cl. ................................ 702/27; 700/1; 365/94
(58) Field of Classification Search ........................ None
  See application file for complete search history.

(56) References Cited

U.S. PATENT DOCUMENTS 5,081,584 A    1/1992    Omichinski et al.

6,226,603 B1    5/2001    Freire et al.

FOREIGN PATENT DOCUMENTS

EP    0 633 534 A1    1/1995
EP    0 790 567 A1    8/1997

OTHER PUBLICATIONS

Blalock et al., *Biochemical and Biophysical Research Communications*, 121(1): 203-207 (May 31, 1984).
Campbell et al., *Microbiol. Immuno.*, 46(3): 211-215 (2002).
Fassina et al., *Archives of Biochemistry and Biophysics*, 296(1): 137-143 (Jul. 1992).
Gallet et al., *J. Mol. Biol.*, 302: 917-926 (2000).
Göbel et al., *Proteins*, 18(4): 309-317 (1994).
Morris et al., *Journal of Computational Chemistry*, 19(14): 1639-1662 (1998).
Ohtaki et al., *Nature*, 411: 613-617 (May 31, 2001).
Root-Bernstein, *J. Theor. Biol*, 94: 855-894 (1982).
Tomii et al., *Protein Engineering*, 9(1): 27-36 (1996).
Zhao et al., *The Journal of Immunology*, 167: 2130-2141 (2001).
Lamb et al., *Proteins: Structure, Function, and Genetics*, 42: 296-318 (2001).
Zhang et al., *Proc. Natl. Acad. Sci.*, 99(10): 6579-6584 (May 14, 2002).

*Primary Examiner*—John S Brusca
(74) *Attorney, Agent, or Firm*—Leydig, Voit & Mayer, Ltd.

(57) ABSTRACT

The present invention provides a means of economically, quickly and efficiently designing a physiologically active peptide to a target protein. Specifically, the present invention provides a method of designing a physiologically active peptide characterized in that, to design a physiologically active peptide capable of binding to a target site comprising a consecutive or non-consecutive amino acid sequence in a target protein, a computerized processing is carried out for extracting a preferable amino acid sequence by calculating intermolecular energy etc.; an apparatus therefor; a program for executing the above-described processing by a computer; and a computer-readable recording medium containing the program.

14 Claims, 27 Drawing Sheets

Fig. 14B

| AA | P4 | P3 | P2 |
|---|---|---|---|
| A | 70.83 | 80.00 | 47.06 |
| R | 64.29 | 56.25 | 42.11 |
| N | 78.95 | 73.68 | 76.00 |
| D | 100.00 | 66.67 | 82.61 |
| C | 61.11 | 50.00 | 65.52 |
| Q | 92.31 | 78.57 | 50.00 |
| E | 66.67 | 85.71 | 92.86 |
| G | 43.75 | 55.56 | 42.11 |
| H | 31.82 | 20.00 | 38.89 |
| I | 71.43 | 59.09 | 94.44 |
| L | 76.19 | 75.00 | 73.33 |
| K | 68.18 | 50.00 | 36.84 |
| M | 73.91 | 75.00 | 80.00 |
| F | 25.00 | 55.56 | 68.42 |
| P | 100.00 | 75.00 | 81.25 |
| S | 71.43 | 57.14 | 41.18 |
| T | 83.33 | 73.91 | 56.25 |
| W | 16.67 | 62.50 | 52.63 |
| Y | 16.67 | 50.00 | 75.00 |
| V | 100.00 | 71.43 | 100.00 |

PSS

Fig. 14C

| AA | P4 | P3 | P2 |
|---|---|---|---|
| A | -3.88 | -4.21 | -3.02 |
| R | -3.64 | -3.35 | -2.84 |
| N | -4.17 | -3.98 | -4.06 |
| D | -4.93 | -3.73 | -4.30 |
| C | -3.53 | -3.13 | -3.69 |
| Q | -4.65 | -4.16 | -3.13 |
| E | -3.73 | -4.42 | -4.67 |
| G | -2.90 | -3.33 | -2.84 |
| H | -2.47 | -2.04 | -2.73 |
| I | -3.90 | -3.45 | -4.73 |
| L | -4.07 | -4.03 | -3.97 |
| K | -3.78 | -3.13 | -2.65 |
| M | -3.99 | -4.03 | -4.21 |
| F | -2.22 | -3.33 | -3.79 |
| P | -4.93 | -4.03 | -4.25 |
| S | -3.90 | -3.38 | -2.81 |
| T | -4.33 | -3.99 | -3.35 |
| W | -1.92 | -3.58 | -3.22 |
| Y | -1.92 | -3.13 | -4.03 |
| V | -4.93 | -3.90 | -4.93 |

PSG

Fig. 15B

| AA | P4 | P3 | P2 |
|---|---|---|---|
| A | 28.57 | 41.67 | 38.46 |
| R | 0.00 | 0.00 | 8.00 |
| N | 50.00 | 30.00 | 27.78 |
| D | 80.95 | 45.00 | 29.41 |
| C | 53.85 | 14.29 | 27.27 |
| Q | 42.86 | 27.27 | 26.32 |
| E | 55.56 | 70.00 | 32.00 |
| G | 11.11 | 33.33 | 11.76 |
| H | 0.00 | 0.00 | 5.88 |
| I | 22.22 | 20.00 | 42.86 |
| L | 50.00 | 33.33 | 41.18 |
| K | 0.00 | 16.67 | 16.67 |
| M | 33.33 | 38.89 | 33.33 |
| F | 4.35 | 71.43 | 33.33 |
| P | 33.33 | 0.00 | 55.56 |
| S | 26.09 | 23.08 | 42.86 |
| T | 25.00 | 10.00 | 28.57 |
| W | 0.00 | 40.91 | 21.05 |
| Y | 4.76 | 21.05 | 26.67 |
| V | 39.13 | 26.09 | 37.50 |

PSS

Fig. 15C

| AA | P4 | P3 | P2 |
|---|---|---|---|
| A | -3.29 | -3.72 | -3.62 |
| R | -2.35 | -2.35 | -2.61 |
| N | -4.00 | -3.34 | -3.27 |
| D | -5.03 | -3.84 | -3.32 |
| C | -4.13 | -2.82 | -3.25 |
| Q | -3.76 | -3.25 | -3.22 |
| E | -4.18 | -4.66 | -3.40 |
| G | -2.71 | -3.45 | -2.73 |
| H | -2.35 | -2.35 | -2.54 |
| I | -3.08 | -3.01 | -3.76 |
| L | -4.00 | -3.45 | -3.71 |
| K | -2.35 | -2.90 | -2.90 |
| M | -3.45 | -3.63 | -3.45 |
| F | -2.49 | -4.71 | -3.45 |
| P | -3.45 | -2.35 | -4.18 |
| S | -3.21 | -3.11 | -3.76 |
| T | -3.17 | -2.68 | -3.29 |
| W | -2.35 | -3.70 | -3.04 |
| Y | -2.50 | -3.04 | -3.23 |
| V | -3.64 | -3.21 | -3.59 |

PSG

Fig. 16B

| AA | P4 | P3 | P2 |
|---|---|---|---|
| A | 47.83 | 23.53 | 52.94 |
| R | 12.50 | 4.76 | 15.38 |
| N | 25.00 | 54.55 | 64.71 |
| D | 55.00 | 85.71 | 52.63 |
| C | 15.00 | 27.78 | 45.45 |
| Q | 47.62 | 88.89 | 31.58 |
| E | 75.00 | 83.33 | 52.38 |
| G | 25.93 | 46.15 | 29.41 |
| H | 30.43 | 6.67 | 16.00 |
| I | 60.00 | 41.67 | 50.00 |
| L | 61.11 | 72.22 | 50.00 |
| K | 58.82 | 6.25 | 13.33 |
| M | 50.00 | 58.82 | 25.93 |
| F | 68.75 | 37.04 | 24.00 |
| P | 68.75 | 23.53 | 84.62 |
| S | 0.00 | 45.45 | 55.00 |
| T | 13.33 | 50.00 | 55.56 |
| W | 25.00 | 22.22 | 61.11 |
| Y | 25.00 | 46.15 | 7.14 |
| V | 53.33 | 45.45 | 68.42 |

PSS

Fig. 16C

| AA | P4 | P3 | P2 |
|---|---|---|---|
| A | -3.72 | -3.17 | -3.84 |
| R | -2.93 | -2.75 | -2.99 |
| N | -3.21 | -3.87 | -4.10 |
| D | -3.88 | -4.57 | -3.83 |
| C | -2.98 | -3.27 | -3.67 |
| Q | -3.72 | -4.64 | -3.35 |
| E | -4.33 | -4.52 | -3.82 |
| G | -3.23 | -3.68 | -3.31 |
| H | -3.33 | -2.79 | -3.00 |
| I | -3.99 | -3.58 | -3.77 |
| L | -4.02 | -4.27 | -3.77 |
| K | -3.97 | -2.78 | -2.94 |
| M | -3.77 | -3.97 | -3.23 |
| F | -4.19 | -3.48 | -3.18 |
| P | -4.19 | -3.17 | -4.55 |
| S | -2.64 | -3.67 | -3.88 |
| T | -2.94 | -3.77 | -3.89 |
| W | -3.21 | -3.14 | -4.02 |
| Y | -3.21 | -3.68 | -2.80 |
| V | -3.84 | -3.67 | -4.18 |

PSG

Fig. 17B

| AA | P4 | P3 | P2 |
|---|---|---|---|
| A | 62.50 | 57.14 | 50.00 |
| R | 45.00 | 36.00 | 57.89 |
| N | 73.91 | 62.50 | 53.85 |
| D | 88.24 | 82.35 | 68.18 |
| C | 30.77 | 55.56 | 23.53 |
| Q | 61.54 | 85.71 | 42.11 |
| E | 53.33 | 88.89 | 94.44 |
| G | 38.46 | 71.43 | 21.05 |
| H | 64.29 | 22.73 | 38.10 |
| I | 82.35 | 81.82 | 56.25 |
| L | 76.92 | 80.00 | 66.67 |
| K | 57.14 | 28.57 | 71.43 |
| M | 57.89 | 61.54 | 55.00 |
| F | 63.16 | 72.22 | 90.00 |
| P | 76.47 | 33.33 | 82.61 |
| S | 31.25 | 59.26 | 23.08 |
| T | 43.75 | 66.67 | 33.33 |
| W | 33.33 | 76.47 | 88.89 |
| Y | 36.84 | 26.32 | 87.50 |
| V | 83.33 | 66.67 | 50.00 |

PSS

Fig. 17C

| AA | P4 | P3 | P2 |
|---|---|---|---|
| A | -3.92 | -3.80 | -3.63 |
| R | -3.51 | -3.30 | -3.81 |
| N | -4.19 | -3.92 | -3.72 |
| D | -4.53 | -4.39 | -4.06 |
| C | -3.17 | -3.76 | -3.00 |
| Q | -3.90 | -4.47 | -3.44 |
| E | -3.71 | -4.55 | -4.68 |
| G | -3.36 | -4.13 | -2.95 |
| H | -3.97 | -2.98 | -3.35 |
| I | -4.39 | -4.38 | -3.78 |
| L | -4.26 | -4.34 | -4.02 |
| K | -3.80 | -3.12 | -4.13 |
| M | -3.81 | -3.90 | -3.75 |
| F | -3.94 | -4.15 | -4.57 |
| P | -4.25 | -3.23 | -4.40 |
| S | -3.19 | -3.85 | -2.99 |
| T | -3.48 | -4.02 | -3.23 |
| W | -3.23 | -4.25 | -4.55 |
| Y | -3.32 | -3.07 | -4.51 |
| V | -4.41 | -4.02 | -3.63 |

PSG

US 7,660,677 B2

METHOD OF DESIGNING PHYSIOLOGICALLY ACTIVE PEPTIDE AND USE THEREOF

TECHNICAL FIELD

The present invention relates to a method of developing a valuable peptide pharmaceutical. In particular, the present invention relates to a method of designing a physiologically active peptide capable of binding to a target site comprising an optionally chosen consecutive or non-consecutive amino acid sequence on a protein; an apparatus therefor; a program for executing the above-described method by a computer; and a computer-readable recording medium containing the program.

BACKGROUND ART

Various biosignals (neurotransmitters, hormones, cytokines) generated from extracellular signal transduction systems networked in the body (nervous system, endocrine system, immune system) are received and transmitted by intracellular signal transduction systems in target cells, resulting in appropriate responses. Here, the majority of biosignals are transmitted by protein-to-protein interactions. For example, various protein-to-protein interactions are involved in the binding of cell surface receptors and specific ligands therefor, and also in intracellular signal transduction from cytoplasm to nucleus. Therefore, disorders and abnormalities of intracellular signal transduction systems are closely associated with the pathogenesis of many serious diseases. Against this background, it is an urgent demand to create molecules capable of controlling (promoting or suppressing) protein-to-protein interactions as targets. At present, as a means of elucidating protein-to-protein interactions such as ligand-receptor interactions, and as a means of treating diseases resulting from signal cascade abnormalities, physiologically active peptides capable of interacting with target proteins are under active research and development.

Physiologically active peptides play an important role in controlling various physiological functions as signal transmitters in the body. However, in nature, physiologically active peptides occur only in trace amounts and are very difficult to purify; only less than 100 have been discovered to date. On the other hand, with the construction of genome databases, it is supposed that there are a significant number of orphan receptors deemed physiologically active peptide receptors, and searching ligands therefor is an important key to new drug development. As examples of peptide pharmaceuticals in clinical application or under development, there may be mentioned 1) hypothalamic hormone derivatives, 2) posterior pituitary hormone derivatives, 3) ANP derivatives, 4) calcium-regulating hormones, 5) peptide antibiotics, etc. Additionally, new physiologically active peptides have recently been discovered using cells that were allowed to express orphan receptors. Using this technique, Takeda Chemical Industries discovered metastin, a peptide ligand for an orphan receptor that suppresses cancer metastasis (see, for example, Nature, 411, 613 (2001)). It is expected that further investigations in search for other physiologically active peptides will be undertaken, resulting in the development of valuable peptide pharmaceuticals.

However, no effective methodology remains established to predict the amino acid sequence of a peptide capable of binding to and interacting with an optionally chosen amino acid sequence of protein; it is common practice to screen for physiologically active peptides by biochemical techniques. For example, there may be used a technique wherein a plurality of consecutive peptides consisting of 10-20 amino acids from the N-terminus to the C-terminus are synthesized from a protein known to bind to another protein, from among which peptides a physiologically active peptide is selected, or a technique wherein a physiologically active peptide is selected from a randomized peptide library using a phage library. However, such biochemical methods have been problematic in that much costs and time are required. Hence, there has been a demand for the development of a technique for both theoretically and more economically and conveniently designing a physiologically active peptide, rather than a conventional technique.

On the other hand, some theories to predict a physiologically active peptide sequence for target amino acid sequence have been proposed to date. Watson and Crick set forth the DNA strand model and asserted that base pairs existed but amino acid pairs did not exist; however, there had been the minority opinion that amino acid pairs might exist (see, for example, Journal of Theoretical Biology, vol. 94, p885-894 (1982)).

The sense-antisense theory, advocated by Blalock et al. (see, for example, Biochemical Biophysical Research Communication, vol. 121, p203-207 (1984)) is also premised on amino acid pairs, its contents being based on the hypothesis that two peptides encoded by two complementary DNAs, like bases, interact with each other. Based on this theory, it has been confirmed experimentally that some antisense peptides interact with sense peptides.

On the other hand, in response to the suggestion of Blalock et al. that sense peptides and antisense peptides are high in <complementariness in terms of the degree of hydrophobicity>, Fassina et al. showed in some experiments that a complementary peptide having a degree of hydrophobicity that is complementary (sharing the same absolute value, but having the reverse positive/negative sign) to the average degree of hydrophobicity of five or more consecutive odd-numbered amino acids in a peptide binds to the original peptide (see, for example, Archives of Biochemistry and Biophysics, vol. 296, 137-143 (1992)). However, numerous cases of failures have been reported for all these theories, the theories cannot be said to be satisfactory for the application to the prediction of common physiologically active peptides. Also, in all these theories, a plurality of amino acid candidates are available for each amino acid of target amino acid sequence; a vast number of candidate peptides are predicted, examining all of which takes vast amounts of time, costs, and labor.

Additionally, even if succeeding in obtaining a physiologically active peptide comprising an amino acid sequence that interacts with a target amino acid sequence, we encounter further problems. As target sites of protein to be targeted in drug innovation, there may be mentioned ligand binding sites (e.g., in the case of receptors), substrate binding sites (e.g., in the case of enzymes), protein-to-protein interaction sites (e.g., in the case of transcription factors, multimer-(e.g., dimer)-forming proteins), etc.; however, these target sites very often comprise a plurality of partial amino acid sequences localized apart on the primary structure, rather than of a single consecutive amino acid sequence. Therefore, even if a physiologically active peptide comprising an amino acid sequence that interacts with a target amino acid sequence is obtained, the amino acid sequence is often not preferable for other amino acid sequences present at the target site.

Additionally, provided that a target site of target protein comprises a plurality of partial amino acid sequences localized apart on the primary structure, it has traditionally been determined whether or not a particular peptide interacts with the target site of target protein by, for example, docking them using a molecular model and making an evaluation on an energy basis. To evaluate more peptides by such a technique, actually, for example, evaluation time per compound must be controlled up to about 1 minute in docking using a library comprising several thousands to several hundreds of thousands of low-molecular substances. However, because the number of variable portions of a peptide, even in the side chain only, is as many as up to 20, even for a 4-residue peptide, it took about 10 minutes per peptide to make an evaluation on Compac Alpha DS20E in, for example, flexible docking using AutoDock (see, for example, Journal of Computational Chemistry, vol. 19, p1639-1662 (1998)). For example, it is necessary to conduct docking $20^3$, i.e., 8000 times, in the case of a 3-residue peptide, and 64,000,000 times in the case of a 6-residue peptide; exhaustive screening is actually extremely difficult.

For the reasons above, there has been a strong demand for the development of a technique for quickly designing a physiologically active peptide possessing excellent capability of binding to a target site of a protein.

DISCLOSURE OF THE INVENTION

It is an object of the present invention to provide a means of designing a physiologically active peptide from the primary structure of target amino acid sequence, with higher certainty compared to the prior art, by a mathematical technique. It is another object of the present invention to provide a means of designing a physiologically active peptide that is preferred in view of not only a target amino acid sequence but also a target protein itself containing the target amino acid sequence.

The present inventors conducted an extensive investigation to accomplish the above-described objectives and succeeded in independently developing a new program enabling the extraction, with ranking, of a complementary amino acid sequence that satisfies the definition of complementariness described in detail below, for a profile waveform generated by applying an optionally chosen amino acid index, e.g., an index based on the degree of hydrophobicity or an electric property, to a target amino acid sequence. The present inventors also succeeded in independently developing a new program especially useful in designing an amino acid sequence that interacts with a target site of target protein, provided that this target site comprises a plurality of partial amino acid sequences localized apart on the primary structure.

The present inventors further independently developed a method, program, computer-readable recording medium and apparatus that enable the prediction of whether or not a complementary amino acid sequence extracted above is capable of acting as a preferable physiologically active peptide on a target protein itself containing a target amino acid sequence, and brought the present invention into completion.

Accordingly, the present invention is characterized as follows:

(1) A method of designing a physiologically active peptide capable of interacting with a target amino acid sequence, comprising:

(a1) a step for accepting an entry of sequence data on a target amino acid sequence, (b1) a step for converting said target amino acid sequence to one or more moving average profile waveforms in accordance with one or more specified amino acid indices, (c1) a step for generating a candidate for an amino acid sequence complementary to target amino acid sequence, and converting it to one or more complementary moving average profile waveforms using the same one or more amino acid indices as those in step (b1), (d1) a step for calculating each of complementariness parameters from the same amino acid index between one or more moving average profile waveforms for said target amino acid sequence and one or more complementary moving average profile waveforms of a candidate for complementary amino acid sequence, (e1) a step for storing a candidate for complementary amino acid sequence, along with said complementariness parameter, in a storage, (f1) a step for extracting a specified number of complementary amino acid sequences on the basis of information stored by step (e1), and (g1) a step for displaying an extracted complementary amino acid sequences as a candidate for physiologically active peptide.

(2) A method of (1) above, wherein said complementariness parameter is the correlation coefficient between a moving average profile waveform for said target amino acid sequence and a complementary moving average profile waveform of a candidate for complementary amino acid sequence.

(3) A method of (1) or (2) above, wherein said amino acid index is one or more indices selected from among indices based on the degree of hydrophobicity, indices based on an electric property, indices showing the likelihood of taking the α-helix and β-sheet, and indices showing the relative size of side chain volume.

(4) A method as described in any of (1)-(3) above, characterized in that the number of candidates for complementary amino acid sequence extracted as physiologically active peptides is narrowed down by taking steps (b1)-(f1) for a specified number of complementary amino acid sequences extracted in steps (a1)-(f1) using one or more specified amino acid indices, in one or more repeats, using one or more other amino acid indices.

(5) A method of designing a physiologically active peptide capable of interacting with a target protein, comprising:

(a1') a step for accepting an entry of sequence data on a target amino acid sequence in a target protein, (b1') a step for converting said target amino acid sequence to one or more moving average profile waveforms in accordance with one or more specified amino acid indices, (c1') a step for generating a candidate for an amino acid sequence complementary to target amino acid sequence, and converting it to one or more complementary moving average profile waveforms using the same one or more amino acid indices as those in step (b1'), (d1') a step for calculating each of complementariness parameters from the same amino acid index between one or more moving average profile waveforms for said target amino acid sequence and one or more complementary moving average profile waveforms of a candidate for complementary amino acid sequence, (e1') a step for storing a candidate for complementary amino acid sequence, along with said complementariness parameter, in a storage, (f1') a step for extracting a specified number of candidates for complementary amino acid sequence on the basis of information stored by step (e1'), (g1') a step for calculating an intermolecular energy parameter with a target site of target protein, for an extracted candidate for complementary amino acid sequence, (h1') a step for storing a candidate for complementary amino acid sequence, along with said intermolecular energy parameter, in a storage, (i1') a step for extracting a specified number of complementary amino acid sequences on the basis of information stored by step (h1'), and (j1') a step for displaying an extracted complementary amino acid sequence as a candidate for physiologically active peptide.

(6) A method of (5) above, wherein said complementariness parameter is the correlation coefficient between a moving average profile waveform for said target amino acid sequence and a complementary moving average profile waveform of a candidate for complementary amino acid sequence.

(7) A method of (5) or (6) above, wherein said amino acid index is one or more indices selected from among indices based on the degree of hydrophobicity, indices based on an electric property, indices showing the likelihood of taking the $\alpha$-helix and $\beta$-sheet, and indices showing the relative size of side chain volume.

(8) A method as described in any of (5)-(7) above, characterized in that the number of candidates for complementary amino acid sequence extracted as physiologically active peptides is narrowed down by taking steps (b1')-(f1') for a specified number of complementary amino acid sequences extracted in steps (a1')-(f1') using one or more specified amino acid indices, in one or more repeats, using one or more other amino acid indices, after which steps (g1')-(i1') are taken.

(9) A program for designing a physiologically active peptide capable of interacting with a target amino acid sequence, allowing a computer to execute:

(a1) a step for accepting an entry of sequence data on a target amino acid sequence, (b1) a step for converting said target amino acid sequence to one or more moving average profile waveforms in accordance with one or more specified amino acid indices, (c1) a step for generating a candidate for an amino acid sequence complementary to target amino acid sequence, and converting it to one or more complementary moving average profile waveforms using the same one or more amino acid indices as those in step (b1), (d1) a step for calculating each of complementariness parameters from the same amino acid index between one or more moving average profile waveforms for said target amino acid sequence and one or more complementary moving average profile waveforms of a candidate for complementary amino acid sequence, (e1) a step for storing a candidate for complementary amino acid sequence, along with said complementariness parameter, in a storage, (f1) a step for extracting a specified number of complementary amino acid sequences on the basis of information stored by step (e1), and (g1) a step for displaying an extracted complementary amino acid sequence as a candidate for physiologically active peptide.

(10) A program of (9) above, wherein said complementariness parameter is the correlation coefficient between a moving average profile waveform for said target amino acid sequence and a complementary moving average profile waveform of a candidate for complementary amino acid sequence.

(11) A program of (9) or (10) above, wherein said amino acid index is one or more indices selected from among indices based on the degree of hydrophobicity, indices based on an electric property, indices showing the likelihood of taking the $\alpha$-helix and $\beta$-sheet, and indices showing the relative size of side chain volume.

(12) A program as described in any of (9)-(11) above, characterized in that the number of candidates for complementary amino acid sequence extracted as physiologically active peptides is narrowed down by taking steps (b1)-(f1) for a specified number of complementary amino acid sequences extracted in steps (a1)-(f1) using one or more specified amino acid indices, in one or more repeats, using one or more other amino acid indices.

(13) A program for designing a physiologically active peptide capable of interacting with a target protein, allowing a computer to execute:

(a1') a step for accepting an entry of sequence data on a target amino acid sequence in a target protein, (b1') a step for converting said target amino acid sequence to one or more moving average profile waveforms in accordance with one or more specified amino acid indices, (c1') a step for generating a candidate for an amino acid sequence complementary to target amino acid sequence, and converting it to one or more complementary moving average profile waveforms using the same one or more amino acid indices as those in step (b1'), (d1') a step for calculating each of complementariness parameters from the same amino acid index between one or more moving average profile waveforms for said target amino acid sequence and one or more complementary moving average profile waveforms of a candidate for complementary amino acid sequence, (e1') a step for storing a candidate for complementary amino acid sequence, along with said complementariness parameter, in a storage, (f1') a step for extracting a specified number of candidates for complementary amino acid sequence on the basis of information stored by step (e1'), (g1') a step for calculating an intermolecular energy parameter with a target site of target protein, for an extracted candidate for complementary amino acid sequence, (h1') a step for storing a candidate for complementary amino acid sequence, along with said intermolecular energy parameter, in a storage, (i1') a step for extracting a specified number of complementary amino acid sequences on the basis of information stored by step (h1'), and (j1') a step for displaying an extracted complementary amino acid sequence as a candidate for physiologically active peptide.

(14) A program of (13) above, wherein said complementariness parameter is the correlation coefficient between a moving average profile waveform for said target amino acid sequence and a complementary moving average profile waveform of a candidate for complementary amino acid sequence.

(15) A program of (13) or (14) above, wherein said amino acid index is one or more indices selected from among indices based on the degree of hydrophobicity, indices based on an electric property, indices showing the likelihood of taking the $\alpha$-helix and $\beta$-sheet, and indices showing the relative size of side chain volume.

(16) A program as described in any of (13)-(15) above, characterized in that the number of candidates for complementary amino acid sequences extracted as physiologically active peptides is narrowed down by taking steps (b1')-(f1') for a specified number of complementary amino acid sequences extracted in steps (a1')-(f1') using one or more specified amino acid indices, in one or more repeats, using one or more other amino acid indices, after which steps (g1')-(i1') are taken.

(17) A computer-readable recording medium containing a program as described in any of (9)-(16) above.

(18) An apparatus for designing a physiologically active peptide capable of interacting with a target amino acid sequence, provided with (A) a data entry portion, (B) a data editing portion, (C) a complementary amino acid sequence candidate generation portion, (D) a complementariness calculation portion, (E) a complementary amino acid sequence candidate memory portion, (F) a complementary amino acid sequence search portion, and (G) a complementary amino acid sequence display portion, wherein:

said data entry portion includes (a1) a means of accepting an entry of sequence data on a target amino acid sequence, said data editing portion includes (b1) a means of converting said target amino acid sequence to one or more moving average profile waveforms in accordance with one or more specified amino acid indices, said complementary amino acid sequence candidate generation portion includes (c1) a means of generating a candidate for an amino acid sequence complementary to target amino acid sequence, and converting it to one or more complementary moving average profile waveforms using the same one or more amino acid indices as those for means (b1), said complementariness calculation portion includes (d1) a means of calculating each of complementariness parameters from the same amino acid index between one or more moving average profile waveforms for said target amino acid sequence and one or more complementary moving average profile waveforms of a candidate for complementary amino acid sequence, said complementary amino acid sequence candidate memory portion includes (e1) a means of storing a candidate for complementary amino acid sequence, along with said complementariness parameter, said complementary amino acid sequence search portion includes (f1) a means of extracting a specified number of complementary amino acid sequences on the basis of information stored by means (e1), and said complementary amino acid sequence display portion includes (g1) a means of displaying a complementary amino acid sequence extracted by means (f1) as a candidate for physiologically active peptide.

(19) An apparatus of (18) above, wherein said complementariness parameter is the correlation coefficient between a moving average profile waveform for said target amino acid sequence and a complementary moving average profile waveform of a candidate for complementary amino acid sequence.

(20) An apparatus of (18) or (19) above, wherein said amino acid index is one or more indices selected from among indices based on the degree of hydrophobicity, indices based on an electric property, indices showing the likelihood of taking the α-helix and β-sheet, and indices showing the relative size of side chain volume.

(21) An apparatus for designing a physiologically active peptide capable of interacting with a target protein, provided with (A) a data entry portion, (B) a data editing portion, (C) a complementary amino acid sequence candidate generation portion, (D) a complementariness calculation portion, (E) a complementary amino acid sequence candidate memory portion, (F) a complementary amino acid sequence search portion, and (G) a complementary amino acid sequence display portion, wherein:

said data entry portion includes (a1') a means of accepting an entry of sequence data on a target amino acid sequence in a target protein, said data editing portion includes (b1') a means of converting said target amino acid sequence to one or more moving average profile waveforms in accordance with one or more specified amino acid indices, said complementary amino acid sequence candidate generation portion includes (c1') a means of generating a candidate for an amino acid sequence complementary to target amino acid sequence, and converting it to one or more complementary moving average profile waveforms using the same one or more amino acid indices as those for means (b1'), said complementariness calculation portion includes (k1') a means of calculating each of complementariness parameters from the same amino acid index between one or more moving average profile waveforms for said target amino acid sequence and one or more complementary moving average profile waveforms of a candidate for complementary amino acid sequence, and further calculating an intermolecular energy parameter with a target site of target protein, said complementary amino acid sequence candidate memory portion includes (l1') a means of storing a candidate for complementary amino acid sequence, along with said complementariness parameter and said intermolecular energy parameter, said complementary amino acid sequence search portion includes (m1') a means of extracting a specified number of complementary amino acid sequences on the basis of information stored by means (k1'), and said complementary amino acid sequence display portion includes (n1') a means of displaying a complementary amino acid sequence extracted by said complementary amino acid sequence search portion as a candidate for physiologically active peptide.

(22) An apparatus of (21) above, wherein said complementariness parameter is the correlation coefficient between a moving average profile waveform for said target amino acid sequence and a complementary moving average profile waveform of a candidate for complementary amino acid sequence.

(23) An apparatus of (21) or (22) above, wherein said amino acid index is one or more indices selected from among indices based on the degree of hydrophobicity, indices based on an electric property, indices showing the likelihood of taking the α-helix and β-sheet, and indices showing the relative size of side chain volume.

(24) A program of any of (13)-(16) above, further including between step (i1') and step (j1'):

(I) a step for generating an amino acid sequence with an amino acid variation introduced to an amino acid sequence extracted in step (i1'), (II) a step for calculating an intermolecular energy parameter between an amino acid sequence generated in step (I) and a target site of target protein, and (III) a step for comparing an intermolecular energy parameter calculated in step (II) with an intermolecular energy parameter between an amino acid sequence extracted in step (i1') and a target site of target protein as a control, and extracting an amino acid sequence having an intermolecular energy parameter that is stabler than the intermolecular energy parameter of the control.

(25) A program for designing a physiologically active peptide capable of interacting with a target protein, allowing a computer to execute:

(a2) a step for identifying the interaction region in a protein that interacts with a target site of target protein, and (b2) a step for extracting an amino acid sequence of an optionally chosen length from said interaction region.

(26) A program for designing a physiologically active peptide capable of interacting with a target protein, allowing a computer to execute:

(a2') a step for identifying the interaction region in a protein that interacts with a target site of target protein, (b2') a step for extracting an amino acid sequence of an optionally chosen length from said interaction region, (c2') a step for calculating an intermolecular energy parameter with a target site of target protein, for an extracted amino acid sequence, (d2') a step for storing said amino acid sequence, along with said intermolecular energy parameter, in a storage, (e2') a step for extracting a specified number of amino acid sequences on the basis of information stored by step (d2'), and (f2') a step for displaying an extracted amino acid sequence as a candidate for physiologically active peptide.

(27) A program of (26) above, further including between step (e2') and step (f2')

(I) a step for generating an amino acid sequence with an amino acid variation introduced to an amino acid sequence extracted in step (e2'), (II) a step for calculating an intermolecular energy parameter between an amino acid sequence generated in step (I) and a target site of target protein, and (III) a step for comparing an intermolecular energy parameter calculated in step (II) with an intermolecular energy parameter between an amino acid sequence extracted in step (e2') and a target site of target protein as a control, and extracting an amino acid sequence having an intermolecular energy parameter that is stabler than the intermolecular energy parameter of the control.

(28) A program for designing a physiologically active peptide capable of interacting with a target protein, allowing a computer to execute:

(a3) a step for exhaustively generating amino acid sequences of a constant length, and randomly selecting amino acid sequences from among them for extraction as a library for analysis, (b3) a step for calculating an intermolecular energy parameter for each of the amino acid sequences extracted as a library for analysis, (c3) a step for generating a score matrix based on amino acid prevalence using an intermolecular energy parameter calculated in step (b3), (d3) a step for calculating a score based on amino acid prevalence using a score matrix based on amino acid prevalence, (e3) a step for conducting a correlation analysis between an intermolecular energy parameter calculated in step (b3) and said score to obtain a regression equation, (f3) a step for converting a score matrix based on amino acid prevalence to a matrix based on an amino acid position-dependent intermolecular energy parameter using said regression equation, (g3) a step for calculating an amino acid position-dependent intermolecular energy parameter value from a matrix based on an amino acid position-dependent intermolecular energy parameter, and (h3) a step for extracting an amino acid sequence not higher than a specified amino acid position-dependent intermolecular energy parameter value.

(29) A program for designing a physiologically active peptide capable of interacting with a target protein, allowing a computer to execute:

(a3') a step for exhaustively generating amino acid sequences of a constant length, and randomly selecting amino acid sequences from among them for extraction as a library for analysis, (b3') a step for calculating an intermolecular energy parameter for each of the amino acid sequences extracted as a library for analysis, (c3') a step for generating a score matrix based on amino acid prevalence using an intermolecular energy parameter calculated in step (b3'), (d3') a step for calculating a score based on amino acid prevalence using a score matrix based on amino acid prevalence, (e3') a step for conducting a correlation analysis between an intermolecular energy parameter calculated in step (b3') and said score to obtain a regression equation, (f3') a step for converting a score matrix based on amino acid prevalence to a matrix based on an amino acid position-dependent intermolecular energy parameter using said regression equation, (g3') a step for calculating an amino acid position-dependent intermolecular energy parameter value from a matrix based on an amino acid position-dependent intermolecular energy parameter, (h3') a step for extracting an amino acid sequence not higher than a specified amino acid position-dependent intermolecular energy parameter value, (i3') a step for calculating an intermolecular energy parameter with a target site of target protein, for an extracted amino acid sequence, (j3') a step for storing said amino acid sequence, along with said intermolecular energy parameter, in a storage, (k3') a step for extracting a specified number of amino acid sequences on the basis of information stored by step (j3'), and (l3') a step for displaying an amino acid sequence extracted in step (k3') as a candidate for physiologically active peptide.

(30) A program of (29) above, further including between step (k3') and step (l3'):

(I) a step for generating an amino acid sequence with an amino acid variation introduced to an amino acid sequence extracted in step (k3'), (II) a step for calculating an intermolecular energy parameter between an amino acid sequence generated in step (I) and a target site of target protein, and (III) a step for comparing an intermolecular energy parameter calculated in step (II) with an intermolecular energy parameter between an amino acid sequence extracted in step (k3') and a target site of target protein as a control, and extracting an amino acid sequence having an intermolecular energy parameter that is stabler than the intermolecular energy parameter of the control.

(31) An apparatus for designing a physiologically active peptide capable of interacting with a target protein, provided with (A2) an interaction region identification portion, (B2) a first amino acid sequence search portion, (C2) an intermolecular energy calculation portion, (D2) an amino acid sequence memory portion, (E2) a second amino acid sequence search portion, and (F2) an amino acid sequence display portion, wherein:

said interaction region identification portion includes (a2') a means of identifying the interaction region in a protein molecule that interacts with a target site of target protein, said first amino acid sequence search portion includes (b2') a means of extracting an amino acid sequence of an optionally chosen length from said interaction region, said intermolecular energy calculation portion includes (c2') a means of calculating an intermolecular energy parameter with a target site of target protein, for an extracted amino acid sequence, said amino acid sequence memory portion includes (d2') a means of storing said amino acid sequence, along with said intermolecular energy parameter, in a storage, said second amino acid sequence search portion includes (e2') a means of extracting a specified number of amino acid sequences on the basis of information stored by means (d2'), and said amino acid sequence display portion includes (f2') a means of displaying an extracted amino acid sequence as a candidate for physiologically active peptide.

(32) An apparatus for designing a physiologically active peptide capable of interacting with a target protein, provided with (A3) a first amino acid sequence search portion, (B3) a first intermolecular energy calculation portion, (C3) a score matrix generation portion, (D3) a score calculation portion, (E3) a regression equation generation portion, (F3) a matrix conversion portion, (G3) an amino acid position-dependent energy calculation portion, (H3) a second amino acid sequence search portion, (I3) a second intermolecular energy calculation portion, (J3) an amino acid sequence memory portion, (K3) a third amino acid sequence search portion, and (L3) an amino acid sequence display portion, wherein:

said first amino acid sequence search portion includes (a3') a means of exhaustively generating amino acid sequences of a constant length, and randomly selecting amino acid sequences from among them for extraction as a library for analysis, said first intermolecular energy calculation portion includes (b3') a means of calculating an intermolecular energy parameter for each of the amino acid sequences extracted as a library for analysis, said score matrix generation portion includes (c3') a means of generating a score matrix based on amino acid prevalence using an intermolecular energy parameter calculated by means (b3'), said score calculation portion includes (d3') a means of calculating a score based on amino acid prevalence using a score matrix based on amino acid prevalence, said regression equation generation portion includes (e3') a means of conducting a correlation analysis between an intermolecular energy parameter calculated by means (b3') and said score to obtain a regression equation, said matrix conversion portion includes (f3') a means of converting a score matrix based on amino acid prevalence to a matrix based on an amino acid position-dependent intermolecular energy parameter using said regression equation, said amino acid position-dependent energy calculation portion includes (g3') a means of calculating an amino acid position-dependent intermolecular energy parameter value from a matrix based on an amino acid position-dependent intermolecular energy parameter, said second amino acid sequence search portion includes (h3') a means of extracting an amino acid sequence not higher than a specified amino acid position-dependent intermolecular energy parameter value, said second intermolecular energy calculation portion includes (i3') a means of calculating an intermolecular energy parameter with a target site of target protein, for an extracted amino acid sequence, said amino acid sequence memory portion includes (j3') a means of storing said amino acid sequence, along with said intermolecular energy parameter, in a storage, said amino acid sequence search portion includes (k3') a means of extracting a specified number of amino acid sequences on the basis of information stored by step (j3'), and said amino acid sequence display portion includes (l3') a means of displaying an amino acid sequence extracted in step (k3') as a candidate for physiologically active peptide.

BRIEF DESCRIPTION OF THE DRAWINGS

FIG. 14 shows a result of first screening (amino acid position-dependent binding significance evaluation) with caspase-3 as the target protein. FIG. 14B shows the PSS matrix at each position of the motif. FIG. 14C shows the PSG matrix at each position of the motif.

FIG. 15 shows a result of first screening (amino acid position-dependent binding significance evaluation) with caspase-7 as the target protein. FIG. 15B shows the PSS matrix at each position of the matrix. FIG. 15C shows the PSG matrix at each position of the matrix.

FIG. 16 shows a result of first screening (amino acid position-dependent binding significance evaluation) with caspase-8 as the target protein. FIG. 16B shows the PSS matrix at each position of the motif. FIG. 16C shows the PSG matrix at each position of the motif.

FIG. 17 shows a result of first screening (amino acid position-dependent binding significance evaluation) with caspase-9 as the target protein. FIG. 17B shows the PSS matrix at each position of the motif. FIG. 17C shows the PSG matrix at each position of the motif.

DETAILED DESCRIPTION OF THE INVENTION

Figure 1:
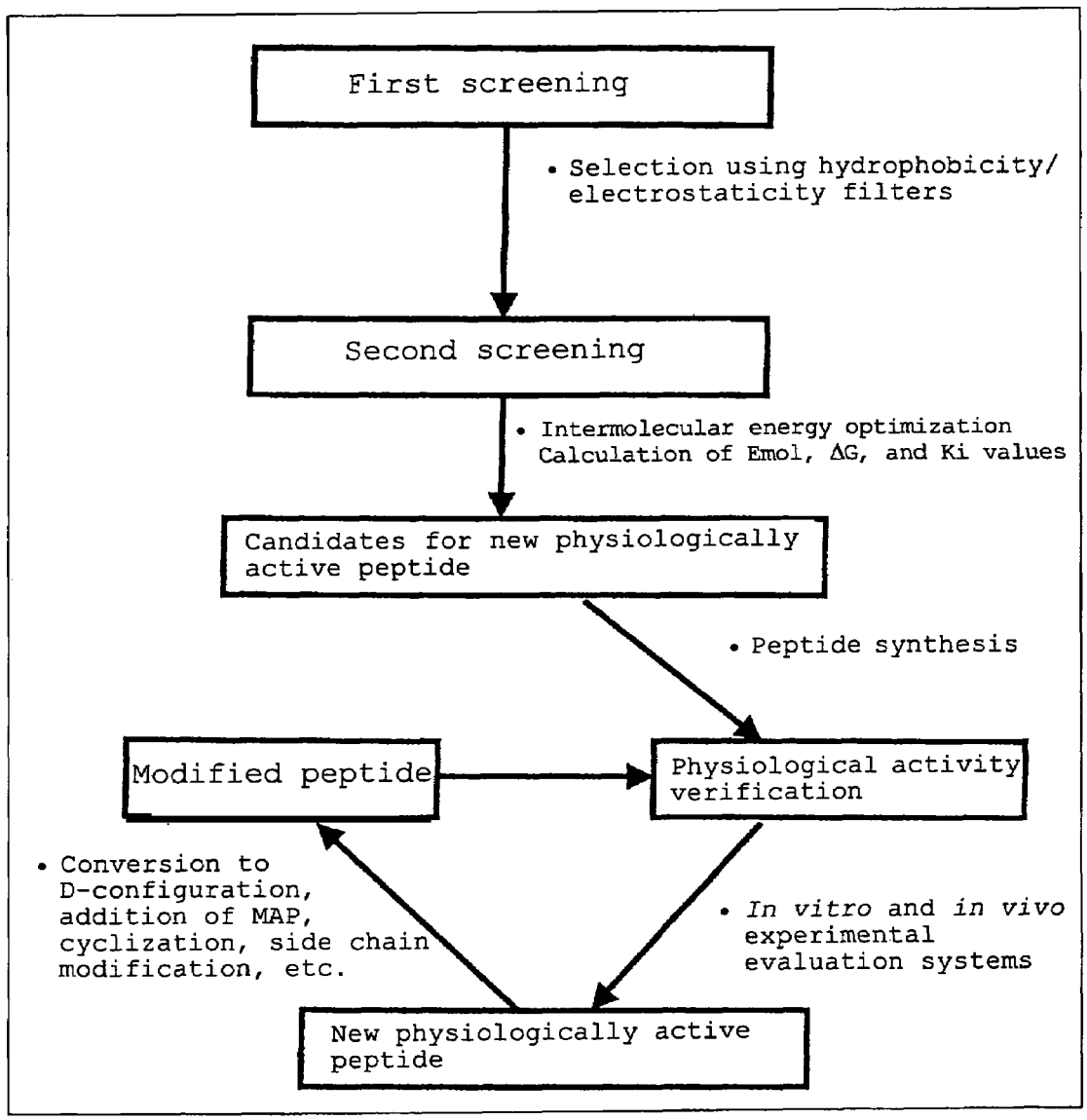
FIG. 1 shows an example of designing a physiologically active peptide.

First, the terms used in the present specification and their usage are described in the order of first screening, second screening and third screening. Although a plurality of evaluation methods can be used for first screening, a more appropriate evaluation method can be selected as appropriate according to target protein. This selection is performed from the viewpoint of the kind of target protein, the characteristics of the target site of the protein to be targeted, whether or not a known ligand (protein) exists, whether or not the interaction region has been identified, etc.

I. First Screening

For first screening, there may be used methods based on amino acid complementariness profile waveform evaluation, amino acid interaction region evaluation, and amino acid position-dependent binding significance evaluation. Amino acid complementariness profile waveform evaluation is useful mainly in designing a physiologically active peptide that interacts with a target site comprising a consecutive amino acid sequence. On the other hand, amino acid interaction region evaluation and amino acid position-dependent binding significance evaluation are not only useful in designing a physiologically active peptide that interacts with a target site comprising a consecutive amino acid sequence, but also useful in designing a physiologically active peptide that interacts with a target site of target protein, provided that this target site comprises a plurality of partial amino acid sequences localized apart on the primary structure. Specifically, a design technique in first screening is selected according to target protein. Regarding design techniques, the most appropriate can be selected by the three judgment criteria of the availability of ligand information, the consecutiveness/non-consecutiveness of target site, and whether or not an enzyme or a surface pocket is present. Each criterion is summarized in Table 1 below and explained in due order.

TABLE 1

| Features of First Screening | | |
|---|---|---|
| Design technique | Subject molecules | Features |
| ① Amino acid complementariness profile waveform evaluation | All proteins | A design is formulated from amino acid sequence information for a functional region on target protein. A profile waveform is generated from target amino acid sequence on the basis of a physicochemical amino acid index, and a complementary peptide library is generated. Binding protein (ligand) information is unnecessary. However, designing is possible only for a |

TABLE 1-continued

| Features of First Screening | | |
|---|---|---|
| Design technique | Subject molecules | Features |
| ② Amino acid interaction region evaluation | All proteins | consecutive amino acid sequence region. A design is formulated on the basis of the amino acid sequence of a protein (ligand) molecule that binds to a target protein. From an amino acid sequence region in a ligand molecule that interacts with target protein, a 3~7-residue fragmented peptide library is generated. Designing is also possible for a region wherein the amino acid sequence is non-consecutive. |
| ③ Amino acid position-dependent binding significance evaluation | Enzymes or proteins having a pocket on the molecular surface | A design is formulated by evaluating the significance of amino acid position-dependent binding in binding pocket. Although the structure of a complex of target protein and ligand is required, a peptide library is generated by constructing a binding evaluation score intrinsic to the target protein on the basis thereof. Designing is also possible for a non-consecutive region. |

A. Amino Acid Complementariness Profile Waveform Evaluation (Generation of Complementary Peptide Library)

Amino acid complementariness profile waveform evaluation is a method of evaluating a peptide having an amino acid sequence that interacts with a target amino acid sequence on the basis of a physicochemical amino acid index of the target amino acid sequence. This evaluation method is especially useful when the target site of target protein comprises a single consecutive amino acid sequence. Terms used in amino acid complementariness profile waveform evaluation and a summary of this evaluation are described below.

A "target amino acid sequence" refers to an amino acid sequence to be targeted in designing a complementary amino acid sequence. Accordingly, the present invention is intended to design a physiologically active peptide comprising an amino acid sequence that interacts with this "target amino acid sequence" (complementary amino acid sequence). Preferably, the target amino acid sequence is an amino acid sequence found in a target protein (e.g., receptor, enzyme, etc.) to be targeted in drug innovation.

A "complementary amino acid sequence" refers to an amino acid sequence that satisfies the definition of "complementary (complementariness)" in the present invention. Here, amino acids in a complementary amino acid sequence are not limited to natural amino acids (α-amino acids in the L-configuration). For example, each amino acid or dipeptide in a complementary amino acid sequence as a unit, as converted to an equivalent of natural amino acid (hereinafter abbreviated "amino acid equivalent" as necessary) or an equivalent of a dipeptide consisting of natural amino acids (hereinafter abbreviated "dipeptide equivalent" as necessary), can be used as a complementary amino acid sequence. As amino acids in a complementary amino acid sequence, there may be used, as necessary, β-amino acids and γ-amino acids as well.

As amino acid equivalents, there may be mentioned, for example, non-natural α-amino acids (e.g., D-configuration derivatives of natural amino acids), and a pseudo-amino acid unit in an optionally chosen dipeptide equivalent commonly known in the art (e.g., dipeptide equivalents shown in Table 2 below). Here, the pseudo-amino acid unit refers to a unit corresponding to any amino acid produced upon cleavage of the amide bond in the dipeptide comprising a natural amino acid shown in Table 2 below, and is exemplified by those resulting from cleavage of the thioamide bond, ester bond, amide bond, double bond, etc. in the dipeptide equivalents shown in Table 2 below. Those skilled in the art are able to understand the pseudo-amino acid unit in each dipeptide equivalent by referring/comparing the structures of the dipeptide comprising natural amino acids and the dipeptide equivalents in Table 2.

TABLE 2

Dipeptide equivalent to a dipeptide consisting natural amino acid

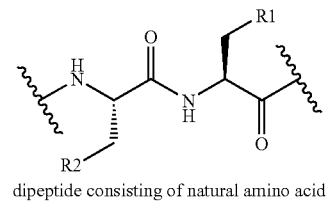

dipeptide consisting of natural amino acid

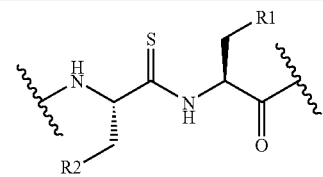

thioamide

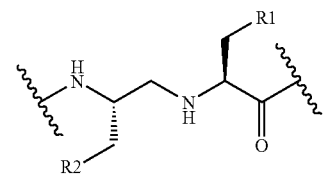

carba-substitution of amidocarbonyl

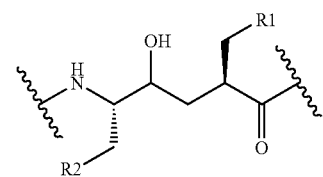

hydroxyethylene

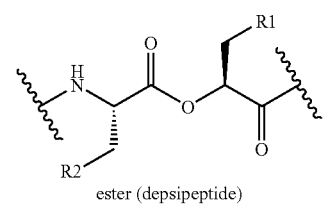

ester (depsipeptide)

TABLE 2-continued

Dipeptide equivalent to a dipeptide consisting natural amino acid

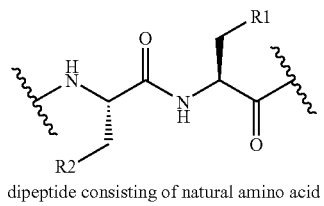

dipeptide consisting of natural amino acid

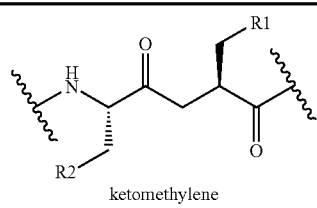

ketomethylene

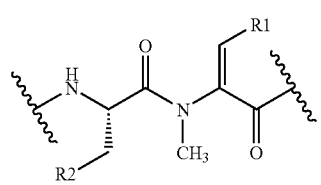

dehydroamino acid

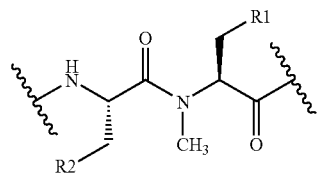

N-methylation

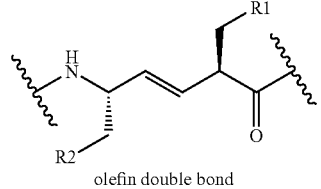

olefin double bond

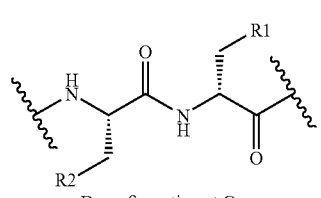

D-configuration at Cα

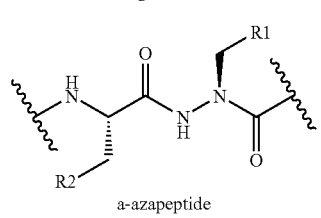

a-azapeptide

TABLE 2-continued

Dipeptide equivalent to a dipeptide consisting natural amino acid

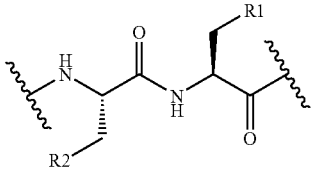

dipeptide consisting of natural amino acid

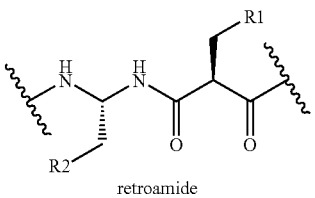

retroamide

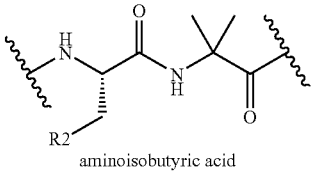

aminoisobutyric acid

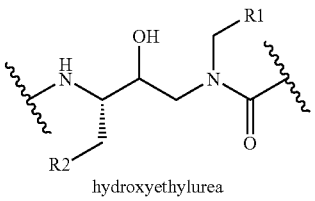

hydroxyethylurea

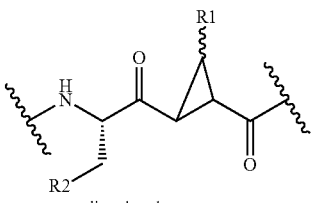

diacylcyclopropane

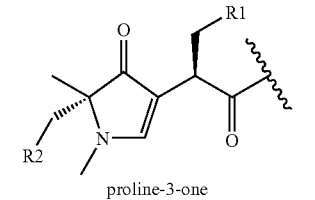

proline-3-one

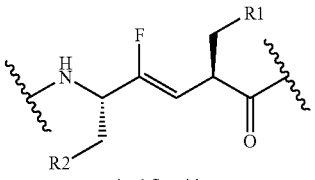

vinyl fluoride

As dipeptide equivalents, there may be mentioned, for example, dipeptides comprising non-natural α-amino acids only (e.g., D-configuration derivatives of natural amino acids), dipeptides comprising a natural amino acid (L-configuration) and a non-natural α-amino acid (e.g., D-configuration derivatives of natural amino acids), and the dipeptide equivalents shown in Table 2 below. For details of amino acid equivalents and dipeptide equivalents, see, for example, Spatola, A. F. (1983) Peptide backbone modifications: structure-activity analysis of peptides containing amide bond surrogates. In Weinstein, B. (ed.) Chemistry and Biochemistry of Amino Acids, Peptides and Proteins, pp. 267-357. Marcel Dekker, New York.; Fauchere, J.-L.(1986) Elements for the rational design of peptide drugs. In Testa, B. (ed.) Advances in Drug Research, pp. 26-69. Academic Press, London.

"Complementary (complementariness)" refers to the relationship between an amino acid sequence having a profile waveform close to a complementary moving average profile waveform having a negative correlation with a moving average profile waveform obtained by a low-pass by moving-averaging a profile waveform obtained by applying an optionally chosen amino acid index to a target amino acid sequence, and the target amino acid sequence. Therefore, if the moving average profile waveform of an amino acid sequence has a smaller value of the correlation coefficient R (described below) with the complementary moving average profile waveform of target amino acid sequence than that of the moving average profile waveform of another amino acid sequence, the amino acid sequence is "more complementary" to the target amino acid sequence.

A "profile waveform" refers to a waveform generated by applying an amino acid index to an amino acid sequence.

A "moving average profile waveform" refers to a waveform obtained by moving-averaging a profile waveform over a specified window width. If we write a profile waveform obtained by applying an optionally chosen amino acid index to a target amino acid sequence as $T_i$, moving average profile waveform $x_j$ at optionally chosen (odd-numbered) window width w is shown by [Equation 1].

$$x_j = \frac{1}{w}\sum_{i=j-s}^{i=j+s} T_i \qquad \text{[Equation 1]}$$

Where $s=\lfloor w/2 \rfloor$ j ranges from s to (n−s−1). n is the length of target sequence.

Here $\lfloor x \rfloor$ represents the greatest of the integers of x or less (rounded off).

In the present specification, a moving average profile waveform of complementary amino acid sequence, in particular, is referred to as "complementary moving average profile waveform". If we write a profile waveform obtained by applying an optionally chosen amino acid index to a candidate for complementary amino acid sequence as $C_i$, complementary moving average profile waveform $y_j$ at optionally chosen (odd-numbered) window width w is shown by [Equation 2].

$$y_j = \frac{1}{w}\sum_{i=j-s}^{i=j+s} C_i \qquad \text{[Equation 2]}$$

A "window width" refers to the width of a range over which, in generating a moving average profile waveform, profile waveforms are summed. Although the window width can be set forth at an optionally chosen odd number, it is usually set forth at 1-13, preferably 3-13, more preferably 5-11.

An "amino acid index" refers to an index wherein a physicochemical characteristic of amino acid is expressed numerically. More than 400 kinds of amino acid indices have been compiled to date; these indices can be searched in, for example, AAindex, a database provided by the Kyoto University Institute for Chemical Research, etc. These amino acid indices can be roughly divided into five characteristics: hydrophobicity, likelihood of β-structure formation, likelihood of α-helix formation, likelihood of turn formation, and side chain physicochemical properties (e.g., relative size of side chain volume) (see, for example, Tomii and Kanehisa, Protein Eng., 9, 27-36 (1996)). In the present invention, an amino acid index used in generating a profile waveform can be selected from among about 400 kinds. Additionally, the above-described database may be installed in conjunction with the program in a memory device of the apparatus (described below), or may be installed in an outside memory device accessible by a communication such as via the Internet.

When an amino acid equivalent is used in a complementary amino acid sequence, an amino acid index of the equivalent is possibly not registered in any existing database; however, for a D-configuration derivative of natural amino acid out of amino acid equivalents, the value of an amino acid index of the natural amino acid (L-configuration) may be used as is. Additionally, a value of a particular amino acid index can be calculated by a method commonly known in the art (see, for example, Eisenberg D, et al., J. Ann. Rev. Biochem., 53, 596-623 (1984)). Therefore, according to these methods described in the literature, it is possible to calculate a value of a particular amino acid index for an optionally chosen amino acid equivalent (including D-configuration derivatives of natural amino acids).

As examples of preferable amino acid indices used in the present invention, there may be mentioned indices based on the degree of hydrophobicity, indices based on an electric property, indices showing the likelihood of taking the α-helix and β-sheet, and indices showing the relative size of side chain volume; an amino acid index is more preferably selected from among indices based on the degree of hydrophobicity and indices based on an electric property. As indices based on the degree of hydrophobicity, there may be mentioned, for example, the hydropathy index of Kyte-Doolittle, the hydrophobicity of Jones et al., and the Consensus Normalized Hydrophobicity scale (see, for example, Eisenberg D, et al., J. Ann. Rev. Biochem., 53, 596-623 (1984)), with preference given to the Consensus Normalized Hydrophobicity scale. An index based on an electric property refers to an index showing the degree of molecule polarization or an electrostatic interaction, and is exemplified by the localized electrical effect of Fauchere et al., the polarity of Grantham et al., and the electron-ion interaction potential (EIIP), with preference given to the electron-ion interaction potential (EIIP) (see, for example, Cosic I, et al., J IEEE Trans. Biomed. Eng., 32, 337-341 (1985)).

A "complementariness parameter" refers to a value indicating the complementariness between a moving average profile waveform of a target amino acid sequence and a complementary moving average profile waveform of a complementary amino acid sequence. An example of complementariness parameter is the correlation coefficient R shown by [Equation 3] below.

$$R = \frac{\sum_{j=s}^{n-s-1}(x_j - \bar{x})(y_j - \bar{y})}{\sqrt{\sum_{j=s}^{n-s-1}(x_j - \bar{x})^2}\sqrt{\sum_{j=s}^{n-s-1}(y_j - \bar{y})^2}} \quad \text{[Equation 3]}$$

$\bar{x}$: mean value of moving average profile waveform $\bar{y}$: mean value of complementary moving average profile waveform Here, the mean value of moving average profile waveform is shown by [Equation 4].

$$\bar{x} = \frac{1}{n}\sum_{j=s}^{n-s-1} x_j \quad \text{[Equation 4]}$$

The mean value of complementary moving average profile waveform is shown by [Equation 5].

$$\bar{y} = \frac{1}{n}\sum_{j=s}^{n-s-1} y_j \quad \text{[Equation 5]}$$

Those skilled in the art are able to use a value calculated from a numerical formula derived from [Equation 3] above as a complementariness parameter, as well as the correlation coefficient of [Equation 3] above.

A "mean value parameter ($P_{ave}$)" refers to (i) the mean value of the profile waveform of target amino acid sequence, shown by [Equation 6] below $$P_{ave} = \frac{1}{L}\sum_{i=1}^{L} T_i \quad \text{[Equation 6]}$$

or (ii) the mean value of the amino acid index used, shown by [Equation 7] below $$P_{ave} = \frac{1}{20}\sum_{i=1}^{20} Index_i \quad \text{[Equation 7]}$$

Index represents an amino acid index.

A "filter value" refers to a value set forth to narrow down the number of candidates for complementary amino acid sequence; in the present invention, a filter value concerning a complementariness parameter and a filter value concerning a mean value parameter, in particular, are used.

As a filter value concerning a complementariness parameter, there may be used, for example, the correlation coefficient filter value $R_t$ (based on this value $R_t$, only a candidate for complementary amino acid sequence having a correlation coefficient R satisfying the requirement of $R<R_t$ is selected). Preferably, a negative correlation is required between a moving average profile waveform of target amino acid sequence and a complementary moving average profile waveform of complementary amino acid sequence. Therefore, the correlation coefficient filter value $R_f$ can be set forth at an optionally chosen negative value of −1 or more, and is preferably set forth at $R_f \leq -0.9$. A filter value concerning a complementariness parameter may be set forth in advance before calculating the complementariness parameter, or may be set forth as appropriate after the calculation.

As filter values concerning a mean value parameter, the $P_{ave}$ filter values "a" and "b" are set forth. Based on these values "a" and "b", only a candidate for complementary amino acid sequence having a $P_{ave}$ satisfying the requirement of $a < P_{ave} < b$ is selected. When $P_{ave}$ is a value for high degrees of hydrophobicity, the obtained physiologically active peptide will be insoluble and make experimentation difficult, the values "a" and "b" are preferably set forth at values for high degrees of hydrophilicity. A $P_{ave}$ filter value may be set forth in advance before calculating $P_{ave}$, or may be set forth as appropriate after the calculation of Pave.

Although only the correlation coefficient filter value $R_f$ may be used as the filter value, the $P_{ave}$ filter values "a" and "b" are preferably used additionally. In this case, the conditional expression is as follows:

if (R<Rt and a<Pave<b)  [Equation 8]

then proceed to second screening

Additionally, an amino acid sequence selected by this evaluation method (complementary peptide library) may be converted with an amino acid equivalent or dipeptide equivalent, with each amino acid or dipeptide in the amino acid sequence as 1 unit. Because an amino acid equivalent or dipeptide equivalent is similar in properties to a natural amino acid or dipeptide thereof, amino acid sequences containing these equivalents are of course considered to bind to target proteins.

Amino acid sequences selected by this evaluation method (complementary peptide library) are preferably subjected to the second screening described below.

B. Amino Acid Interaction Region Evaluation (Generation of Fragmented Peptide Library)

Amino acid interaction region evaluation refers to a method of designing a peptide capable of binding to a target protein, using the primary structure (amino acid sequence) information of a protein that interacts with the target protein. This evaluation method is especially useful when the primary structure (amino acid sequence) of a protein that interacts, or is expected to interact, with a target protein, is known. Terms used in amino acid interaction region evaluation and a summary of this evaluation are described below.

Regarding the "interaction region" in a protein that interacts with a target site of target protein, if there is a protein having a region capable of interacting with a target protein already identified, that region is selected. If a plurality of interaction regions are present in one protein, the plurality of regions are selected as the interaction regions. If a plurality of proteins are known to interact with a target protein, it is also possible to obtain a plurality of interaction regions from these proteins. On the other hand, if the protein that interacts with a target protein is known per se but the interaction region thereof has not been identified, this region can be selected by a method commonly known in the art (e.g., RBD method (see, for example, Gallet X. et al, J. Mol. Biol., 302, 917-926 (2000)). Although this evaluation method is applicable in cases where the protein that interacts with a target protein is unknown per se, it is preferable that this evaluation method be applied in cases where the protein that interacts with a target protein is known per se.

Regarding the length (i.e., the number of amino acid residues) of an amino acid sequence extracted in this evaluation method, it is possible to extract an amino acid sequence of an optionally chosen length, as long as it is within the full-length of the above-described interaction region; however, it is preferable that an amino acid sequence consisting of 3-7 amino acid residues, more preferably an amino acid sequence consisting of four amino acid residues, is extracted. Extraction of amino acid sequence is conducted exhaustively. For example, when extracting an amino acid sequence consisting of X amino acid residues, N-X+1 amino acid sequences are extracted from the N-terminus to the C-terminus of the above-described interaction region (consisting of N amino acid residues), and stored in a fragmented peptide library. Although the length of amino acid sequence extracted may be unified, it may be variable. For example, it is possible to extract N—X+1 amino acid sequences each consisting of X amino acid residues from the interaction region exhaustively, extract N—X'+1 amino acid sequences each consisting of X' (a number differing from X) amino acid residues, with overlaps, from the same interaction region exhaustively, and store amino acid sequences of different lengths in a fragmented peptide library.

Additionally, an amino acid sequence selected by this evaluation method (fragmented peptide library) may be converted with an amino acid equivalent or dipeptide equivalent, with each amino acid or dipeptide in the amino acid sequence as 1 unit. Because an amino acid equivalent or dipeptide equivalent is similar in properties to a natural amino acid or dipeptide thereof, amino acid sequences containing these equivalents are of course considered to bind to target proteins.

Amino acid sequences (fragmented peptide library) selected by this evaluation method are preferably subjected to the second screening described below.

C. Amino Acid Position-Dependent Binding Significance Evaluation (Generation of Position Score Peptide Library)

Amino acid position-dependent binding significance evaluation is characterized in that a score matrix enabling a calculation of ΔG at high speed is constructed by deriving as low as several percents of amino acid sequences randomly from a peptide library containing as many as a thousand of to several hundreds of thousands of amino acid sequences, and evaluating the energy of their interaction with a target protein, and is used for peptide design. This evaluation method, provided that there are a plurality of proteins similar to each other in terms of substrate specificity, makes it possible to select one of these proteins as a target protein, and design a peptide highly specific for this target protein.

Although this evaluation method is applicable to an optionally chosen target protein, it is preferably applied to an enzyme etc. that have a pocket on the molecular surface thereof, and that are considered to undergo little structural changes associated with binding (e.g., peptidase) as a target protein. This is attributable to the fact that a score matrix is prepared on the basis of position-dependent amino acid prevalence. Hence, this evaluation method is preferred for target proteins that require a limited backbone and binding mode in binding with a peptide.

A "library for analysis" consists of a set of amino acid sequences extracted randomly from exhaustively generated amino acid sequences of a constant length (i.e., amino acid sequences consisting of a particular number of amino acid residues). The number of amino acid sequences contained in a library for analysis may be several percents to the total number of exhaustively generated amino acid sequences of a constant length. For example, when designing an amino acid sequence consisting of "n" natural amino acids (20 kinds), or when designing an amino acid sequence consisting of "n" amino acids ((20+M) kinds) containing not only natural amino acids (20 kinds) but also an optionally chosen number of amino acid equivalents (hereinafter assumed to be M kinds), $20^n$ or $(20+M)^n$ combinations are generated exhaustively, and several percents are selected randomly from among the generated $20^n$ or $(20+M)^n$ amino acid sequences and used as a library for analysis. Additionally, the number of amino acid sequences selected as a library for analysis is not limited to a particular number but can be set forth as appropriate. Although the length of amino acid sequences that can be designed in this evaluation is not subject to limitation, amino acid sequences consisting of 2-10 amino acid residues are preferable, and amino acid sequences consisting of 3-5 amino acid residues are more preferable. It is also possible to design, as a library for analysis, amino acid sequences containing an amino acid equivalent or dipeptide equivalent. Furthermore, it is also possible to design, as a library for analysis, amino acid sequences containing a β-amino acid or a γ-amino acid as necessary. To evaluate the appropriateness of "library for analysis", generation of "library for evaluation" is also conducted as necessary. Amino acid sequences as a "library for evaluation" are selected from among exhaustively generated amino acid sequences excluding the amino acid sequences used for a library for analysis. Although the number of amino acid sequences made available as a library for evaluation is not subject to limitation, it is set forth at a number smaller than the number of amino acid sequences made available as a library for analysis.

The definition of an "intermolecular energy parameter" is the same as that given in "II. Second screening" below, and its calculation is performed in the same manner as the method described below.

A "score matrix based on amino acid prevalence" means any matrix, as long as it has been generated on the basis of amino acid prevalence. An example of "score matrix based on amino acid prevalence" is the PSS matrix (Positional Scanning Score-MATRIX) generated according to [Equation 9] below. Note that $a_{ij}$ represents the prevalence of amino acid "i" at position "j" in all peptides contained in a library for analysis, and $b_{ij}$ is the prevalence of amino acid "i" at position "j" in the peptides lower than the threshold value ΔG contained in a library for analysis. In the above, the threshold value ΔG may be set forth in advance, or may be set forth by the method described below.

$$PSS_{ij} = \frac{b_{ij}}{a_{ij}} \times 100 \quad \text{[Equation 9]}$$

A "score based on amino acid prevalence" means a score calculated according to the above-described "score matrix based on amino acid prevalence", and is exemplified by PSS (Positional Scanning Score) calculated by [Equation 10] below (see, for example, Zhao, Y. et al., J. Immunol. 167, 2130-2141 (2001)). In [Equation 10] below, n represents the number of amino acid sequences to be determined, and $C_{ij}$ is a 20×n or (20+M)×n matrix, consisting of a value of 0 or 1. Additionally, a factor agreeing with amino acid "i" at position "j" in an optionally chosen amino acid sequence is written as 1, and a disagreeing factor is written as 0.

$$PSS = \sum_{i=1}^{20} \sum_{j=1}^{n} c_{ij} PSS_{ij} \quad \text{[Equation 10]}$$

(only natural amino acids taken into consideration) or $$PSS = \sum_{i=1}^{20+M} \sum_{j=1}^{n} c_{ij} PSS_{ij}$$

(natural amino acids and amino acid equivalents taken into consideration)

A "matrix based on an amino acid position-dependent intermolecular energy parameter" refers to a matrix obtained by converting a "score matrix based on amino acid prevalence" using the regression equation obtained by a correlation analysis between an "intermolecular energy parameter" calculated for each of the amino acid sequences extracted as a library for analysis and a "score based on amino acid prevalence". An example is the PSG matrix (Positional Scanning ΔG-MATRIX). When converting to a "score matrix based on amino acid prevalence", the constant term is preferably distributed to individual positions uniformly.

An "amino acid position-dependent intermolecular energy parameter value" is calculated by the above-described "score matrix based on amino acid prevalence" and exemplified by the PSG (Positional Scanning ΔG) calculated by the following equation [Equation 11]; a parameter having the same meaning as free energy can also be used. In [Equation 11] below, $PSG_{ij}$ represents the factors of ij in the PSG matrix.

$$PSG = \sum_{i=1}^{20} \sum_{j=1}^{n} c_{ij} PSG_{ij}$$

(only natural amino acids taken into consideration) or $$PSG = \sum_{i=1}^{20+M} \sum_{j=1}^{n} c_{ij} PSG_{ij}$$

(natural amino acids and amino acid equivalents taken into consideration)

[Equation 11]

Additionally, an amino acid sequence selected by this evaluation method (position score peptide library) may also be converted with an amino acid equivalent or dipeptide equivalent, with each amino acid or dipeptide in the amino acid sequence as 1 unit. Because an amino acid equivalent or dipeptide equivalent is similar in properties to a natural amino acid or dipeptide thereof, amino acid sequences containing these amino acid equivalents are of course considered to bind to target proteins.

Amino acid sequences selected by this evaluation method (position score peptide library) are preferably subjected to the second screening described below.

II. Second Screening

An "intermolecular energy parameter" refers to a parameter based on the intermolecular energy between a complementary amino acid sequence and a target site of target protein. An intermolecular energy parameter means a parameter concerning intermolecular energy calculated by an optionally chosen method commonly known in the art. As intermolecular energy parameters calculated by an optionally chosen method commonly known in the art, there may be mentioned, for example, those calculated by the MM3 force field (see, for example, Eisenberg D, et al., Proc. Natl. Acad. Sci. USA, 81, 140 (1984); Allinger N L, et al., J. Am. Chem. Soc., 99, 8127-8134 (1977)), Amber's force field (see, for example, Weiner S J, et al., J. Am. Chem. Soc., 106, 765-784 (1984)), or Charmm's force field (see, for example, Brooks B R, et al., J. Comput. Chem., 4, 187 (1983)). Preferably, as intermolecular energy parameters, intermolecular energy ($E_{mol}$) based on Amber's force field and an inhibition constant ($K_i$) are used.

"Intermolecular energy ($E_{mol}$)" is calculated by [Equation 12] below (Amber's force field (see, for example, Weiner S J, et al., J. Am. Chem. Soc., 106, 765-784 (1984); Wang J, et al., Proteins, 36, 1-19 (1999)) used).

$$E_{mol} = \sum_{bonds} k_r(r - r_{eq})^2 + \sum_{\substack{bond \\ angles}} k_\theta(\theta - \theta_{eq})^2 + \sum_{torsions} \frac{V_n}{2}(1 + \cos(nf - f_0)) + \sum_{i<j} \varepsilon_{ij}\left[\left(\frac{R_{ij}}{r_{ij}}\right)^{12} - \left(\frac{R_{ij}}{r_{ij}}\right)^6\right] + \sum_{i<j} \frac{q_i q_j}{\varepsilon(r_{ij})r_{ij}} + \sum_i \sigma_i A_s A_i$$ [Equation 12]

Here, $k_r$, $k_\theta$, and $V_n$ appearing in [Equation 12] are empirical parameters and are related to binding length, binding angle, and torsion angle, respectively. $\epsilon_{ij}$ and $R_{ij}$ are van der waals (VDW) parameters, $q_i$ is a charge, $r_{ij}$ is the distance between atoms "i" and "j", and $\epsilon(r_{ij})$ is the distance-dependent dielectric constant. Also, $\sigma_i A_s A_i$ is the solvent effect.

Here, preferably, the individual coefficients in [Equation 12] are given as empirical parameters by Amber's force field.

The "inhibition constant ($K_i$)" is calculated by [Equation 13] below.

$$\Delta G = RT \ln K_i$$ [Equation 13]

Where

R: gas constant ΔG: Gibbs' free energy

T: 298.2K $K_i$: inhibition strength

ΔG is attributable to complexation between a target site of target protein and a peptide candidate comprising a complementary amino acid sequence, and is calculated using an optionally chosen energy function commonly known in the art, and preferably calculated using the AutoDock energy function (see, for example, Morris, G. M., et al., J. Comp. Chem., 19, 1639-1662, (1998)).

A physiologically active peptide preferred for a target site of target protein is required to satisfy the threshold value requirements set forth for an optionally chosen intermolecular energy parameter. Preferably, when $E_{mol}$ or $K_i$ above is used as the intermolecular energy parameter, [Equation 14] or [Equation 15] below need to be satisfied.

if ($E_{mol} < E_{mol}^{thred}$)(thred: threshold value) [Equation 14]

then alteration and modification are conducted, followed by in vitro verification or if ($K_i < K_i^{thred}$)(thred: threshold value) [Equation 15]

then alteration and modification are conducted, followed by in vitro verification Where $E_{mol}^{thred}$ and $K_i^{thred}$ are optionally chosen threshold values.

First screening and second screening have been described above; a peptide having an amino acid sequence obtained by second screening is hereinafter also referred to as "lead peptide" for the sake of convenience.

III. Third Screening

For third screening, a variation of lead peptide may be conducted by "amino acid variation ΔE (e.g., ΔG) evaluation". Amino acid variation ΔE evaluation refers to a method of replacing each of the amino acids constituting a lead peptide with another natural amino acid or amino acid equivalent to prepare a variant peptide, calculating a $\Delta E_{mutant}$ (e.g., $\Delta G_{mutant}$) of this variant peptide and a target protein, and evaluating the variant peptide. For example, when a peptide obtained in second screening consists of four amino acid residues, of which only one amino acid residue is to be replaced with another natural amino acid, 4×19 variant peptides are generated exhaustively, or when it is to be replaced with another natural amino acid or amino acid equivalent, 4×(19+M) variant peptides are generated exhaustively, and a $\Delta E_{mutant}$ (e.g., $\Delta G_{mutant}$) of each of these variant peptides and a target protein is calculated. Although a calculation of a $\Delta E_{mutant}$ (e.g., $\Delta G_{mutant}$), like the calculation in second screening, is made using an optionally chosen energy function commonly known in the art, it is preferably calculated using the AutoDock energy function. In an example, when using binding free energy as ΔE, the difference ΔΔG between the $\Delta G_{mutant}$ obtained for each variant peptide and the $\Delta G_{lead}$ of the lead peptide is calculated by [Equation 16] below.

$$\Delta\Delta G = \Delta G_{mutant} - \Delta G_{lead}$$ [Equation 16]

From the equation above, it is understood that a variant peptide for a negative ΔΔG forms a stabler complex with a target protein, compared to the lead peptide, and that a variant peptide for a positive ΔΔG forms a more unstable complex with a target protein, compared to the lead peptide. Therefore, in third screening, it is preferable to introduce an amino acid variation resulting in a negative ΔΔG. In the exemplification above, only one amino acid residue out of the amino acid residues constituting the lead peptide is replaced; however, two or three amino acid residues may be replaced using a combination of amino acid variations resulting in a negative ΔΔG. By conducting third screening as described above, a more optimized physiologically active peptide can be designed.

In amino acid substitution, each amino acid in the lead peptide may be replaced with 19 other kinds of natural amino acids. In addition to natural amino acids, it may be replaced with amino acid equivalents (e.g., optionally chosen non-natural α-amino acids) and non-natural amino acids such as β-amino acids and γ-amino acids. However, because substitution with an alternative to an α-amino acid is highly likely to result in a change in the configuration of the primary chain, substitution with an optionally chosen non-natural α-amino acid is preferred. Additionally, each amino acid in the lead peptide may be replaced with an amino acid of any of the L-configuration and the D-configuration.

This amino acid substitution can also be viewed from the viewpoint of "amino acid side chain optimization". For example, assume that the above-described "amino acid variation ΔE (e.g., ΔG) evaluation" has been conducted via first screening and second screening to yield Ala-Cys-Phe-Val, the most preferable peptide for a target site of a target protein. In this case, it is also possible to re-verify the side chain of each of the amino acids constituting this peptide, in order to obtain a more preferable peptide on the basis of this peptide Ala-Cys-Phe-Val. Specifically, it is also possible to conduct the above-described "amino acid variation $\Delta E$ (e.g., $\Delta G$) evaluation" and obtain a more optimized variant peptide, for a side chain with a halogen atom introduced in place of a hydrogen atom in the side chain of Met ($—CH_2CH_2SCH_3$) or a side chain with an additional group introduced. Although variations of the side chain of Met have been described for exemplification above, it is of course possible to re-verify the side chain of a natural amino acid other than Met, and the side chain of a non-natural amino acid (preferably a non-natural α-amino acid) in the same manner. Generally speaking, in the case of a protein of somewhat large size, amino acid substitution is likely to be limited to natural amino acids. This is because it is necessary to alter the DNA encoding region and synthesize a variant (substituted) protein by translation with a cell system or a cell-free system when such a protein is to be synthesized actually. However, in the case of a low-molecular peptide, the kinds of amino acids that constitute the peptide are not limited to natural amino acids. This is because a low-molecular peptide can easily be synthesized by solid phase synthesis, and also because its polymerization reaction is easy, provided that the starting material amino acid is available, whether it is a natural amino acid or a non-natural amino acid. Therefore, third screening involving "amino acid variation $\Delta E$ (e.g., $\Delta G$) evaluation" makes it possible to more optimize the side chain of amino acid and obtain a physiologically active peptide of higher specificity.

It should be noted that the particular equations mentioned in "I. First screening", "II. Second screening", and "III. Third screening" are given for the sake of exemplification, and it should be understood that the equations having the same definitions as those thereof and the equations derived therefrom are all useful in respective calculations in the present invention.

The present invention is described in detail below.

The method of the present invention may be any method, as long as it has the steps of (a1)-(g1) above, as shown in (1) above, and may be any method, as long as it has the steps of (a1')-(i1') above, as shown in (5) above.

Although these specific means and modes for embodying the method according to the present invention are not subject to limitation, the best mode of embodiment is the computer processing using the programs according to the present invention, mentioned in (9)-(12) above and (13)-(16) above, in view of the vast amount of data to be processed. The processing steps included in the programs according to the present invention are equivalent to the technical concepts of the individual steps of the method according to the present invention. For this reason, by describing in detail the programs according to the present invention below, the method according to the present invention is described at the same time.

The programs of the present invention can be roughly divided into two sets from the viewpoint of designing a physiologically active peptide that interacts with a target amino acid sequence, and designing a physiologically active peptide that interacts with a target protein (i.e., designing a physiologically active peptide considering not only the interaction with a target amino acid sequence but also the interaction with another amino acid sequence present in a target site of target protein). One of the two sets consists of the programs shown in (9)-(12) above, which are intended to design a physiologically active peptide that interacts with a target amino acid sequence. In particular, the steps of (a1)-(f1) above included in the program of (9) above may also be called "first screening".

The other set of the programs according to the present invention consists of the programs shown in (13)-(16) above, which are intended to design a physiologically active peptide that interacts with a target protein. In particular, the steps of (a1')-(f1') above included in (13) above may also be called "first screening", and the steps of (g1')-(i1') above may also be called "second screening". By combining "first screening" and "second screening" as such, it is possible to obtain a more appropriate physiologically active peptide for a target site of target protein.

Furthermore, the programs of (13)-(16) above may be combined with the steps of (I)-(III) above included in (24) above. These steps of (I)-(III) above may also be called "third screening". By further combining "third screening" with "first screening" and "second screening", it is possible to obtain a physiologically active peptide of higher specificity for a target site of target protein.

In another aspect, the present invention provides the programs of (25) and (26) above. The steps of (a2)-(b2) above included in the program of (25) above may also be called "first screening". Also, the steps of (a2')-(b2') above included in the program of (26) above may be called "first screening", and the steps of (c2')-(e2') above may be called "second screening". The program of (26) above may be combined with the steps of (I)-(III) above included in (27) above ("third screening").

In still another aspect, the present invention provides the programs of (28) and (29) above. The steps of (a3)-(h3) above included in the program of (28) above may also be called "first screening". Also, the steps of (a3')-(h3') above included in the program of (29) above may be called "first screening", and the steps of (i2')-(k2') above may be called "second screening". The program of (29) above may be combined with the steps of (I)-(III) above included in (30) above ("third screening").

Figure 2:
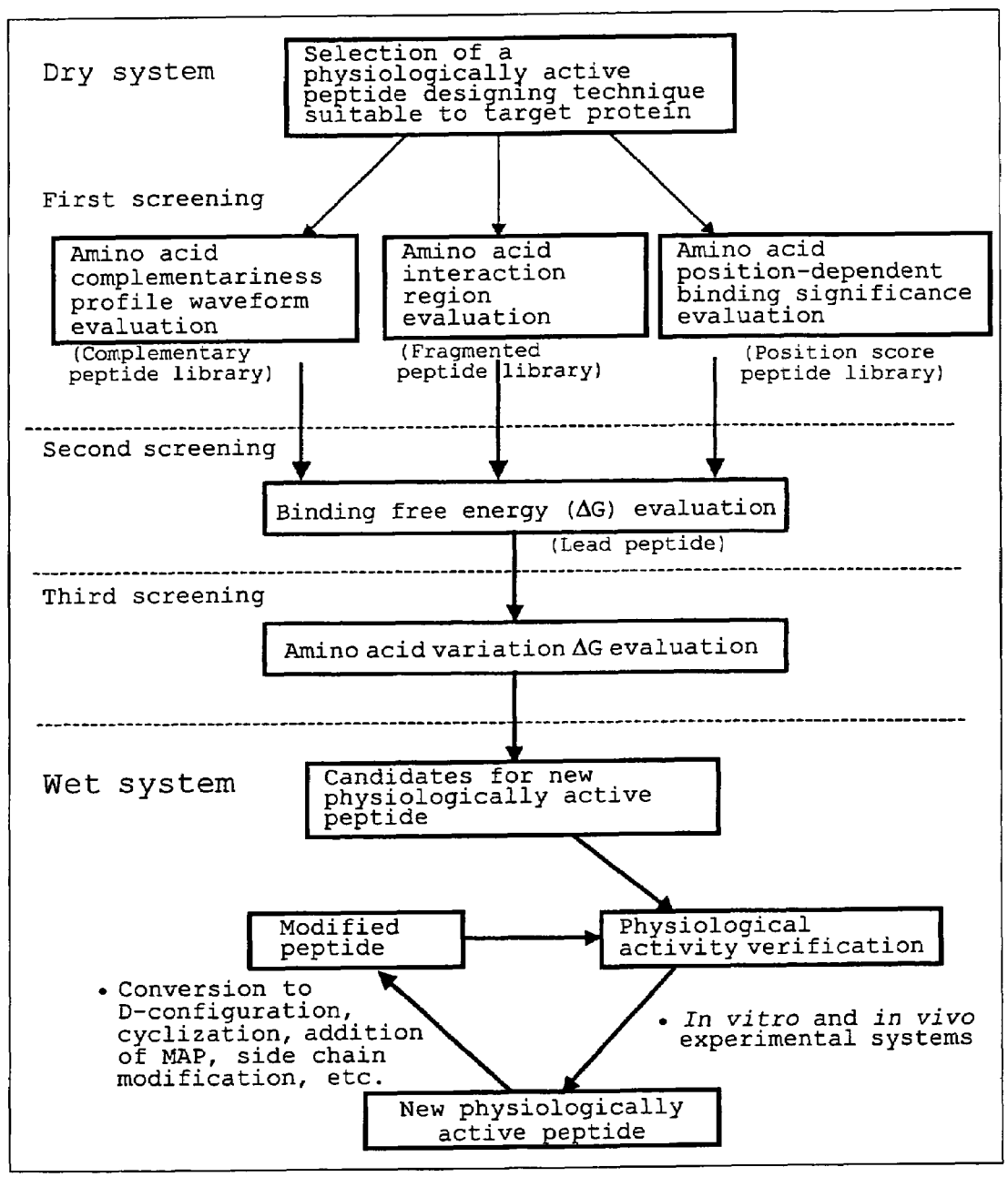
FIG. 2 shows the entire system of the present invention in designing a physiologically active peptide.

An example of designing a physiologically active peptide in the present invention is shown in FIG. 1, and the entire system of the present invention is shown in FIG. 2. FIG. 1 and FIG. 2 depict second screening; this second screening is conducted as necessary and may be used in combination with the third screening depicted in FIG. 2.

In the present invention, first screening involves three kinds of programs, which are selectively used according to target protein nature etc. On the other hand, second screening involves a single program common to all processes thereof, and third screening also involves a single program common to all processes thereof. First, selection for first screening is described.

Figure 3:
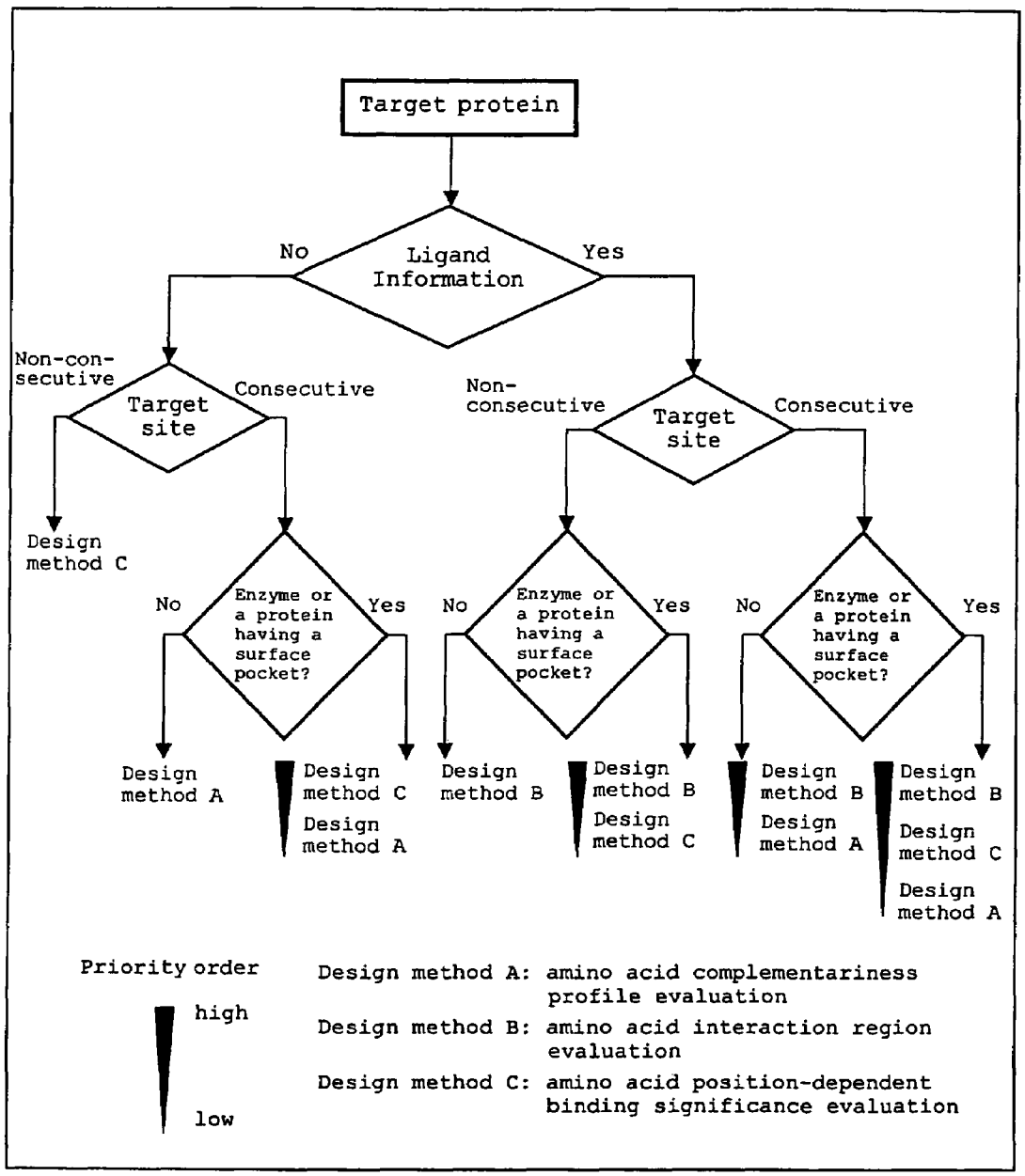
FIG. 3 shows a flow chart of a program used for selection in first screening.

FIG. 3 is a flow chart showing a program flow in selection for first screening. Regarding the kind of first screening, the most appropriate can be selected by the three judgment criteria of the availability of ligand information, the consecutiveness/non-consecutiveness of target site, and whether or not an enzyme or a surface pocket is present. Selection for first screening is described in detail below with reference to steps 501-506 of FIG. 3.

Step 501 of FIG. 3 is a step for determining whether or not a peptide serving as a ligand for a target protein is present. Hence, if the ligand for a target protein is unknown, progress to step 502 of FIG. 3 is made; if the ligand is known, progress to step 504 of FIG. 3 is made.

Step 502 of FIG. 3 is a step for determining whether or not a target site of target protein consists mainly of a consecutive amino acid sequence. If the target site of target protein has been elucidated by, for example, an analysis of crystalline structure, the determination is made on the basis of that information. If the target site of target protein is unknown, the determination is made by, for example, a steric structure prediction program commonly known in the art. As a result, if the target site of target protein consists of a non-consecutive amino acid sequence, amino acid position-dependent binding significance evaluation is conducted for first screening. On the other hand, if the target site of target protein consists mainly of a consecutive amino acid sequence, progress to step 503 of FIG. 3 is made.

Step 503 of FIG. 3 is a step for determining whether the target protein is an enzyme or not, or whether or not the target protein is a protein having a pocket on the surface thereof. As proteins having a pocket on the surface thereof, there may be mentioned, for example, receptors. Additionally, if the kind of target protein (e.g., enzyme, receptor, etc.) is unknown, the kind of the target protein can be predicted by, for example, homology search. If the target protein is determined to be neither an enzyme nor a protein having a pocket on the surface thereof in step 503 of FIG. 3, amino acid complementariness profile waveform evaluation is used for first screening. On the other hand, if the target protein is determined to be either an enzyme or a protein having a pocket on the surface thereof, amino acid complementariness profile waveform evaluation or amino acid position-dependent binding significance evaluation is used for first screening, with preference given to amino acid position-dependent binding significance evaluation.

Step 504 of FIG. 3 is a step for determining whether or not a target site of target protein consists mainly of a consecutive amino acid sequence. In step 504 of FIG. 3, the determination is made in the same manner as step 502 of FIG. 3. As a result, if a target site of target protein is determined to consist of a non-consecutive amino acid sequence, progress to step 505 of FIG. 3 is made. On the other hand, if a target site of target protein is determined to consist mainly of a consecutive amino acid sequence, progress to step 506 of FIG. 3 is made.

Step 505 of FIG. 3 is a step for determining whether or not the target protein is an enzyme, or whether or not the target protein is a protein having a pocket on the surface thereof. In step 505 of FIG. 3, the determination is made in the same manner as step 503 of FIG. 3. If the target protein is determined to be neither an enzyme nor a protein having a pocket on the surface thereof, amino acid interaction region evaluation is used for first screening. On the other hand, if the target protein is determined to be either an enzyme or a protein having a pocket on the surface thereof, amino acid interaction region evaluation or amino acid position-dependent binding significance evaluation is used for first screening, with preference given to amino acid interaction region evaluation.

Step 506 of FIG. 3 is a step for determining whether or not the target protein is an enzyme, or whether or not the target protein is a protein having a pocket on the surface thereof. In step 506 of FIG. 3, the determination is made in the same manner as step 503 of FIG. 3. If the target protein is determined to be neither an enzyme nor a protein having a pocket on the surface thereof, amino acid complementariness profile waveform evaluation or amino acid interaction region evaluation is used for first screening, with preference given to amino acid interaction region evaluation. On the other hand, if the target protein is determined to be either an enzyme or a protein having a pocket on the surface thereof, any of amino acid complementariness profile waveform evaluation, amino acid interaction region evaluation or amino acid position-dependent binding significance evaluation may be used for first screening, with preference given to amino acid interaction region evaluation or amino acid position-dependent binding significance evaluation, with greater preference given to amino acid interaction region evaluation.

First screening is described below with reference to steps 101-111 of FIG. 4 (amino acid complementariness profile waveform evaluation), steps 301-302 of FIG. 6 (amino acid interaction region evaluation) and steps 401-408 of FIG. 8 (amino acid position-dependent binding significance evaluation). Second screening is described with reference to step 112 and subsequent steps of FIG. 4. Third screening is described with reference to steps 201-204 of FIG. 5.

Figure 4:
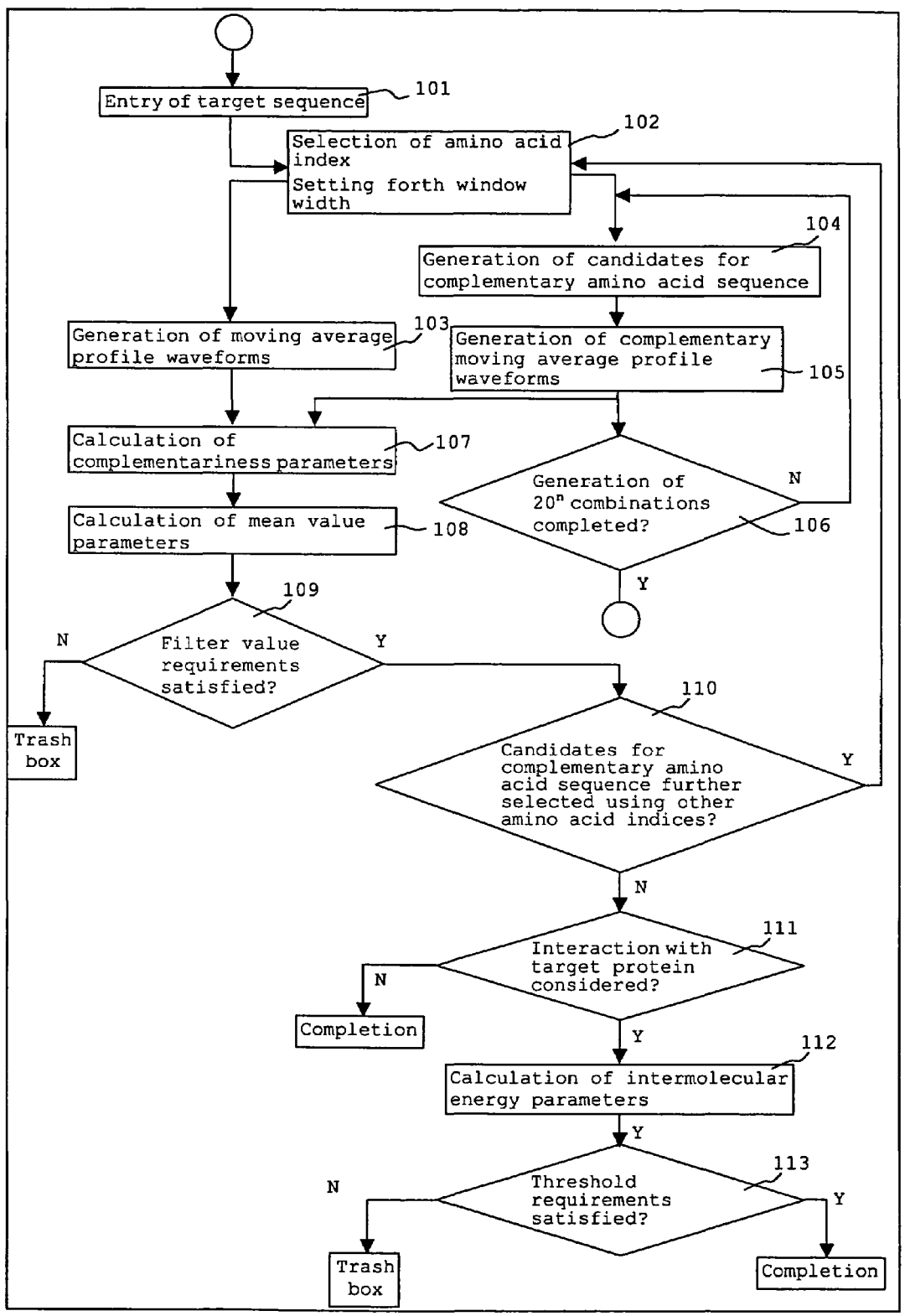
FIG. 4 shows a flow chart of a program used to design a physiologically active peptide. This flow chart corresponds to an amino acid complementariness profile waveform evaluation as first screening, followed by second screening.

FIG. 4 is a flow chart showing the program flows of (9) and (13) above. First, the program of (9) above is described in detail below.

The above-described step (a1) corresponds to step 101 in the flow chart of FIG. 4. As data entry means, there may be mentioned, for example, touch panels, keyboards, mice, etc. As other data entry means, there may be used pen tablets, voice input systems, etc. As the target amino acid sequence to be entered, the amino acid sequence of a ligand-binding site, a substrate-binding site, a protein-to-protein interaction site, etc. is selected as appropriate. Those skilled in the art are able to select a target amino acid sequence as appropriate on the basis of X-ray analysis data on a protein, or on the basis of the steric structure of a protein predicted using a common protein steric structure prediction program etc., and to enter the sequence data thereof. Additionally, an amino acid sequence set forth virtually, rather than by a technique as described above, (i.e., an optionally chosen amino acid sequence) may be used as a target amino acid sequence for data entry.

Although the program of (9) above does not include a step corresponding to step 102 shown in the flow chart of FIG. 4, it may include a step corresponding to step 102 of FIG. 4 as necessary. In step 102 of FIG. 4, an entry of one or more amino acid indices and window width is possible, and, although it is not specified, an entry of a filter value of complementariness parameter (e.g., correlation coefficient filter value $R_t$), $P_{ave}$ filter values "a" and "b", a threshold value of intermolecular energy parameter (e.g., $$E_{mol}^{thred}, Ki^{thred}$$ [Equation 17]

), etc. can also be accepted. The data entry means used may be the same as the data entry means used in step 101 of FIG. 4. These parameters may be selected and entered by the user at each time of operation, or may be set forth in advance and, if desired, may be changed by the user.

The above-described step (b1) corresponds to step 103 of FIG. 4. In the above-described step (b1), one or more profile waveforms are generated from the target amino acid sequence data entered in step 101 of FIG. 4 in accordance with one or more amino acid indices set forth in step 102 of FIG. 4, and are then converted to one or more moving average profile waveforms (step 103 of FIG. 4). Specifically, for the obtained target amino acid sequence, the computing process shown by [Equation 1] above is executed. The data on one or more moving average profile waveforms for the target amino acid sequence is transferred to step 107 of FIG. 4.

The above-described step (c1) corresponds to step 104 and step 105 of FIG. 4. In the above-described step (c1), a candidate for complementary amino acid sequence is generated (step 104 of FIG. 4); for the generated complementary amino acid sequence, one or more profile waveforms are generated according to the one or more amino acid indices set forth in 102 of FIG. 4 and then converted to one or more complementary moving average profile waveforms (step 105 of FIG. 4). Specifically, for the obtained candidate for complementary amino acid sequence, the computing process shown by

[Equation 2] above is executed. The data on one or more complementary moving average profile waveforms for the candidate for complementary amino acid sequence is transferred to step 107 of FIG. 4 for calculation of complementariness parameter.

Although the program of (9) above does not include a step corresponding to step 106 of FIG. 4, it may include a step corresponding to step 106 of FIG. 4 as necessary. When the number of amino acid residues of target amino acid sequence is n, step 106 of FIG. 4 directs that step 104 and step 105 of FIG. 4 should be repeated until $20^n$ (only natural amino acids taken into consideration) or $(20+M)^n$ (natural amino acids and amino acid equivalents taken into consideration; the number of amino acid equivalents to be considered written as M; the same applies below) candidates for complementary amino acid sequence are generated and each thereof is converted to one or more complementary moving average profile waveforms. If $20^n$ or $(20+M)^n$ candidates for complementary amino acid sequence have been generated and each thereof has been converted to one or more complementary moving average profile waveforms, the generation of candidates for complementary amino acid sequence (step 104 of FIG. 4) and hence the generation of complementary moving average profile waveforms (step 105 of FIG. 4) are completed.

The above-described step (d1) corresponds to step 107 of FIG. 4. In the above-described step (d1), one or more complementariness parameters (e.g., correlation coefficient shown by [Equation 3]) from the same amino acid index are each calculated between one or more moving average profile waveforms for target amino acid sequence and one or more complementary moving average profile waveforms of a candidate for complementary amino acid sequence (step 107 of FIG. 4).

For example, if only one amino acid index has been used in converting a target amino acid sequence to a moving average profile waveform and a complementary amino acid sequence to a complementary moving average profile waveform, only one complementariness parameter is calculated in step 107 of FIG. 4.

If two or more amino acid indices have been used in converting a target amino acid sequence to a moving average profile waveform and a complementary amino acid sequence to a complementary moving average profile waveform, two or more complementariness parameters are calculated in step 107 of FIG. 4.

Although the program of (9) above does not include a step corresponding to step 108 of FIG. 4, it may include a step corresponding to step 108 of FIG. 4 as necessary. In step 108 of FIG. 4, one or more mean value parameters are calculated on the basis of one or more amino acid indices used.

The above-described step (e1) is not specifically shown in FIG. 4. However, the above-described step (e1) may be included between step 108 and step 109 of FIG. 4. In the above-described step (e1), a candidate for complementary amino acid sequence, along with one or more complementariness parameters calculated in step 107 of FIG. 4 (one or more mean value parameters calculated in step 108 of FIG. 4 as necessary), is stored in a storage.

The above-described step (f1) corresponds to step 109 of FIG. 4. In the above-described step (f1), a candidate for complementary amino acid sequence is extracted on the basis of one or more complementariness parameters calculated in step 107 of FIG. 4 (one or more mean value parameters calculated in step 108 of FIG. 4 as necessary). Extraction is conducted on the basis of filter value requirements. The filter value may be selected and entered by the user at each time of operation, or may be set forth in advance and, if desired, may be changed by the user.

When only one complementariness parameter is calculated between a target amino acid sequence and a complementary amino acid sequence in the above-described step (d1), a candidate for complementary amino acid sequence is extracted in the above-described step (f1) so that the filter value requirements for that complementariness parameter. In this extraction processing, the filter value of one mean value parameter may be used in combination.

When two or more complementariness parameters are calculated between a target amino acid sequence and a complementary amino acid sequence in the above-described step (d1), a candidate for complementary amino acid sequence is extracted, with two or more complementariness parameters considered comprehensively, in the above-described step (f1). In this extraction processing, two or more mean value parameters may be used in combination with comprehensive consideration. Those skilled in the art are able to set forth requirements, so as to extract a desired candidate for complementary amino acid sequence, with preferential consideration of an emphasized parameter, provided that two or more complementariness parameters (two or more mean value parameter, as necessary) have been calculated.

Although the above-described program (9) does not include a step corresponding to step 110 of FIG. 4, it may include a step corresponding to step 110 of FIG. 4 as necessary. In step 110 of FIG. 4, a determination is made as to whether or not to further select a candidate for complementary amino acid sequence using another amino acid index. Specifically, for the candidate for complementary amino acid sequence extracted in the above-described step (f1), it is determined whether or not to repeat the above-described steps (b1)-(f1) once or more in accordance with an amino acid index set forth in step 102 of FIG. 4 (differing from the previous amino acid index). Whether or not to repeat the above-described steps (b1)-(f1) once or more, the number of repeats, and the one or more amino acid indices used during that process may be selected and entered by the user at each time of operation, or may be set forth in advance and, if desired, may be changed by the user.

If it is determined unnecessary to further select a candidate for complementary amino acid sequence using another amino acid index in step 110 of FIG. 4, progress to step 111 of FIG. 4 is made and it is determined whether or not to consider the interaction with target protein. The above-described program (9) is intended to consider the interaction with target amino acid sequence and is a mode of embodiment wherein the interaction with the target protein itself is not considered, it is always judged N in step 111 of FIG. 4.

Although the above-described step (g1) is not shown in FIG. 4, it may be included after N of step 111 of FIG. 4. The above-described step (g1) displays a candidate for an amino acid sequence complementary to target amino acid sequence, along with a complementariness parameter thereof etc. As display means, there may be used ordinary display apparatuses, printers, etc. Preferably, the extracted candidates for complementary amino acid sequence are displayed in the descending order with a ranking for each parameter, or in the descending order with the individual parameters considered comprehensively.

Next, the program of (13) above is described in detail below. This program takes into consideration the interaction with a target site of target protein, as well as the interaction with a target amino acid sequence.

The above-described steps (a1')-(f1') of the program of (13) above correspond to steps (a1)-(f1) of the program of (9) above. Therefore, steps (a1')-(f1') of the program of (13) above are taken in the same manner as steps (a1)-(f1) of the program of (9) above. However, in step 102 of FIG. 4, an entry of data on target protein (e.g., target protein amino acid sequence data, data on target protein target site, etc.) is possible. Because the above-described program (13) is a mode of embodiment wherein the interaction with the target protein itself is considered, it is always judged Y in step 111 of FIG. 4.

The above-described step (g1') corresponds to step 112 of FIG. 4. In step (g1'), an intermolecular energy parameter between a target site of target protein and a candidate for complementary amino acid sequence is calculated. This calculation is executed using the data on target protein entered in step 102 of FIG. 4 (e.g., target protein amino acid sequence data, target protein target site data, etc.), sequence data on a candidate for complementary amino acid sequence, etc.

Although the above-described step (h1') is not shown in FIG. 4, it may be included between step 112 and step 113 of FIG. 4. In the above-described step (h1'), a candidate for complementary amino acid sequence, along with the intermolecular energy parameter calculated in step 112 of FIG. 4, is stored in a storage.

The above-described step (i1') corresponds to step 113 of FIG. 4. In the above-described step (i1'), a candidate for complementary amino acid sequence that satisfies the threshold requirements of intermolecular energy parameter is extracted on the basis of information stored in a storage.

Although the above-described step (j1') is not shown in FIG. 4, it may be included after Y of step 113 of FIG. 4. In the above-described step (j1'), a candidate for an amino acid sequence complementary to target amino acid sequence is displayed, along with a complementariness parameter thereof etc. As display means, there may be used ordinary display apparatuses, printers, etc. Preferably, the extracted complementary amino acid sequences are displayed with a rank based on a good intermolecular energy parameter.

Additionally, the above-described steps (I)-(III) may be included between the above-described step (i1') and step (j1'). The above-described steps (I)-(III) correspond to steps 201-203 of FIG. 5, respectively. The above-described steps (I)-(III) are described in detail below.

Figure 5:
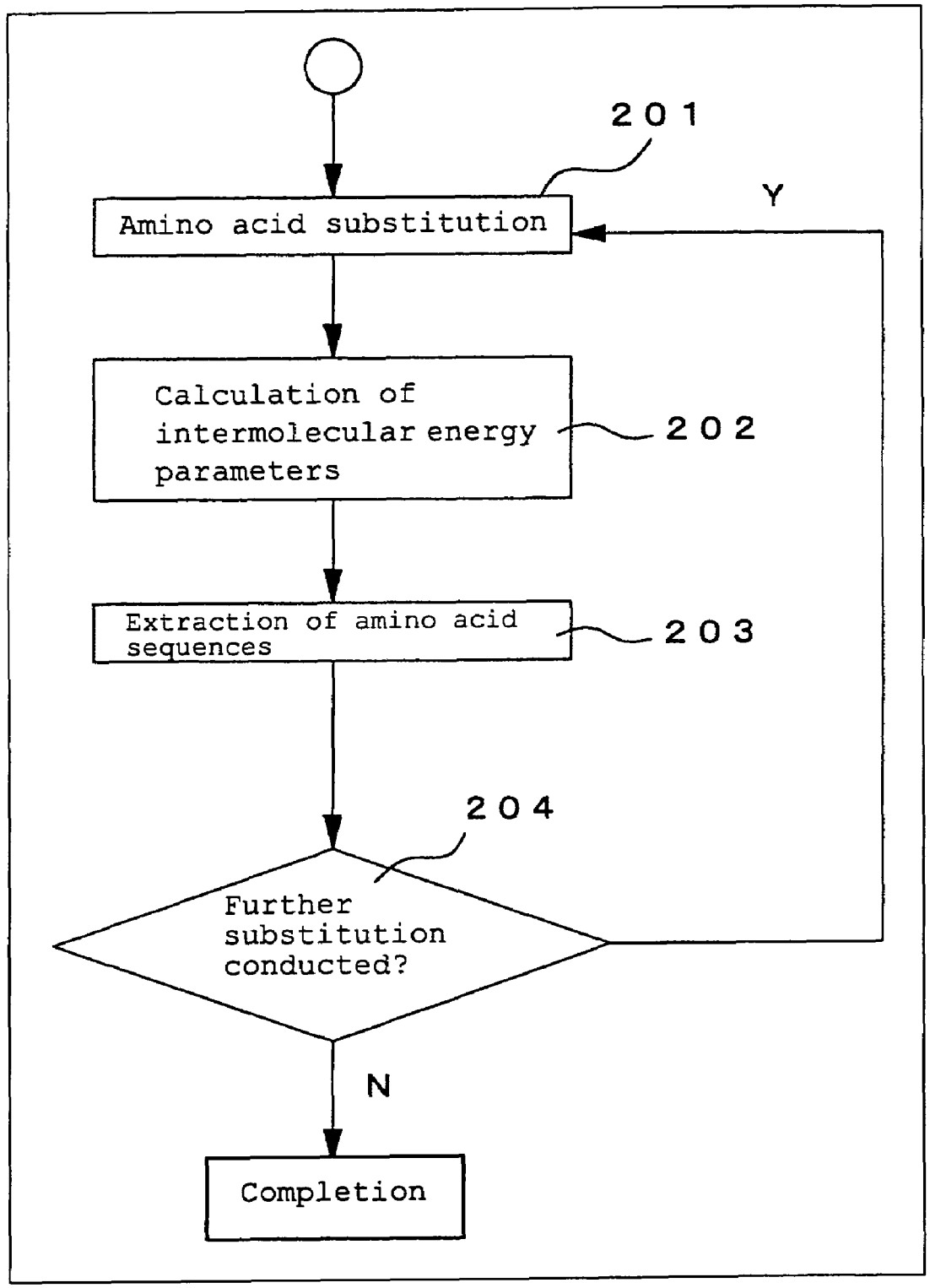
FIG. 5 shows a flow chart of a program for third screening in designing a physiologically active peptide.

The above-described step (I) corresponds to step 201 of FIG. 5. In the above-described step (I), an amino acid sequence with an amino acid variation introduced to an amino acid sequence extracted in the above-described step (i1') is generated. If one amino acid is replaced in an amino acid sequence extracted in the above-described step (i1'), amino acid sequences replaced with 19 kinds of natural amino acids other than the original amino acid are generated exhaustively. Also, in an amino acid sequence extracted in the above-described step (i1'), a plurality (two or three or more) of amino acids are replaced, and these amino acid sequences are generated exhaustively (e.g., if two amino acids are replaced with other natural amino acids, 19×19 amino acid sequences are generated). Furthermore, not only natural amino acids but also non-natural amino acid sequences can be used for amino acid substitution. The data on these amino acids may be in a form wherein data stored in advance is utilized, or may be in a form wherein necessary data is retrieved with reference to an external database.

The above-described step (II) corresponds to step 202 of FIG. 5. In the above-described step (II), an intermolecular energy parameter between each of all amino acid sequences generated in the above-described step (I) and a target site of target protein is calculated. This calculation is conducted in the same manner as the above-described step (g1').

The above-described step (III) corresponds to step 203 of FIG. 5. In the above-described step (III), the intermolecular energy parameter calculated in the above-described step (II) is compared with the intermolecular energy parameter between an amino acid sequence extracted in the above-described step (i1') and a target site of target protein as a control, and an amino acid sequence having an intermolecular energy parameter that is stabler than the intermolecular energy parameter of the control is selected. As an intermolecular energy parameter between an amino acid sequence extracted in the above-described step (i1') and a target site of target protein, there may be used a value calculated in step (g1'). As a result of the comparison, an amino acid sequence having an intermolecular energy parameter that is stabler than the intermolecular energy parameter of the control is extracted.

After the above-described step (III), step 204 of FIG. 5 may be included. In step 204 of FIG. 5, it is determined whether to repeat the above-described steps (I)-(III) for the amino acid sequence extracted in the above-described step (III). If it is determined unnecessary to repeat the above-described steps (I)-(III) in step 204 of FIG. 5, extraction of amino acid sequence is completed and progress to the above-described step (j1') is made. However, after step 204 of FIG. 5, a step for optimizing each amino acid side chain may be provided. In such cases, progress to the above-described step (j1') is made after completion of the step for optimizing each amino acid side chain.

Figure 6:
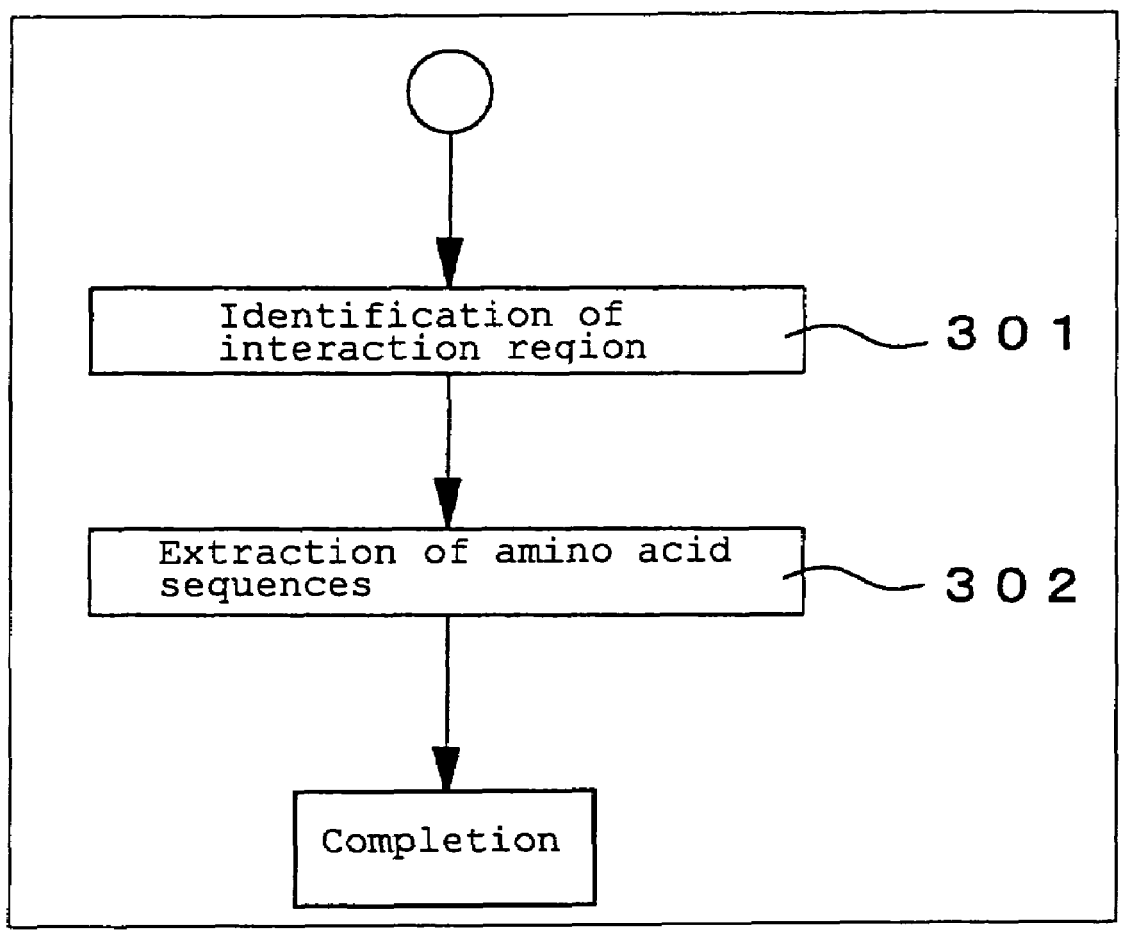
FIG. 6 shows a flow chart of a program for amino acid interaction region evaluation (first screening).

FIG. 6 is a flow chart showing program flows of (25) above and a portion of (26) above. This program is especially useful if the primary structure (amino acid sequence) of a protein that interacts, or is expected to interact, with a target protein, is known. First, the program of (25) above is described in detail below.

The above-described step (a2) in the program of (25) above corresponds to step 301 of FIG. 6. In the above-described step (a2), an interaction region in a protein that interacts with a target site of target protein is identified. If a protein with an already identified region capable of interacting with a target protein is present, that region is selected. If a plurality of interaction regions are present in a single protein, the plurality of regions are selected as interaction regions. A plurality of proteins are known to be capable of interacting with a target protein, it is also possible to select a plurality of interaction regions from each of these proteins. On the other hand, if the protein itself that interacts with a target protein is known but the interaction region has not been identified, this region can be selected by a method obvious in the art (e.g., RBD method (see, for example, Gallet X. et al, J. Mol. Biol., 302, 917-926 (2000))).

Figure 7:
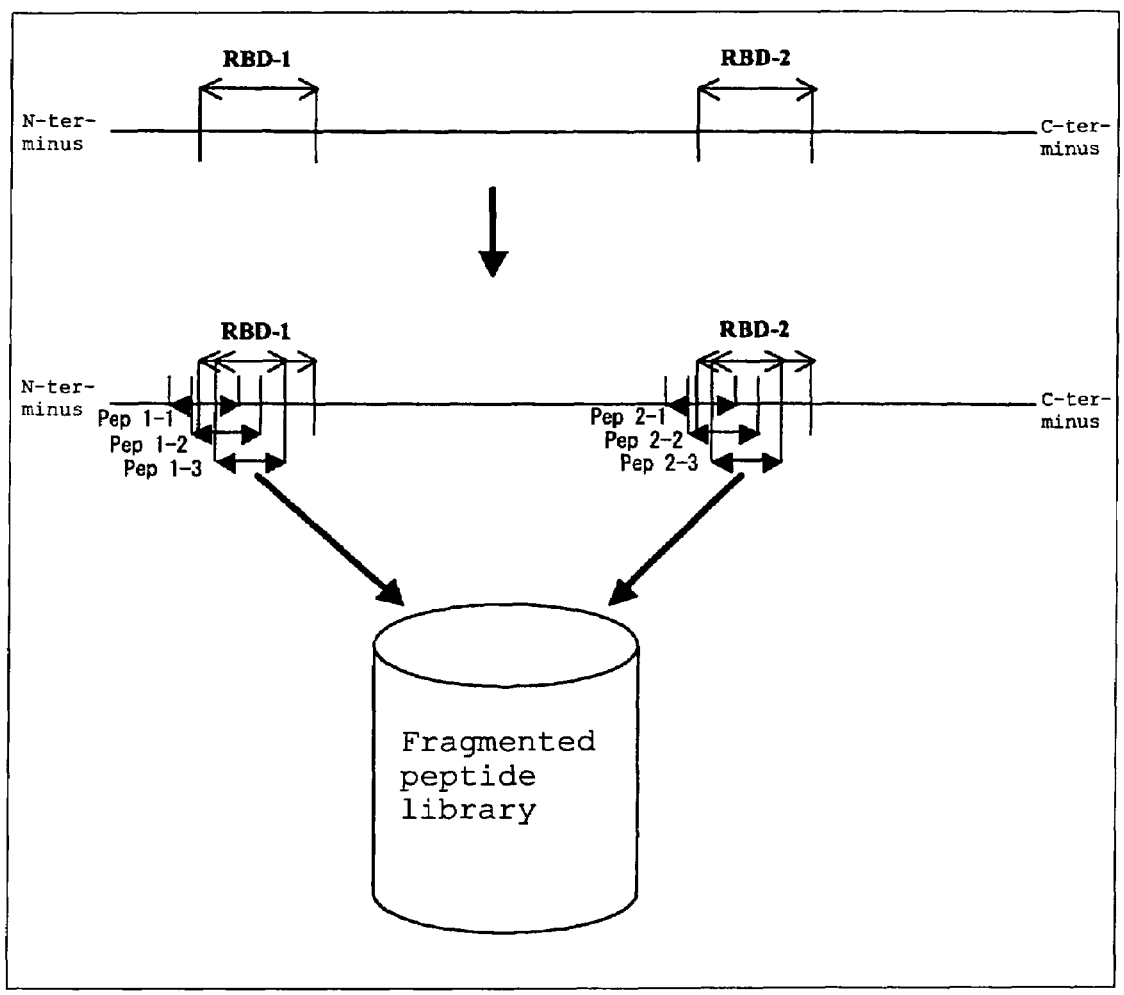
FIG. 7 shows the extraction of a fragmented peptide from an amino acid sequence of a ligand (protein).

The above-described step (b2) corresponds to step 302 of FIG. 6. In the above-described step (b2), an amino acid sequence of optionally chosen length is extracted from the interaction region. A summary of amino acid sequence extraction executed in the above-described step (b2) is shown in FIG. 7. Regarding the length (i.e., the number of amino acid residues) of the amino acid sequence extracted in the above-described step (b2), as long as it is within the full-length of the above-described interaction region, it is possible to extract an amino acid sequence of optionally chosen length. Extraction of amino acid sequences is conducted exhaustively. For example, if an amino acid sequence consisting of X amino acid residues is to be extracted, N—X+1 amino acid sequences are extracted from the N-terminus to the C-terminus of the above-described interaction region. Also, although the extracted amino acid sequences may be unified in terms of length, amino acid sequences of different lengths may also be extracted exhaustively.

Next, the program of (26) above is described in detail below.

The above-described steps (a2')-(b2') of the program of (26) above correspond to the above-described steps (a2)-(b2) of the program of (25) above. Therefore, the above-described steps (a2')-(b2') of the program of (26) above are conducted in the same manner as the above-described steps (a2)-(b2) of the program of (25) above.

The above-described steps (c2')-(f2') of the program of (26) above correspond to the above-described steps (g1')-(j1') of the program of (13) above. Therefore, the above-described steps (c2')-(f2') of the program of (26) above are conducted in the same manner as the above-described steps (g1')-(j1') of the program of (13) above.

The above-described steps (I)-(III) may be included between the above-described step (e2') and step (f2'). The above-described steps (I)-(III) are conducted in the same manner as described above.

Figure 8:
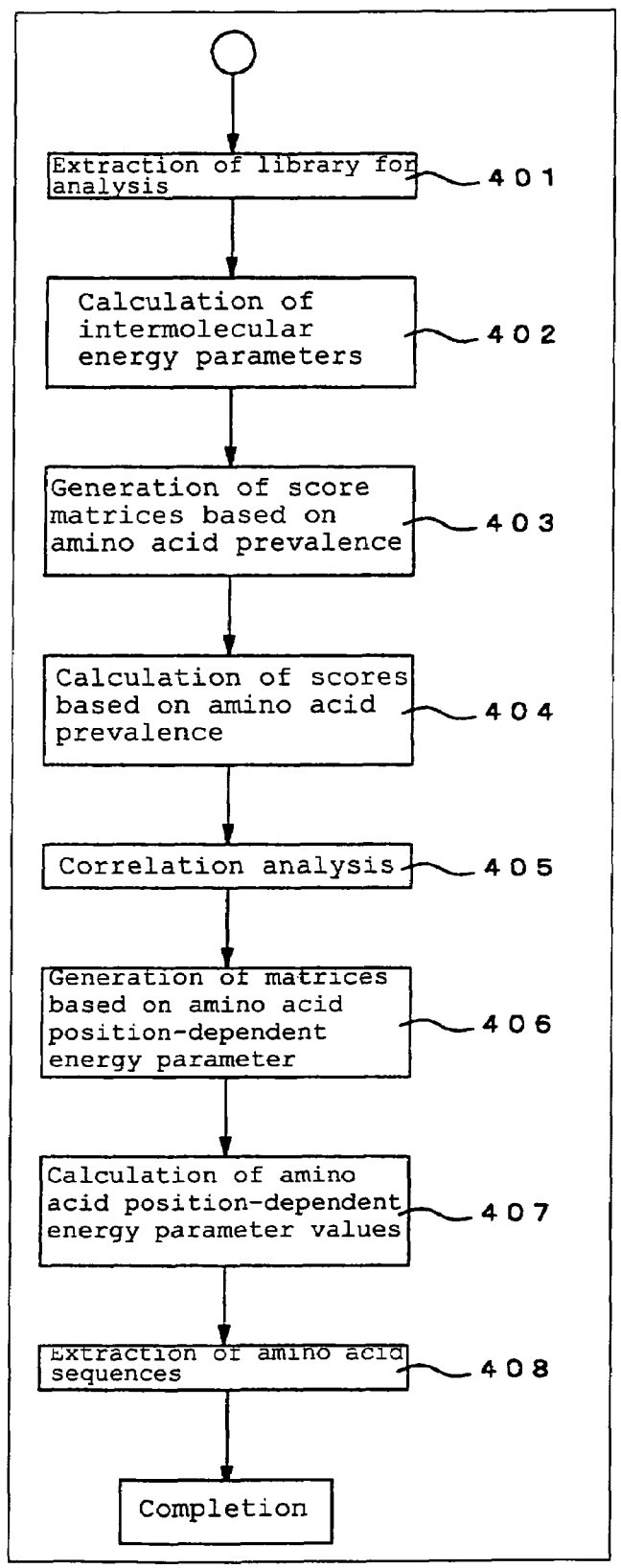
FIG. 8 shows a flow chart of a program for amino acid position-dependent binding significance evaluation (first screening).
Figure 9:
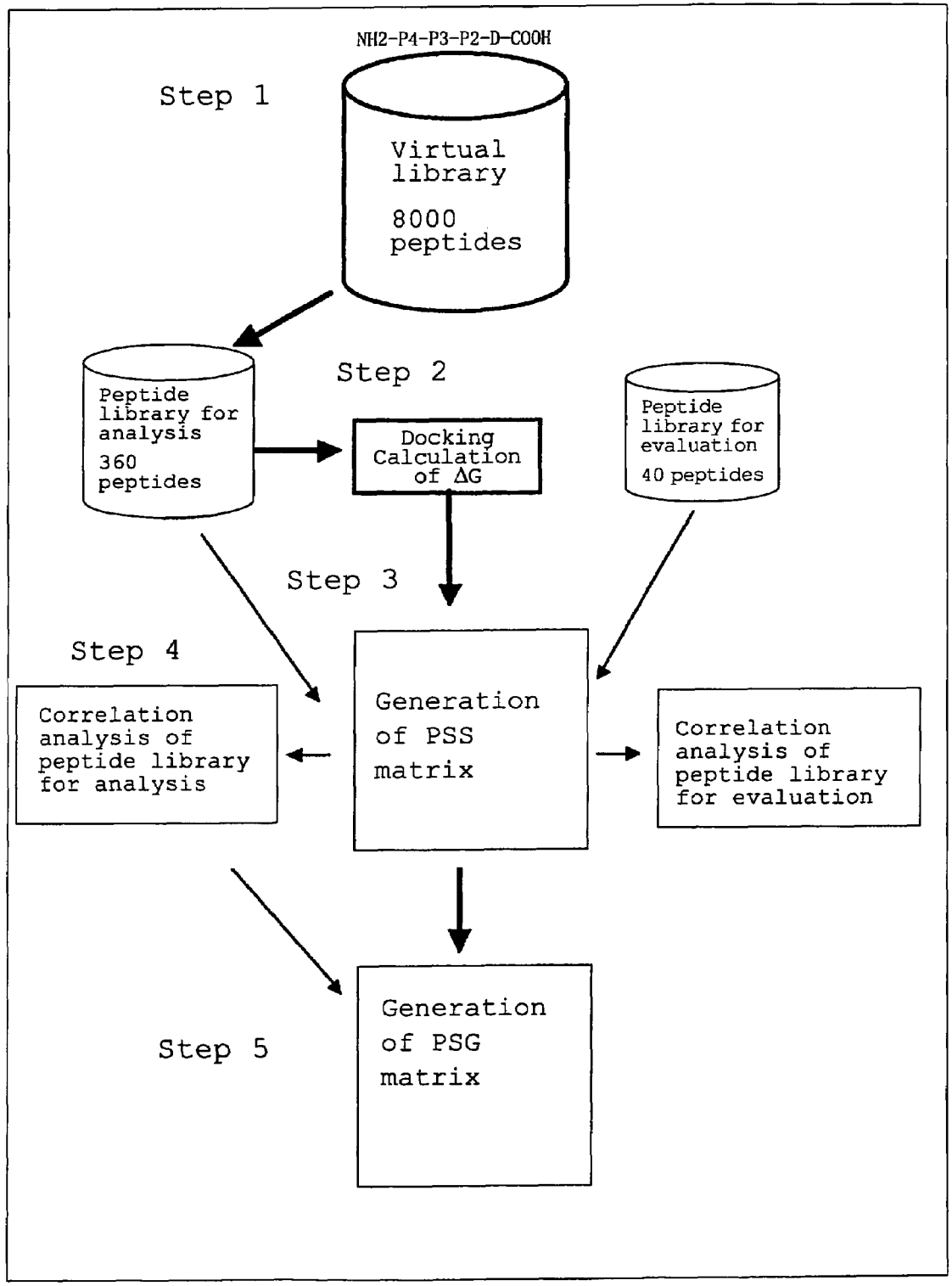
FIG. 9 shows a summary of amino acid position-dependent binding significance evaluation (first screening).

FIG. 8 is a flow chart showing program flows of (28) above and a portion of (29) above. This program is especially useful for enzymes etc. that have a pocket on the molecular surface thereof, and that are considered to undergo little structural changes associated with binding (e.g., peptidase) as target proteins. A summary of the processing conducted in (28) above is shown in FIG. 9. The program of (28) above is described in detail below, with reference to caspases given as examples of target proteins in due order, so as to facilitate the understanding thereof.

First, proteins serving as caspase substrates are described, and the amino acid positions thereof are defined. The amino acid sequence at the cleavage site of a protein serving as a caspase substrate is the X-X-X-D motif. The position of D in the motif indicates the P1 site, which is on the N-terminus side of the substrate cleavage site. The P1 position absolutely requires aspartic acid; the differences in inhibitor peptide recognized by each caspase are considered to be dependent on the amino acid sequence at the remaining P2~P4 positions. For this reason, to specify each amino acid position in the X-X-X-D motif, the amino acid sequence is hereunder expressed as P4-P3-P2-D.

The above-described step (a3) in the program of (28) above corresponds to step 401 of FIG. 8. In the above-described step (a3), amino acid sequences of constant length are generated exhaustively, from among which amino acid sequences are selected randomly and extracted as a library for analysis. Although it is not included in the above-described step (a3), a step for further extracting a library for evaluation may be included in step 401 of FIG. 8. Although the "constant length" (i.e., the number of amino acid residues) of the amino acid sequences generated exhaustively in the above-described step (a3) is not subject to limitation, it is preferably a length of about 2-10 amino acid residues, more preferably a length of 3-5 amino acid residues.

For example, to exhaustively analyze the P4-P3-P2-D motif, $20^3$, i.e., 8000 different combinations of amino acid sequences each consisting of four amino acid residues must be considered (D is constant; although non only natural amino acids but also amino acid equivalents may of course be considered, only natural amino acids are considered here, so as to simplify the description), even if only natural amino acids are taken into consideration. Here, for example, it is also possible to randomly select 400 amino acid sequences, which account for 5% of the combinations, and extract 360 amino acid sequences as a library for analysis and 40 amino acid sequences as a library for evaluation. Regarding caspases, inhibitor peptides thereof are known; the caspase inhibitor retain nearly the same primary chain structure for all caspases according to crystalline structure of complex with caspase inhibitor peptides. Hence, it is considered that the shape and catalytic mechanism of the caspase active site limit it. Such findings may be used to help produce a peptide conformation. For example, in producing a peptide conformation, an optionally chosen peptide may be constructed using a structure in the crystalline structure as the primary chain structure with a side chain added thereto. Additionally, to eliminate the VDW contact of the side chain, energy optimization may be conducted using TINKER (see, for example, Pappu, R. V. et al, J. Phys. Chem. B, 102, 9725-9742 (1998)). In this case, the primary chain may be immobilized using the INACTIVE command.

The above-described step (b3) corresponds to step 402 of FIG. 8. In the above-described step (b3), an intermolecular energy parameter is calculated for each of the amino acid sequences extracted as a library for analysis. This calculation is conducted in the same manner as the above-described step (g1') of the above-described program (13). For example, with regard to 8000 different amino acid sequences generated exhaustively for the P4-P3-P2-D motif, the calculation shown by [Equation 18] below may be conducted using AutoDock.

$$\Delta G_{calc} = \Delta G_{vdw} \sum_{i,j} \left( \frac{A_{ij}}{r_{ij}^{12}} - \frac{B_{ij}}{r_{ij}^6} \right) +$$

$$\Delta G_{hbond} \sum_{i,j} E(t) \left( \frac{C_{ij}}{r_{ij}^{12}} - \frac{D_{ij}}{r_{ij}^{10}} \right) + \Delta G_{elec} \sum_{i,j} \frac{q_i q_j}{\varepsilon(r_{ij}) r_{ij}} +$$

$$\Delta G_{tor} N_{tor} + \Delta G_{sol} \sum_{i,j} (S_i V_j + S_j V_i) e^{(-r_{ij}^2 / 2\sigma^2)}$$

[Equation 18]

The individual coefficients in the equation above are values determined empirically by a regression analysis using 30 protein-ligand complex structures and actual measured Ki values thereof. Since the introduction of AutoDock 3.0, a genetic algorithm based on Lamarck's evolution theory has newly been adopted for configuration search. Additionally, here, the primary chain of 4-residue peptide is fixed, whereas the side chain is variable. Examples of parameter values to be set forth are shown in Table 3. As described above, details of calculation requirements can be set forth as appropriate.

TABLE 3

| Parameters Set forth For Auto Dock | |
|---|---|
| Translation step | 2 Å |
| Quaternion step | 50° |
| Torsion step | 50° |
| Translation reduction factor | 1/cycle |
| Quaternion reduction factor | 1/cycle |
| Torsion reduction factor | 1/cycle |
| No. of top individuals that automatically survive | 1 |
| Rate of gene mutation | 0.02 |
| Rate of crossover | 0.8 |
| No. of generations for picking worst individual | 10 |
| Mean of Cauchy distribution for gene mutation | 0 |
| Variance of Cauchy distribution for gene mutation | 1 |
| No. of iterations of Solis and Wets local search | 300 |
| No. of consecutive successes before changing ρ | 4 |
| No. of consecutive failures before chaning ρ | 4 |
| Size of local search space to sample | 1 |
| Lower bound on ρ | 0.01 |
| Probability of performing local search on an individual | 0.06 |
| ga_pop_size | 50 |

TABLE 3-continued

Parameters Set forth For Auto Dock

| | |
|---|---|
| ga_num_evals | 700000 |
| ga_num_generations | 27000 |

Also, although it is not included in the above-described step (b3), a step for comparing the configuration of an extracted amino acid sequence (e.g., based on RMS (primary chain)) with the configuration of a control (e.g., peptide in the crystalline structure), and excluding sequences of any inappropriate configuration from the subsequent calculations, may be included in the above-described step (b3). For example, regarding the amino acid sequence of the P4-P3-P2-D motif, the configuration thereof is confirmed by RMS (primary chain) with an inhibitor peptide in the crystalline structure. Sequences of great RMS may be considered to fail to be appropriately arranged at the caspase active site and not to function as substrates, and hence excluded from the subsequent calculations. This is because the appropriate configuration of peptide is an essential factor for a modifying group like FMK or CHO to be arranged at the caspase active center, though it seems to be unproblematic irrespective of what is the configuration, provided that a strong bond is formed.

The above-described step (c3) corresponds to step 403 of FIG. 8. In the above-described step (c3), a score matrix based on amino acid prevalence is generated using an intermolecular energy parameter calculated in the above-described step (b3). The threshold value of an intermolecular energy parameter (e.g., threshold value of $\Delta G$) may be set forth in advance, or may be set forth as described below. For example, PSS matrices based on prevalence of 20 kinds of amino acid at each of positions P4, P3, and P2 are generated using a library for analysis containing 360 amino acid sequences. The $PSS_{ij}$ of amino acid i at position j is calculated by [Equation 9] above. In this case, the range of position "j" is 1-3, which correspond to P4-P2, respectively, and the range of amino acid "i" is 1-20, which correspond to individual amino acid species.

The above-described step (d3) corresponds to step 404 of FIG. 8. In the above-described step (d3), a score based on amino acid prevalence is calculated using a score matrix based on amino acid prevalence. For example, by using the PSS matrix, the strength of the binding force of an optionally chosen amino acid sequence consisting of four amino acid residues (P4-P3-P2-D motif: P1 is constantly D and hence not taken into consideration) for caspases can be calculated as PSS by [Equation 10] above. In this case, $C_{ij}$ is a 20×3 matrix, consisting of a value of 0 or 1. A factor agreeing with amino acid "i" at position "j" of an optionally chosen amino acid sequence is written as 1, and a disagreeing factor is written as 0.

The above-described step (e3) corresponds to step 405 of FIG. 8. In the above-described step (e3), a correlation analysis is conducted between an intermolecular energy parameter calculated in step (b3) and said score to obtain a regression equation. If a high correlation is present between PSS and an intermolecular energy parameter (e.g., binding free energy) for each amino acid sequence contained in a library for analysis, it is possible to predict an intermolecular energy parameter for a new amino acid sequence at high speed. Of course, because PSS can only be evaluated independently for each position, the influence of combining amino acids between different positions cannot be considered. The threshold value of an intermolecular energy parameter described in the above-described step (c3) (e.g., threshold value of $\Delta G$) may also be set forth to maximize the correlation coefficient R between PSS and the threshold value of an intermolecular energy parameter (e.g., threshold value of $\Delta G$). In this case, the threshold value set forth to maximize the correlation coefficient R is returned to the above-described step (c3), and the above-described step (c3), the above-described step (d3) and the above-described step (e3) are taken again.

The above-described step (f3) corresponds to step 406 of FIG. 8. In the above-described step (f3), a score matrix based on amino acid prevalence is converted to a matrix based on an amino acid position-dependent intermolecular energy parameter using the regression equation. In this conversion, the PSG matrix described above, for example, is generated. Although the constant term in the regression equation may be distributed to individual positions non-uniformly, it is preferably distributed to individual positions uniformly.

The above-described step (g3) corresponds to step 407 of FIG. 8. In the above-described step (g3), an amino acid position-dependent intermolecular energy parameter value is calculated from a matrix based on an amino acid position-dependent intermolecular energy parameter. For example, using the PSG matrix, the binding free energy between an optionally chosen 4-residue peptide (P4-P3-P2-D motif: P1 is constantly D and is therefore not considered) and caspase can be calculated as PSG at high speed.

The above-described step (h3) corresponds to step 408 of FIG. 8. In the above-described step (h3), amino acid sequences lower than a specified amino acid position-dependent intermolecular energy parameter value, i.e., amino acid sequences lower than the threshold value, are extracted. This value may be set forth in advance, or may be set forth at the time of extraction.

Next, the program of (29) above is described in detail below.

The above-described steps (a3')-(h3') of the program of (29) above correspond to the above-described steps (a3)-(h3) of the program of (28) above. Therefore, the above-described steps (a3')-(h3') of the program of (29) above are conducted in the same manner as the above-described steps (a3)-(h3) of the program of (28) above.

Also, the above-described steps (i3')-(l3') of the program of (29) above correspond to the above-described steps (c2')-(f2') of the program of (26) above. Therefore, the above-described steps (i3')-(l3') of the program of (29) above are conducted in the same manner as the above-described steps (c2')-(f2') of the program of (26) above.

Furthermore, between the above-described step (k3') and step (l3'), the above-described steps (I)-(III) may be included. The above-described steps (I)-(III) are conducted in the same manner as described above.

Also, if a plurality of proteins similar to each other in terms of substrate specificity are present, one of these proteins is selected as the target protein, and the programs of (28) and (29) above are useful in designing a peptide specific therefor. As an example, a description is made referring to the program of (28) above. First, for each of the proteins similar to each other in terms of substrate specificity, the above-described steps (a3)-(h3) of the above-described program (28) are conducted. For each protein, the above-described steps (a3)-(h3) may be taken concurrently, or the above-described steps (a3)-(h3) may be taken in due order. Subsequently, for the target protein and other proteins, a difference in an amino acid position-dependent intermolecular energy parameter value (e.g., PSG) is calculated, and a step for filtering by that difference is provided. This difference can be set forth as appropriate. For example, when a Ki value for the target protein better by two digits than the Ki values of other proteins is desired, ΔG can be used as the filter because it is equivalent to 2.728 kcal/mol. Of course, the above-described step (h3') of the above-described program (29) may be followed by a similar step, after which progress to the above-described step (i3') may be made. Having been explained briefly, the present invention may include a step as described above in the programs of (28) and (29) above. Such programs are included in the scope of the present invention. Further examples are given in Example 3 and will help understand such programs.

The recording medium of (17) above of the present invention is a computer-readable recording medium containing the above-described programs of the present invention recorded therein. Here, a "computer-readable recording medium" refers to an optionally chosen recording medium capable of recording electronic data, and readable by a computer as necessary, and is exemplified by portable information recording media such as magnetic tapes, magnetic discs, magnetic drums, IC cards, and optical discs (e.g., CD, DVD).

According to the present invention, the extraction processing units of (18)-(20) above, the extraction processing units of (21)-(23) above, and the apparatuses of (31) and (32) above, are dedicated machines for extracting a physiologically active peptide configured mainly with a computer provided with a central processing unit and a memory, and having the above-described programs of the present invention in a way such that they are executable.

The apparatuses of (18)-(23) above can be roughly divided, from the viewpoint of designing a physiologically active peptide that interacts with a target amino acid sequence, and a physiologically active peptide that interacts with a target protein, into two sets. One is a set of the apparatuses shown in (18)-(20) above, and this is intended to design a physiologically active peptide that interacts with a target amino acid sequence. The other is a set of the apparatuses shown in (21)-(23) above, and this is intended to design a physiologically active peptide in consideration of the interaction with a target protein itself, as well as the interaction with a target amino acid sequence.

Figure 10:
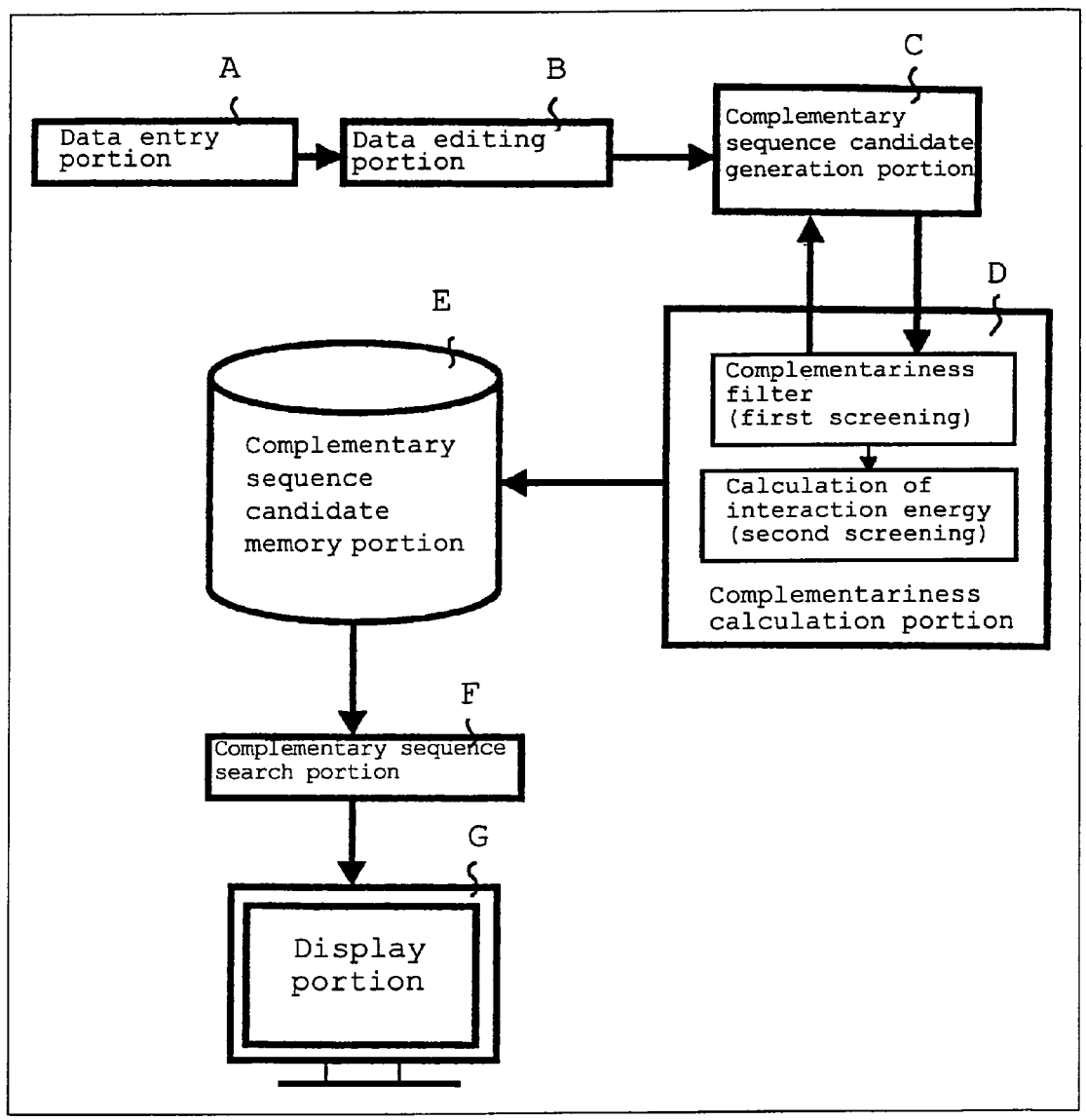
FIG. 10 shows an example of a configuration of an apparatus for designing a physiologically active peptide.

The apparatuses of (18)-(20) above, as shown in FIG. 10, are configured to include a data entry portion A, a data editing portion B, a complementary amino acid sequence candidate generation portion C, a complementariness calculation portion D, a complementary amino acid sequence candidate memory portion E, a complementary amino acid sequence search portion F, and a complementary amino acid sequence display portion G.

In the apparatuses of (18)-(20) above, said data entry portion A includes a means of executing the above-described step (a1), said data editing portion B includes a means of executing the above-described step (b1), said complementary amino acid sequence candidate generation portion C includes a means of executing the above-described step (c1), said complementariness calculation portion D includes a means of executing the above-described step (d1), said complementary amino acid sequence candidate memory portion E includes a means of executing the above-described step (e1), said complementary amino acid sequence search portion F includes a means of executing the above-described step (f1), and said complementary amino acid sequence display portion G includes a means of executing the above-described step (g1).

The apparatuses of (21)-(23) above, like the apparatuses of (18)-(20) above, as shown in FIG. 10, are configured to include a data entry portion A, a data editing portion B, a complementary amino acid sequence candidate generation portion C, a complementariness calculation portion D, a complementary amino acid sequence candidate memory portion E, a complementary amino acid sequence search portion F, and a complementary amino acid sequence display portion G.

In the apparatuses of (21)-(23) above, said data entry portion A includes a means of executing the above-described step (a1'), said data editing portion B includes a means of executing the above-described step (b1'), said complementary amino acid sequence candidate generation portion C includes a means of executing the above-described step (c1'), said complementariness calculation portion D includes a means of executing step (k1') for calculating each of complementariness parameters from the same amino acid index between one or more moving average profile waveforms for the target amino acid sequence and one or more complementary moving average profile waveforms of a candidate for complementary amino acid sequence, and further calculating an intermolecular energy parameter with a target site of target protein (a means of executing the above-described steps (d1') and (g1')), said complementary amino acid sequence candidate memory portion E includes a means of executing step (l1') for storing a candidate for complementary amino acid sequence, along with the complementariness parameter and the intermolecular energy parameter (a means of executing the above-described steps (e1') and (h1')), said complementary amino acid sequence search portion F includes a means of executing step (m1') for extracting a specified number of complementary amino acid sequences on the basis of information stored by means (k1') (a means of executing the above-described steps (f1') and (i1')), and said complementary amino acid sequence display portion G includes a means of executing step (n1') for displaying complementary amino acid sequences extracted by said complementary amino acid sequence search portion as candidates for physiologically active peptides (a means of executing the above-described step (i1')).

The apparatuses of (31) and (32) above are similar to the apparatuses of (18)-(23) above; all of the "(A2) interaction region identification portion, (B2) first amino acid sequence search portion, (C2) intermolecular energy calculation portion, (D2) amino acid sequence memory portion, (E2) second amino acid sequence search portion, and (F2) amino acid sequence display portion" included in the apparatus of (31) above, and the "(A3) first amino acid sequence search portion, (B3) first intermolecular energy calculation portion, (C3) score matrix generation portion, (D3) score calculation portion, (E3) regression equation generation portion, (F3) matrix conversion portion, (G3) amino acid position-dependent energy calculation portion, (H3) second amino acid sequence search portion, (I3) second intermolecular energy calculation portion, (J3) amino acid sequence memory portion, (K3) third amino acid sequence search portion, and (C3) amino acid sequence display portion" included in the apparatus of (32) above, are configured with the programs of (26) and (29) above, a computer configured to execute the programs (central processing unit (CPU), storage (memory)), and peripheral apparatuses added as necessary (external storage, data entry apparatus, display apparatus, etc.), and may have a network with another computer added to the configuration.

The individual portions (A2)-(F2) included in the apparatus of (31) above, and the individual portions (A3)-(L3) included in the apparatus of (32) above are as described in detail in the descriptions of the programs of (26) and (29) above, respectively.

The apparatus of the present invention may further comprise an output apparatus, such as a printer for printing displayed data, an external storage for data storage, an external storage incorporating a database necessary to execute the programs of the present invention, etc., and other devices that provide the user with convenience in designing a physiologically active peptide.

EXAMPLES

The present invention is hereinafter described in more detail by means of, but is not limited to, the following examples.

Example 1

Designing a Physiologically Active Peptide (Inhibitor Peptide) for Caspase-3

With the amino acid sequence WRNS of caspase-3 at position 206~209 (SEQ ID NO:109) as the target amino acid sequence, peptide candidates that bind thereto to inhibit caspase-3 activity were predicted using the program of the present invention. An index based on the degree of hydrophobicity (see, for example, Eisenberg D, et al., J. Ann. Rev. Biochem., 53, 596-623 (1984)) was used as an amino acid index, and window width was set forth at 1. With the range of $P_{ave}$ set forth between −0.39 and −0.37, and $R_t$ set forth at −0.9, 105 peptide candidates having a complementary amino acid sequence were obtained by first screening (Table 4). The sequences ranked 1-105 in Table 4 are designated as SEQ ID NO:4-108, respectively, in due order.

TABLE 4

Screening Results of Caspase-3 Inhibitor Peptides

| | | First screening | | Second screening | |
|---|---|---|---|---|---|
| rank | sequence | comp. R | a.d.h. | ΔG | Ki |
| 1 | NHFK | −0.997 | −0.383 | −7.56 | 2.88E−06 |
| 2 | EHFK | −0.997 | −0.378 | −10.21 | 3.30E−08 |
| 3 | QSVK | −0.997 | −0.378 | −4.64 | 4.00E−04 |
| 4 | QSLK | −0.997 | −0.380 | −5.11 | 1.79E−04 |
| 5 | DSVK | −0.995 | −0.385 | −8.74 | 3.93E−07 |
| 6 | DSLK | −0.995 | −0.388 | −8.51 | 5.78E−07 |
| 7 | DHIK | −0.993 | −0.373 | −8.03 | 1.31E−06 |
| 8 | ETWK | −0.986 | −0.383 | −6.57 | 1.54E−05 |
| 9 | NTWK | −0.985 | −0.388 | −7.24 | 4.91E−06 |
| 10 | HHPE | −0.985 | −0.373 | −10.89 | 1.05E−08 |
| 11 | HHPN | −0.984 | −0.378 | −10.98 | 8.96E−09 |
| 12 | HHYD | −0.983 | −0.375 | −9.36 | 1.37E−07 |
| 13 | HHWK | −0.977 | −0.383 | −9.37 | 1.36E−07 |
| 14 | EHAD | −0.976 | −0.373 | −11.44 | 4.11E−09 |
| 15 | EHGQ | −0.974 | −0.388 | −9.07 | 2.26E−07 |
| 16 | NHAD | −0.973 | −0.378 | −9.19 | 1.84E−07 |
| 17 | NHMD | −0.972 | −0.375 | −7.73 | 2.15E−06 |
| 18 | HSMK | −0.966 | −0.375 | −2.90 | 0.01 |
| 19 | QPWK | −0.965 | −0.373 | −9.85 | 6.03E−08 |
| 20 | HSAK | −0.964 | −0.378 | −7.37 | 3.95E−06 |
| 21 | QHAD | −0.963 | −0.390 | −7.93 | 1.53E−06 |
| 22 | DPWK | −0.963 | −0.380 | −10.44 | 2.21E−08 |
| 23 | QHMD | −0.963 | −0.388 | −9.92 | 5.39E−08 |
| 24 | ESCQ | −0.961 | −0.383 | −9.21 | 1.78E−07 |
| 25 | EHGN | −0.959 | −0.375 | −9.01 | 2.48E−07 |
| 26 | ESYQ | −0.958 | −0.388 | −8.79 | 3.62E−07 |
| 27 | QSGD | −0.957 | −0.378 | −8.30 | 8.22E−07 |
| 28 | QHAQ | −0.955 | −0.383 | −8.10 | 1.15E−06 |
| 29 | QHMQ | −0.955 | −0.380 | −6.66 | 1.31E−05 |
| 30 | NSCQ | −0.955 | −0.388 | −7.72 | 2.18E−06 |
| 31 | HEFK | −0.954 | −0.378 | −8.40 | 6.91E−07 |
| 32 | NHGN | −0.954 | −0.380 | −9.49 | 1.10E−07 |
| 33 | EPMK | −0.952 | −0.383 | −7.59 | 2.72E−06 |
| 34 | NPMK | −0.952 | −0.388 | −5.23 | 1.46E−04 |
| 35 | EPAK | −0.951 | −0.385 | −9.51 | 1.07E−07 |
| 36 | HNFK | −0.950 | −0.383 | −5.82 | 5.38E−05 |
| 37 | HPIR | −0.950 | −0.375 | −3.99 | 0 |
| 38 | DSGD | −0.948 | −0.385 | −11.23 | 5.87E−09 |
| 39 | DHMQ | −0.947 | −0.388 | −8.42 | 6.77E−07 |
| 40 | ESYN | −0.947 | −0.375 | −8.71 | 4.13E−07 |
| 41 | NHGE | −0.947 | −0.375 | −10.60 | 1.70E−08 |
| 42 | NGIR | −0.945 | −0.378 | −3.71 | 0 |
| 43 | EGIR | −0.944 | −0.373 | −7.44 | 3.53E−06 |
| 44 | NSCN | −0.942 | −0.375 | −8.00 | 1.37E−06 |
| 45 | KPIK | −0.941 | −0.385 | −4.66 | 3.82E−04 |
| 46 | DSGQ | −0.940 | −0.378 | −7.85 | 1.77E−06 |
| 47 | SSIR | −0.939 | −0.388 | −4.03 | 0 |
| 48 | NSYN | −0.939 | −0.380 | −8.28 | 8.51E−07 |
| 49 | HTGK | −0.938 | −0.380 | −4.74 | 3.38E−04 |
| 50 | HDIK | −0.935 | −0.373 | −6.66 | 1.31E−05 |
| 51 | DAIR | −0.935 | −0.375 | −9.38 | 1.32E−07 |
| 52 | ETYD | −0.934 | −0.375 | −10.32 | 2.71E−08 |
| 53 | DMIR | −0.934 | −0.373 | −4.88 | 3.70E−04 |
| 54 | NTCD | −0.933 | −0.375 | −6.45 | 1.88E−05 |
| 55 | NSYE | −0.932 | −0.375 | −11.5 | 3.75E−09 |
| 56 | QHGE | −0.931 | −0.388 | −9.23 | 1.73E−07 |
| 57 | SHMK | −0.930 | −0.375 | −6.21 | 2.79E−05 |
| 58 | DHAN | −0.930 | −0.378 | −9.87 | 5.78E−08 |
| 59 | DHMN | −0.930 | −0.375 | −8.85 | 3.27E−07 |
| 60 | SHAK | −0.929 | −0.378 | −4.77 | 3.16E−04 |
| 61 | HYFR | −0.928 | −0.383 | −6.61 | 1.42E−05 |
| 62 | NTYD | −0.928 | −0.380 | −9.18 | 1.87E−07 |
| 63 | QYMK | −0.927 | −0.378 | −5.81 | 5.47E−05 |
| 64 | HCFR | −0.926 | −0.378 | −4.84 | 2.82E−04 |
| 65 | DYMK | −0.925 | −0.385 | −8.59 | 5.07E−07 |
| 66 | QYAK | −0.925 | −0.380 | −8.1 | 1.15E−06 |
| 67 | NTYQ | −0.923 | −0.373 | −7.73 | 2.15E−06 |
| 68 | DYAK | −0.923 | −0.388 | −8.22 | 9.37E−07 |
| 69 | DHAE | −0.922 | −0.373 | −12.63 | 5.51E−10 |
| 70 | QCMK | −0.921 | −0.373 | −4.83 | 2.88E−04 |
| 71 | QSCN | −0.920 | −0.388 | −7.53 | 3.01E−06 |
| 72 | DCMK | −0.919 | −0.380 | −9.67 | 8.17E−08 |
| 73 | QCAK | −0.919 | −0.375 | −8.65 | 4.57E−07 |
| 74 | KCFK | −0.919 | −0.388 | −6.95 | 8.07E−06 |
| 75 | QTCD | −0.917 | −0.388 | −8.68 | 4.36E−07 |
| 76 | DCAK | −0.917 | −0.383 | −8.72 | 4.05E−07 |
| 77 | NAFR | −0.917 | −0.385 | −6.38 | 2.11E−05 |
| 78 | EAFR | −0.916 | −0.380 | −7.43 | 3.57E−06 |
| 79 | NMFR | −0.915 | −0.383 | −5.59 | 7.97E−05 |
| 80 | EMFR | −0.915 | −0.378 | −7.94 | 1.51E−06 |
| 81 | QELD | −0.913 | −0.375 | −8.83 | 3.39E−07 |
| 82 | QEVD | −0.913 | −0.373 | −8.02 | 1.32E−06 |
| 83 | QSCE | −0.913 | −0.383 | −8.9 | 3.00E−07 |
| 84 | DELD | −0.911 | −0.383 | −11.09 | 7.37E−09 |
| 85 | DEVD | −0.910 | −0.380 | −13.40 | 1.49E−10 |
| 86 | SQVK | −0.910 | −0.378 | −8.85 | 3.26E−07 |
| 87 | QTCQ | −0.910 | −0.380 | −8.46 | 6.27E−07 |
| 88 | TTFR | −0.910 | −0.378 | −5.67 | 6.92E−05 |
| 89 | SQLK | −0.909 | −0.380 | −9.11 | 2.11E−07 |
| 90 | QSYE | −0.909 | −0.388 | −7.5 | 3.18E−06 |
| 91 | QNLD | −0.908 | −0.380 | −9.67 | 8.17E−08 |
| 92 | QNVD | −0.908 | −0.378 | −9.21 | 1.78E−07 |
| 93 | SPVR | −0.907 | −0.388 | −5.32 | 1.27E−04 |
| 94 | DNLD | −0.906 | −0.388 | −14.34 | 3.09E−11 |
| 95 | DNVD | −0.906 | −0.385 | −11.79 | 2.26E−09 |
| 96 | EYGK | −0.905 | −0.385 | −10.11 | 3.86E−08 |
| 97 | HEAD | −0.905 | −0.373 | −9.89 | 5.65E−08 |
| 98 | PHIR | −0.905 | −0.375 | −6.27 | 2.54E−05 |
| 99 | QTYQ | −0.905 | −0.385 | −10.82 | 1.17E−08 |
| 100 | HSTQ | −0.904 | −0.383 | −6.83 | 9.89E−06 |
| 101 | SDVK | −0.903 | −0.385 | −9.78 | 6.78E−08 |
| 102 | SDLK | −0.902 | −0.388 | −8.23 | 9.34E−07 |
| 103 | DELQ | −0.901 | −0.375 | −10.48 | 2.09E−08 |
| 104 | DEVQ | −0.901 | −0.373 | −8.83 | 3.36E−07 |
| 105 | DWFR | −0.900 | −0.375 | −9.44 | 1.20E−07 | comp. R: complementariness R
a.d.h.: average degree of hydrophobicity

Subsequently, complementary amino acid sequences of strong binding force, DNLD (SEQ ID NO:97) ($K_i$=0.0309 nM: first-ranking) and DEVD (SEQ ID NO:88) ($K_i$=0.149 nM: second-ranking), were obtained by second screening (Table 4).

Figure 11:
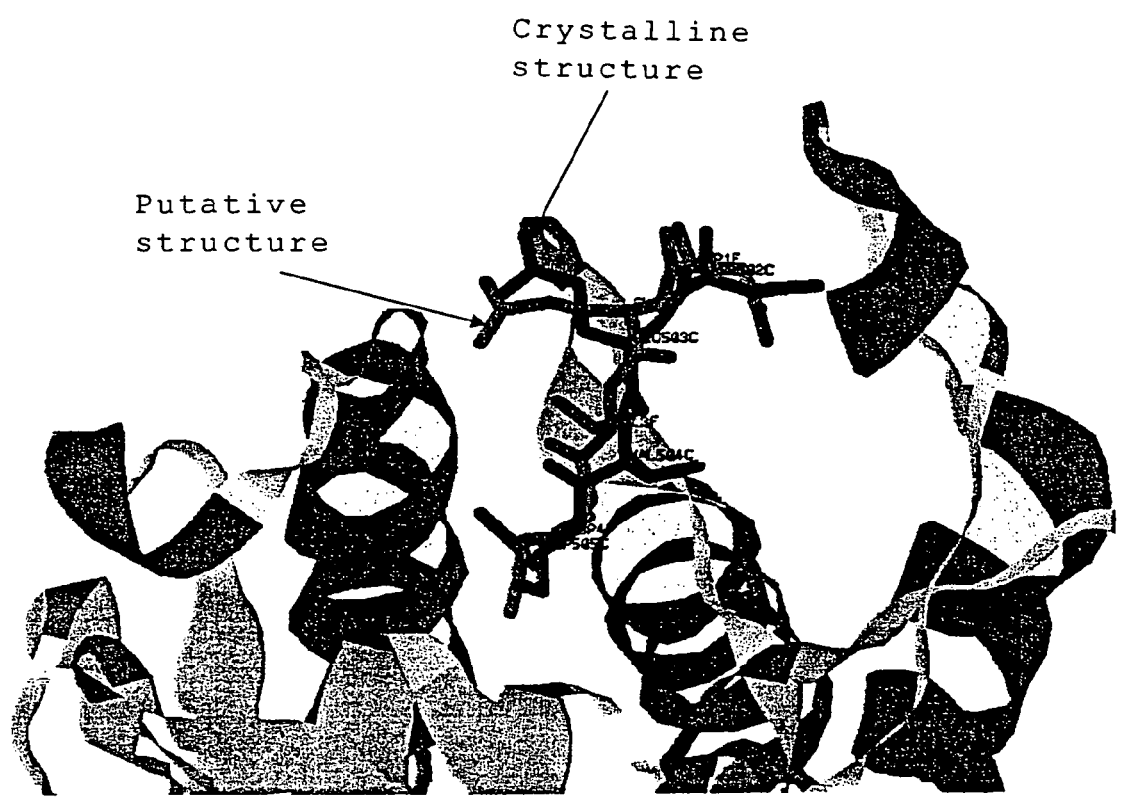
FIG. 11 shows an overlap of the complementary amino acid sequence DEVD and the crystalline structure.

DEVD (SEQ ID NO:88) is an amino acid sequence known as a caspase-3 inhibitor peptide, with the actual measured value of $K_i$ and crystalline structure thereof known. FIG. 11 shows a comparison of the complementary amino acid sequence DEVD predicted by the present invention and the crystalline structure. An RMS (root mean squar, average interatomic shift) (all atoms) of 2.4 Å was obtained; a structure very close to the crystalline structure was predicted successfully. The $K_i$ value predicted by the present invention was 0.149 nM, whereas the actual measured value (see, for example, Garcia-Calvo M, et al., J. Biol. Chem., 273, 32608-32613 (1998)) of $K_i$ was 0.23 nM.

Additionally, a currently unknown complementary amino acid sequence having the lowest $K_i$ value of 0.0309 nM, called DNLD (SEQ ID NO:97), was obtained. DEVD was initially obtained from the amino acid sequence of a protein serving as a substrate and, in addition, is characterized by strongly binding to caspase-7 and caspase-8, as well as to caspase-3 (see, for example, Garcia-Calvo M, et al., J. Biol. Chem., 273, 32608-32613 (1998)) and inhibiting them, with a problem for a specific inhibitor being suggested. Because the peptide sequence DNLD presented by this system is a totally new sequence, it provides the potential for resolving this specificity problem.

From the above results, it was confirmed that the program of the present invention is very useful in designing a candidate for complementary amino acid.

Example 2

Designing a Physiologically Active Peptide for Fas (Receptor)

With the amino acid sequence FSSKCRRCRLCDEG of Fas (Receptor) at position 97-110 (SEQ ID NO:1) as the target amino acid sequence, candidates for physiologically active peptide capable of binding to and interacting therewith were predicated using the program of the present invention. An index based on the degree of hydrophobicity (see, for example, Eisenberg D, et al., J. Ann. Rev. Biochem., 53, 596-623 (1984)) was used as an amino acid index, and window width was set forth at 5. With the range of $P_{ave}$ set forth between −0.15 and +0.15 and Rt set forth at −0.9, peptide candidates having a complementary amino acid sequence were obtained by first screening. Subsequently, intermolecular energy was calculated in second screening. Finally, the complementary amino acid sequence EPPMTFISIHTMCH (SEQ ID NO:2) was obtained.

Test Example 1

Induction of Apoptosis with a Peptide Comprising a Complementary Amino Acid Sequence (SEQ ID NO:2)

The peptide consisting of a complementary amino acid sequence (SEQ ID NO:2), obtained in Example 1 above (hereinafter abbreviated Fas complementary peptide), was chemically synthesized. Subsequently, using a Fas-expressing human ovarian cancer cell line NOS4, the apoptosis induction potential of the Fas complementary peptide was analyzed in comparison with a scrambled peptide thereof, TFIHPSMHTCMPEI (SEQ ID NO:3). NOS4 was established from a cancer cell sample resected from a patient with severe ovarian cancer, and has been maintained at the present inventors' laboratory. The human ovarian cancer cell line NOS4 was cultured in an RPMI medium containing 10% fetal bovine serum under 5% $CO_2$ moisture at 37° C. 5×10$^6$ cells of the human ovarian cancer cell line NOS4 were treated in the presence of 100 μg/ml complementary peptide at 37° C. for 24 hours, after which DNA fragmentation was measured. After the cell nucleus was stained with propidium iodide, DNA fragmentation was measured by flow cytometry using an FACS apparatus (FACS Calibur, Jose., Calif.). As a result, the Fas complementary peptide induced apoptosis in about 40% of the cells at a concentration of 100 μg/ml. From the above results, it was confirmed that the Fas complementary peptide functioned as a physiologically active peptide for Fas.

TABLE 5

Apoptosis Induction Activity of FRP-2 for Human Ovarian Cancer Cell Line (NOS4)

| Peptide | Sequence | Apoptosis (%)* |
| --- | --- | --- |
| None | | 10 ± 2 |
| Fas L | LPLSHKVYMRNSKY | 11 ± 3 |
| FRP-2 | EPPMTFISIHTMCH | 36 ± 5 |
| Scrambled FRP-2 | TFIHPSMHTCMPEI | 8 ± 2 |

*NOS4 cells were treated with FRP-2 (100 μg/ml) in a $CO_2$ incubator for 48 hours.
Apoptosis (%) was measured by FACSan analysis.

Test Example 2

Induction of Apoptosis with Fas Complementary Peptide Tetramer

Figure 12:
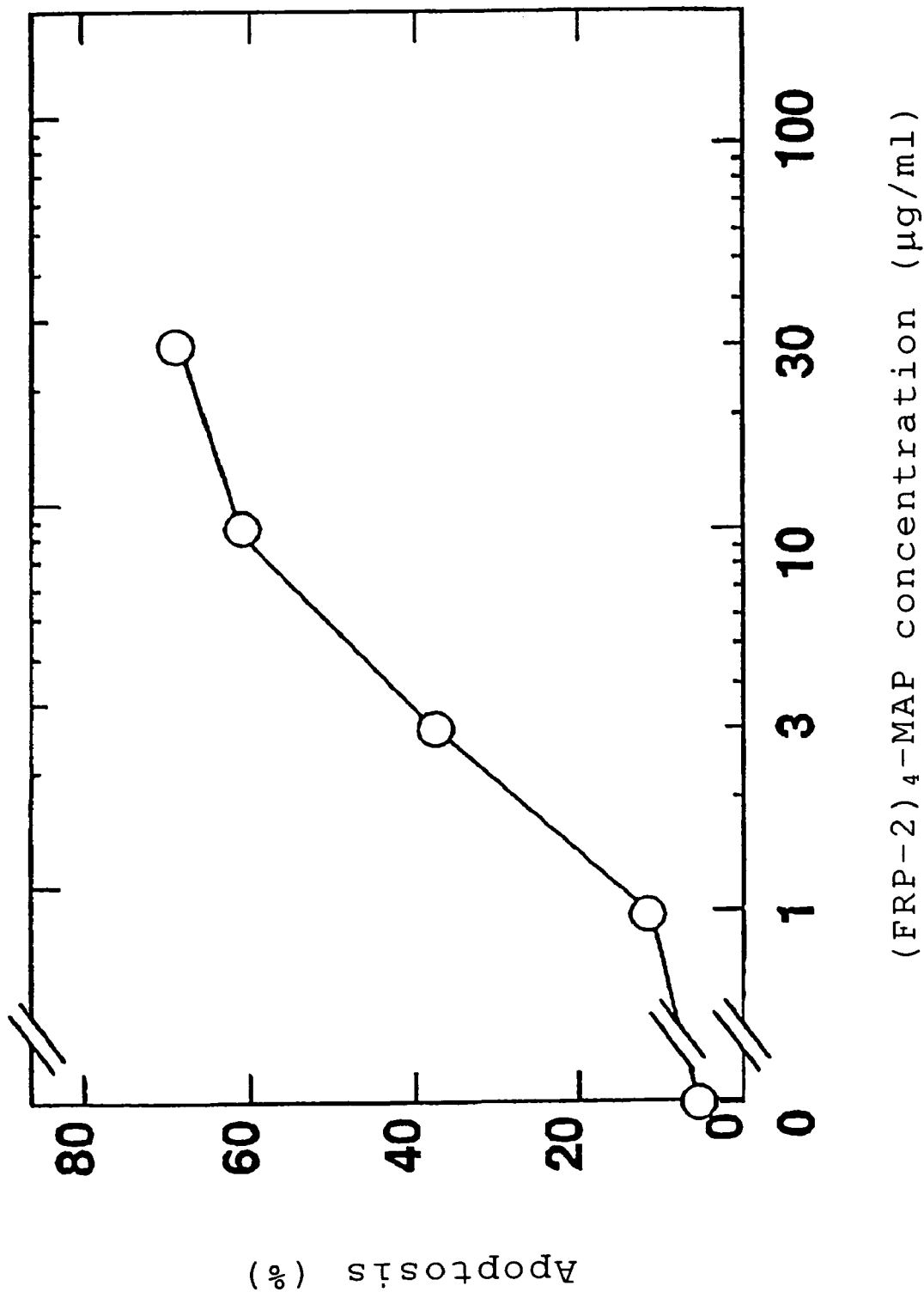
FIG. 12 shows the apoptosis induction potential of a Fas-complementary peptide tetramer.

Having the Fas complementary peptide (hereinafter also abbreviated FRP-2) bound to four branches of a lysine polymer (MAP), a tetramer of the Fas complementary peptide [(FRP-2)$_4$-MAP] was chemically synthesized. Subsequently, the apoptosis induction potential of (FRP-2)$_4$-MAP was examined using the same method as Test Example 1 above. As a result, the Fas complementary peptide tetramer induced apoptosis in about 50% of the human ovarian cancer cell line NOS4 at a concentration of 5 mg/ml (FIG. 12). From the above results, the Fas complementary peptide was found to exhibit an apoptosis induction potential about 30 times as potent as that of the monomer when rendered a maltimer using MAP.

Test Example 3

Induction of Apoptosis In Vivo with the Fas Complementary Peptide Tetramer

Figure 13:
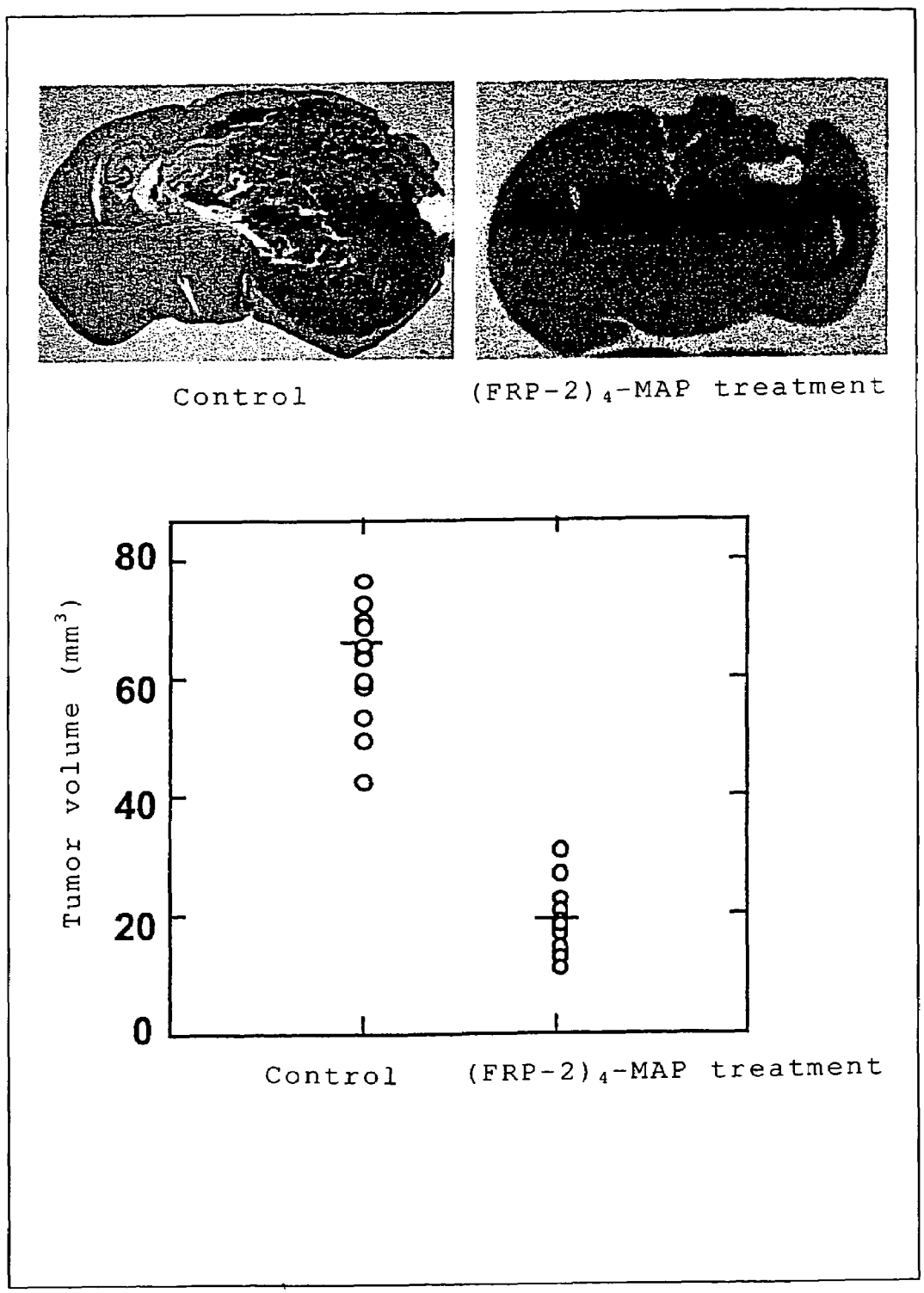
FIG. 13 shows mouse brain tissue treated with a Fas-complementary peptide tetramer and statistical data on tumor volume.
Figure 14A:
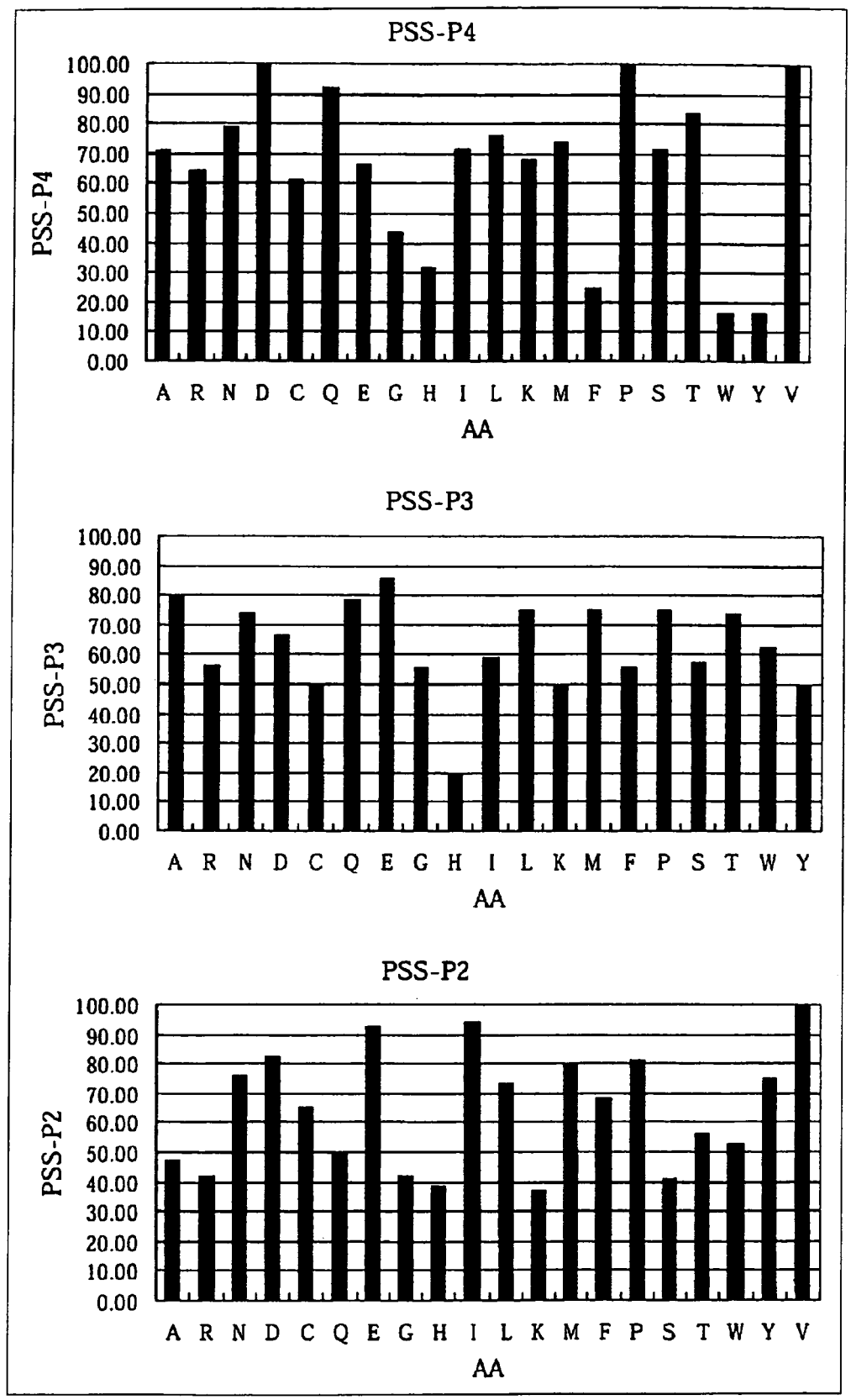
FIG. 14A shows the PSS at each position (P4, P3, P2) of the motif.
Figure 14D:
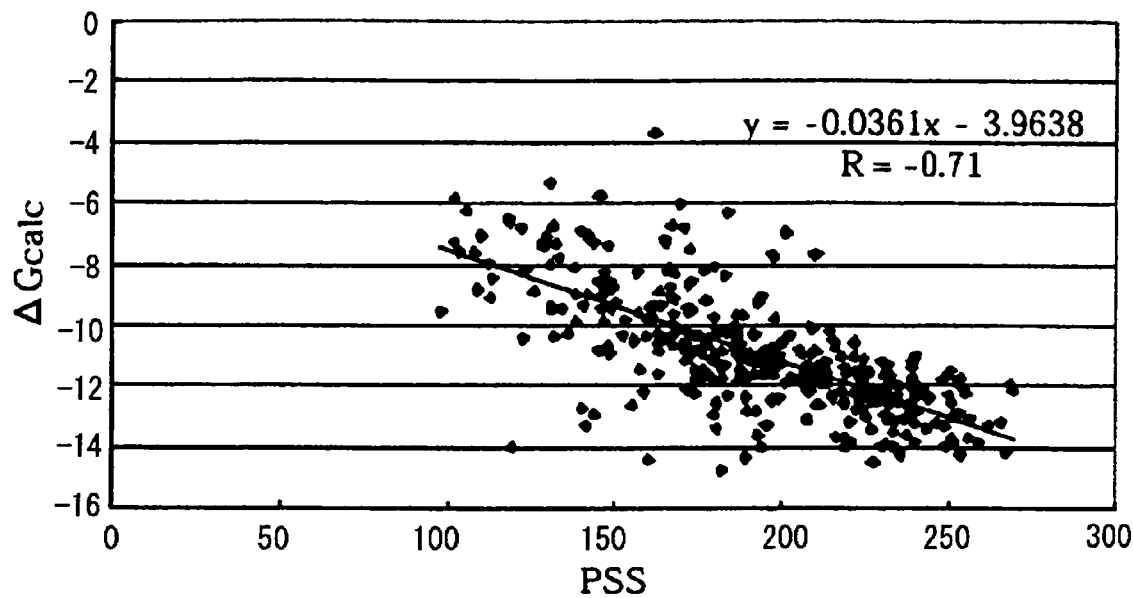
FIG. 14D shows a correlation analysis using a library for analysis.
Figure 14E:
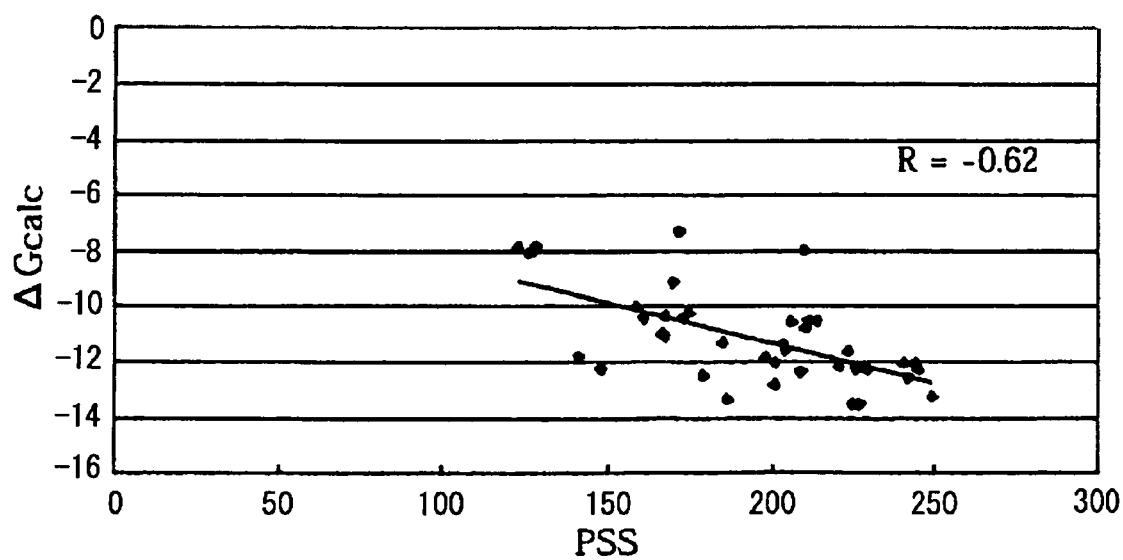
FIG. 14E shows a correlation analysis using a library for evaluation.
Figure 15A:
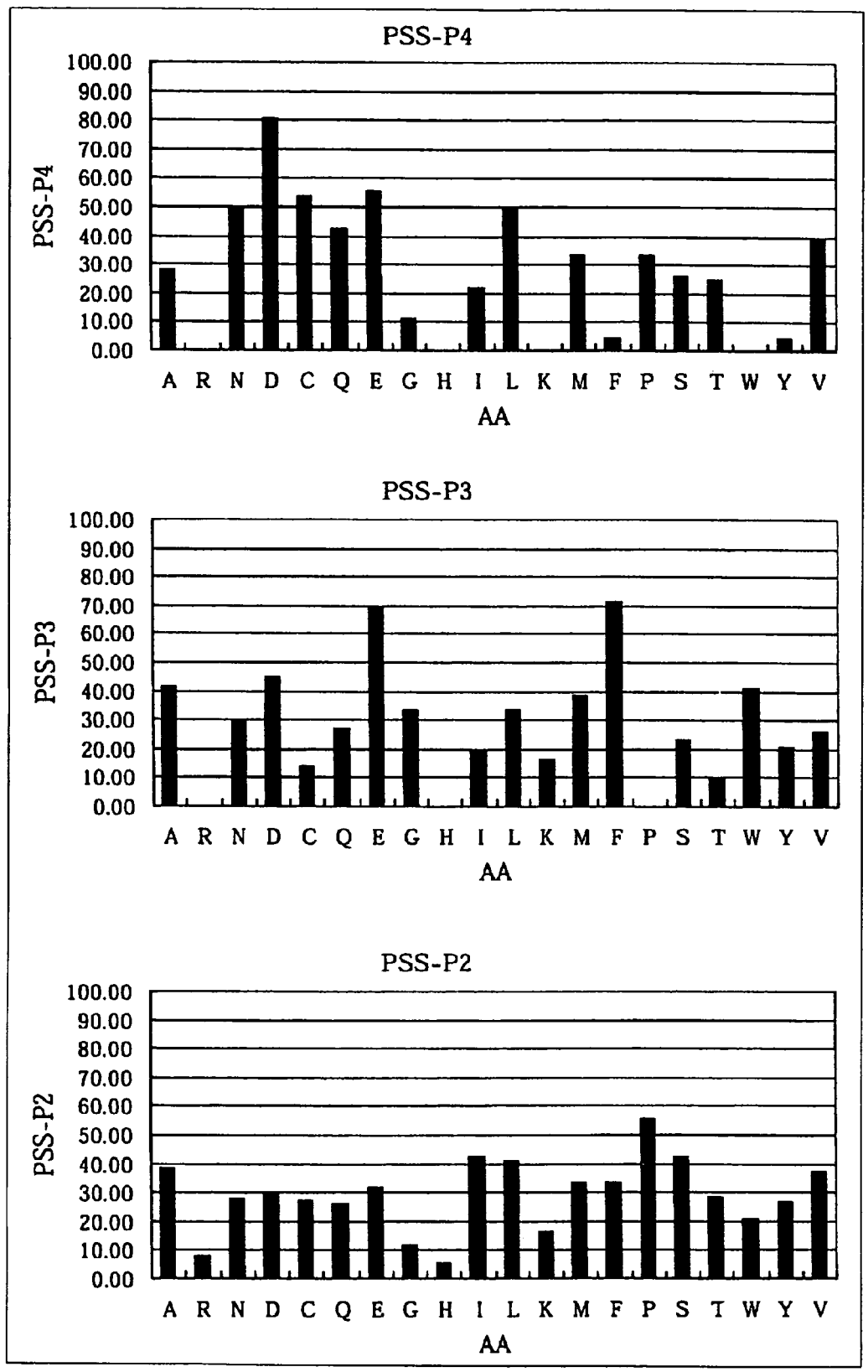
FIG. 15A shows the PSS at each position (P4, P3, P2) of the motif.
Figure 15D:
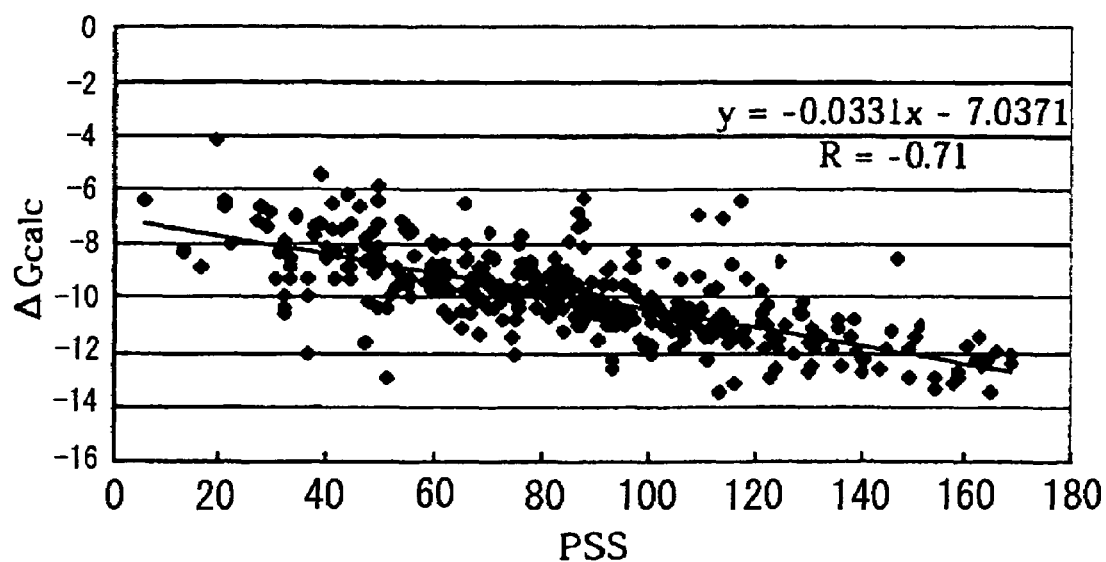
FIG. 15D shows a correlation analysis using a library for analysis.
Figure 15E:
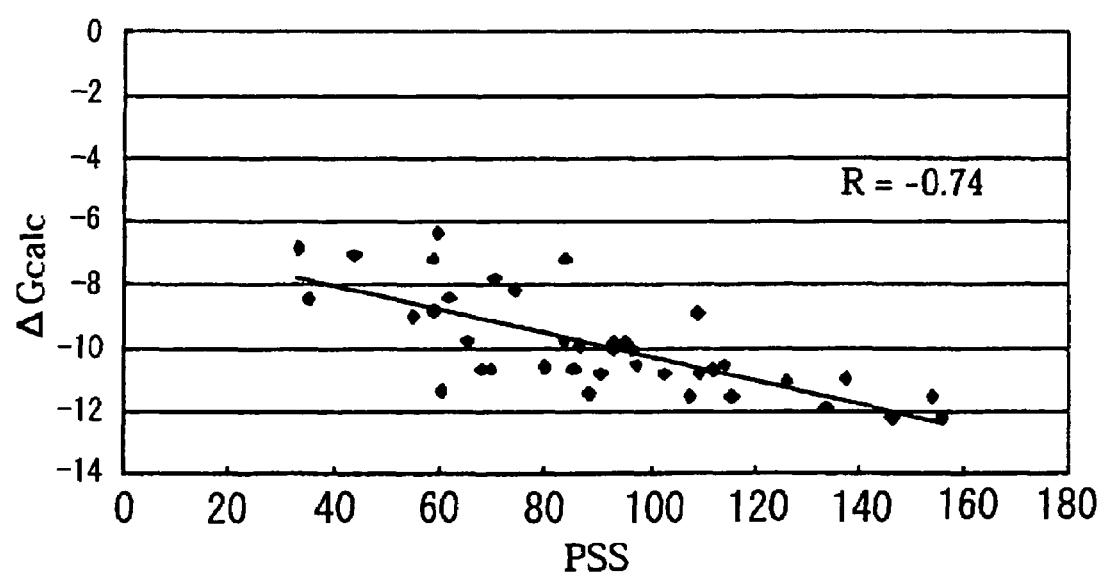
FIG. 15E shows a correlation analysis using a library for evaluation.
Figure 16A:
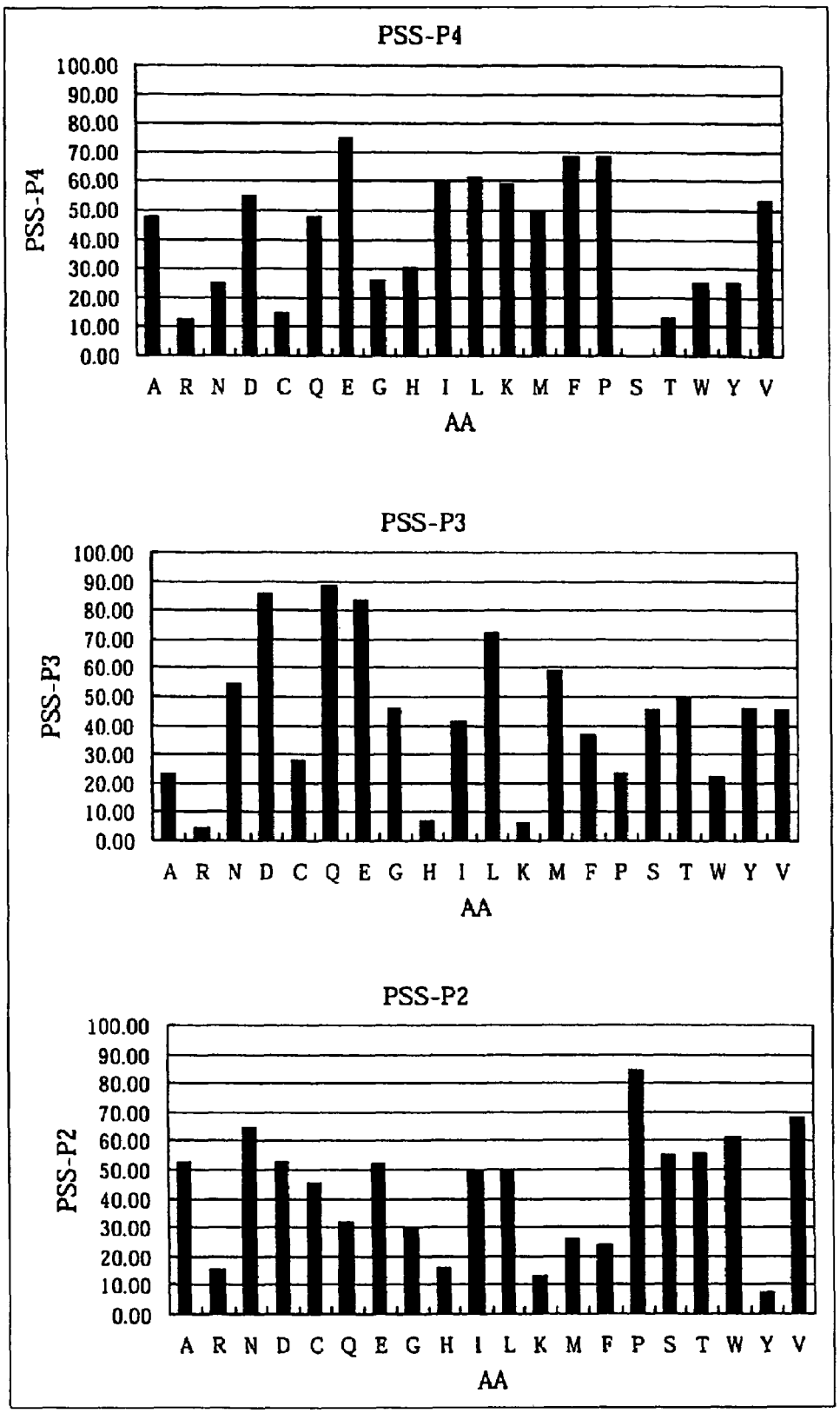
FIG. 16A shows the PSS at each position (P4, P3, P2) of the motif.
Figure 16D:
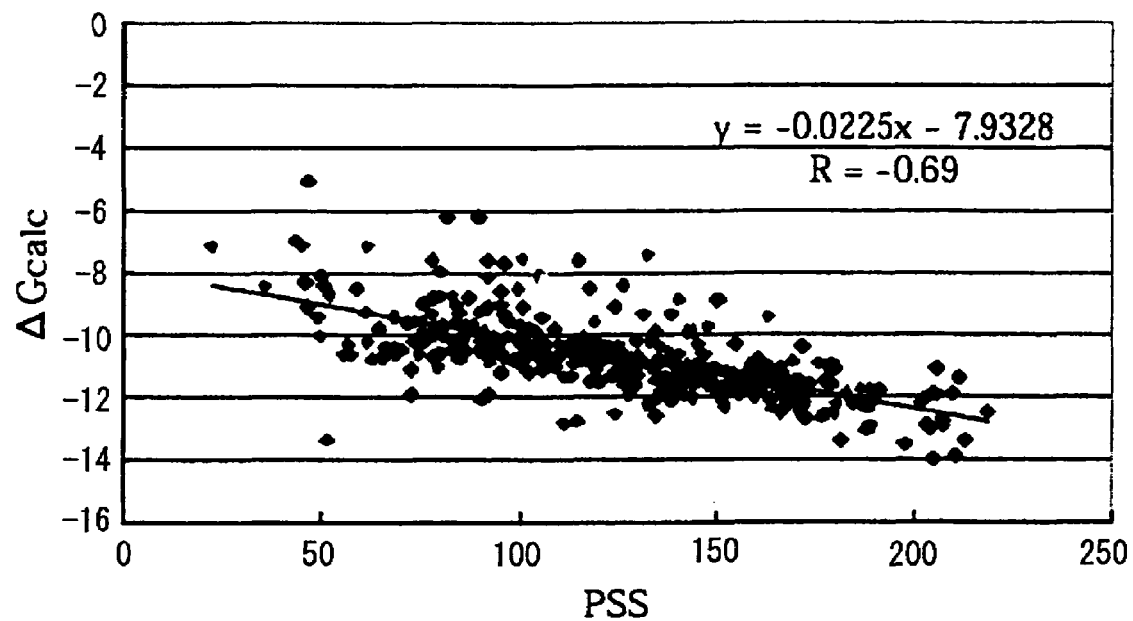
FIG. 16D shows a correlation analysis using a library for analysis.
Figure 16E:
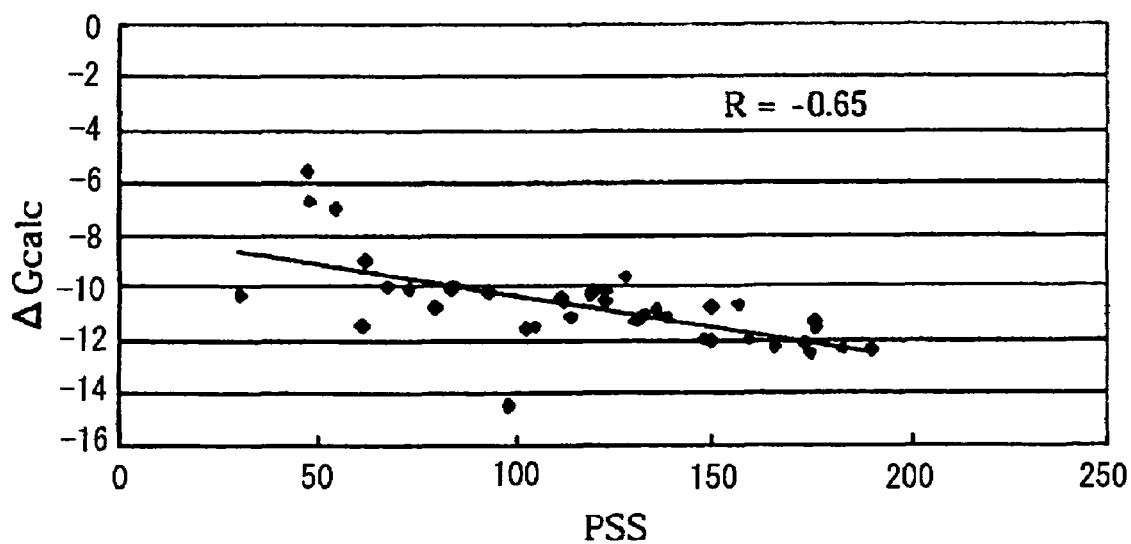
FIG. 16E shows a correlation analysis using a library for evaluation.
Figure 17A:
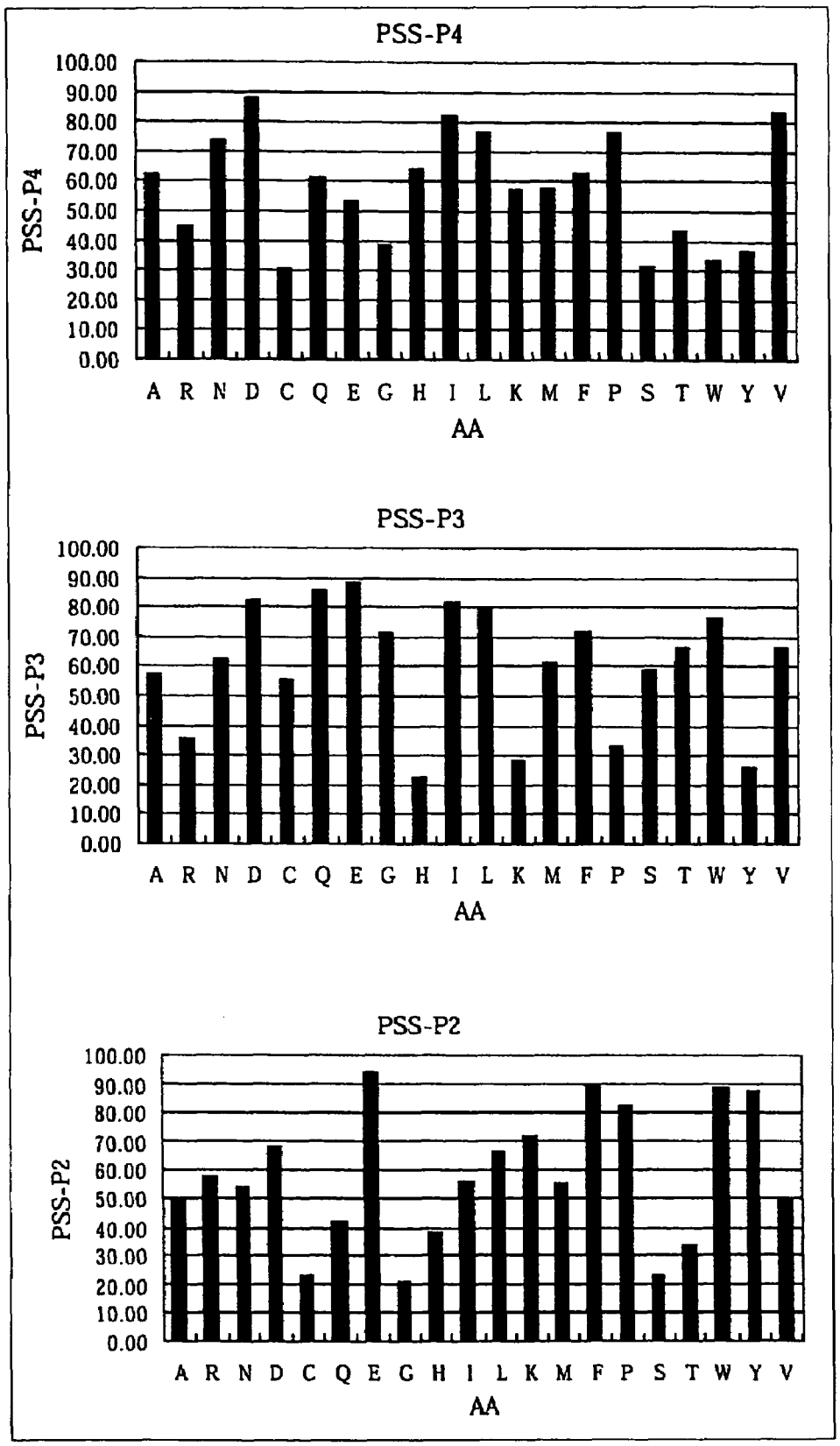
FIG. 17A shows the PSS at each position (P4, P3, P2) of the motif.
Figure 17D:
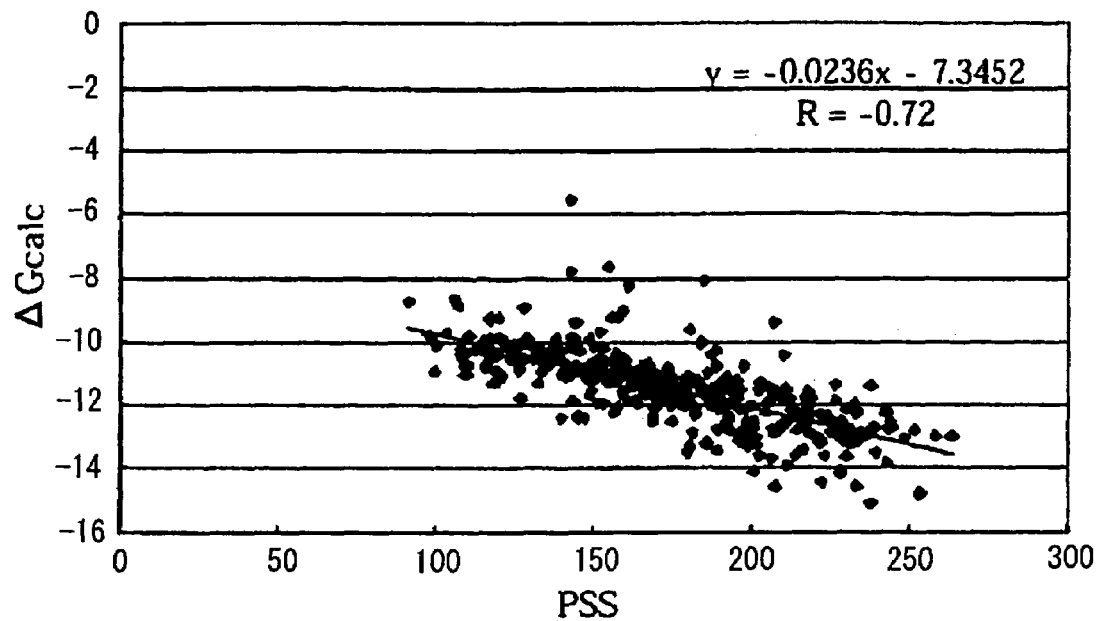
FIG. 17D shows a correlation analysis using a library for analysis.
Figure 17E:
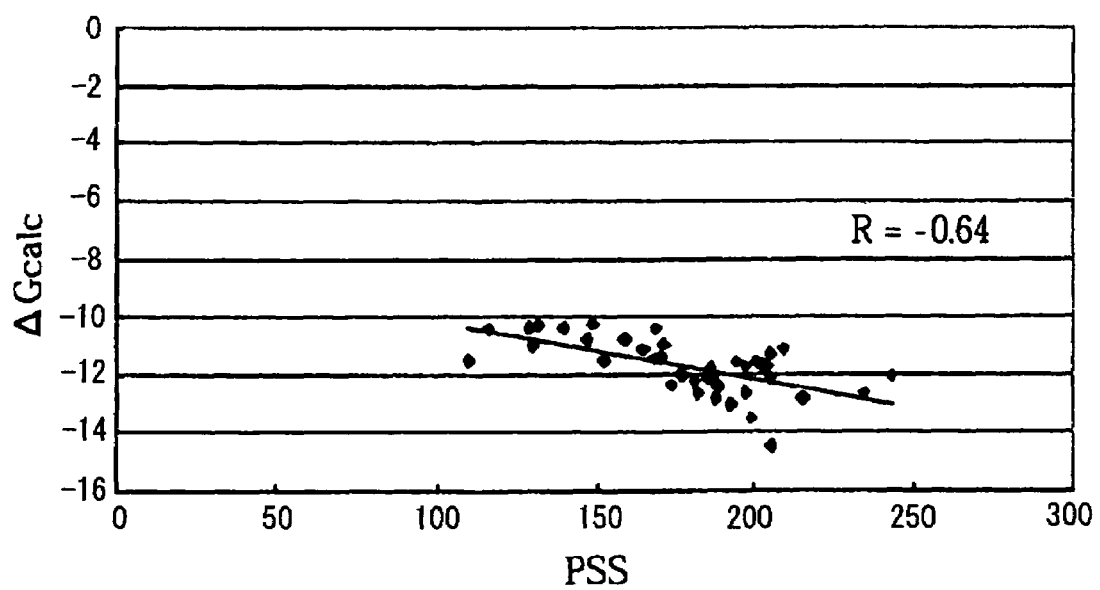
FIG. 17E shows a correlation analysis using a library for evaluation.

Using a cancer-bearing animal experiment system developed by transplanting a human glioma cell (U251-SP) into the brain of a nude mouse, the antitumor effect of (FRP-2)$_4$-MAP in vivo was examined. One week after transplantation of U251-SP into the brain of a nude mouse, (FRP-2)$_4$-MAP, at 2 μg/2 μl, was topically injected to the cancer tissue in the brain. Thirty days later, the animal was autopsied, and a sectional preparation of brain tissue fixed with formalin was prepared by a conventional method and examined under an optical microscope. As a result, in the group treated with the tetramer of the Fas complementary peptide, cancer shrinkage due to cancer cell death as a result of induced apoptosis was observed (FIG. 13). From the series of results shown above, it was confirmed that the program of the present invention was very useful in designing a physiologically active peptide.

Example 3

Evaluation of Existing Caspase Peptide Inhibitors

First, first screening was conducted using caspase-3, -7, -8, and -9. The results are shown in FIGS. 14-17. For all caspases, a correlation coefficient R of −0.71 on average was obtained between PSS and $\Delta G_{calc}$ (FIGS. 14D, 15D, 16D, and 17D)

Subsequently, to evaluate the prediction potential of PSS, a correlation analysis with $\Delta G_{calc}$ (FIGS. 14E, 15E, 16E, and 17E) was conducted using the PSS of 40 peptides contained in a library for evaluation. A value similar to that with the library for analysis, i.e., a correlation coefficient R of −0.66 on average was obtained. Therefore, PSS can be said to be well utilizable for first screening of a vast peptide library.

PSG evaluation of each caspase was conducted using inhibitor peptides with known actual measured Ki values (Table 6) (see, for example, Garcia-Calvo M, et al., J. Biol. Chem., 273, 32608-32613 (1998)) Ac-WEHD-CHO (SEQ ID NO:110), Ac-YVAD-CHO (SEQ ID NO:111), Ac-DEVD-CHO (SEQ ID NO:112), Boc-IETD-CHO (SEQ ID NO:113), Boc-AEVD-CHO (SEQ ID NO:114).

TABLE 6

Inhibitory Potentials of Peptide Inhibitors for Each Caspase

|  | WEHD | YVAD | DEVD | IETD | AEVD |
|---|---|---|---|---|---|
| Caspase-3 | 1960 | 10000 | 0.23 | 195 | 42 |
| Caspase-7 | 10000 | 100000 | 1.6 | 3280 | 425 |
| Caspase-8 | 21.1 | 352 | 0.92 | 1.05 | 1.6 |
| Caspase-9 | 508 | 970 | 60 | 108 | 48 |

The peptide was of the aldehyde type.
Unit of measurement: (nM)

With Ki values of 10,000 nM or more taken as 10,000 nM, each Ki value was converted to $\Delta G$ by [Equation 19] (Table 7).

$$\Delta G = RT \ln(\Delta K_i) \quad \text{[Equation 19]}$$

R: gas constant
T: absolute temperature

Also, the predicted $\Delta G$ values of the five inhibitor peptides were calculated by [Equation 4] using the PSG matrix of each of caspase-3, -7, -8, and -9. A comparison with actual measured values is shown in Table 7.

As a whole, the predicted value were lower than the actual measured values; however, when the correlation coefficient $R_{pep}$ was calculated, its value was as high as 0.93 on average. This shows it possible to predict the relative affinity of inhibitor peptides for caspase. Also, when the correlation coefficient $R_{casp}$ was calculated, its value was 0.71 on average. This shows it possible to predict the specificity of inhibitor peptides for caspase.

Example 4

Designing a Caspase-3 Specific Inhibitor Peptide

Figure 18:
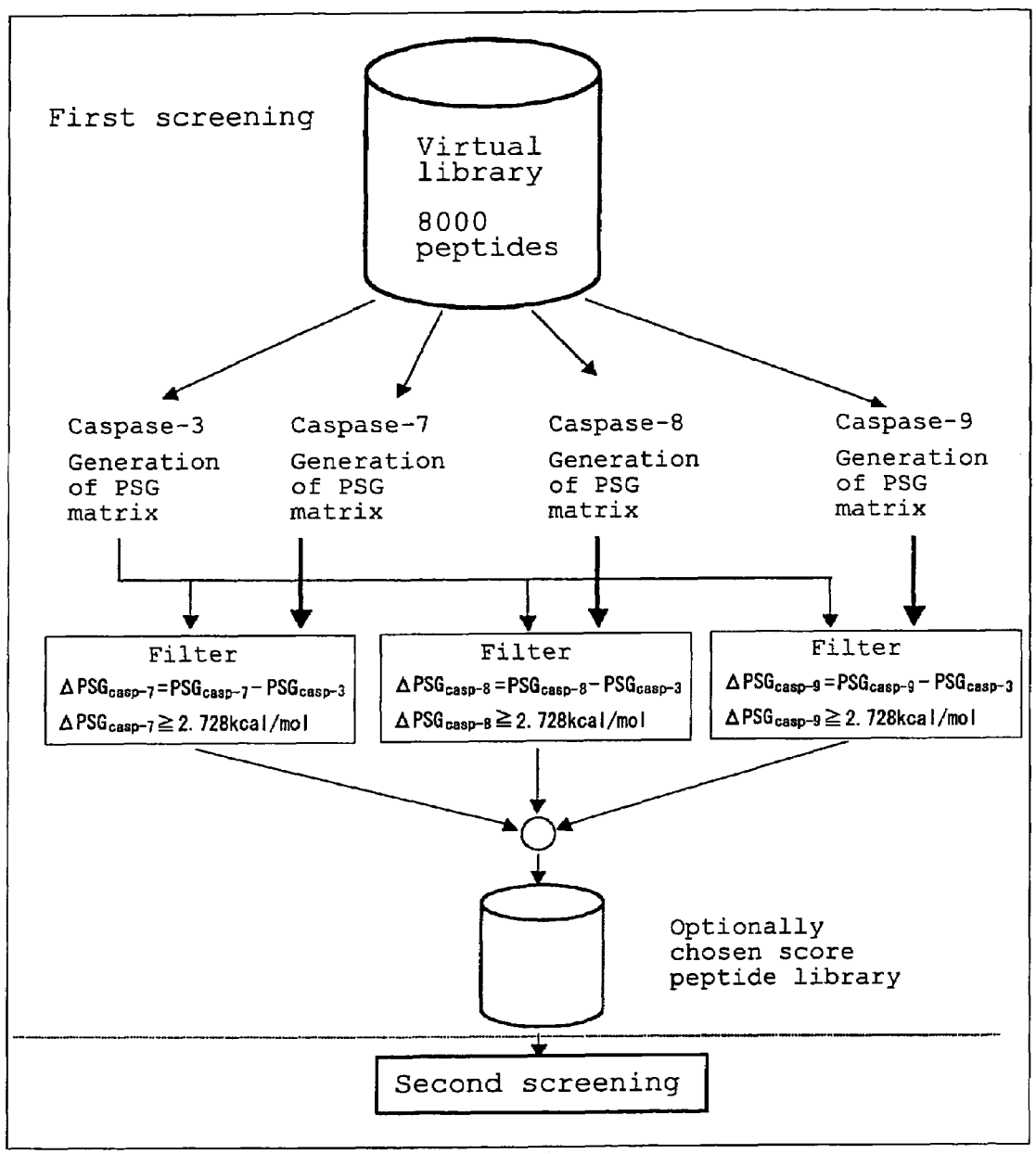
FIG. 18 shows a system configuration in designing a caspase-3 specific inhibitor peptide.

The PSG matrix enables the prediction of affinity and specificity at high speed. The $\Delta G$ of 8000 peptides expressible by P4-P3-P2-D for each caspase can be calculated at high speed using PSG. Designing of a caspase-3 specific inhibitor peptide is described as an example. The system configuration is shown in FIG. 18.

First, one peptide is taken out from the Virtual Library containing 8000 peptides, and its $PSG_{casp-3}$, $PSG_{casp-7}$, $PSG_{casp-8}$, and $PSG_{casp-9}$ are calculated using the PSG matrix of each of caspase-3, -7, -8, and -9. Next, using [Equation 20] below, the differences in PSG between caspase-7, -8, and -9 and caspase-3 are calculated.

$$\Delta PSG_{casp-X} = PSG_{casp-X} - PSG_{casp-3} \quad \text{[Equation 20]}$$

X=7, 8, 9

In this system, a candidate for caspase-3 specific inhibitor peptide was defined as a peptide having a Ki value lower by two digits for all of caspase-7, -8, and -9. A difference of two digits in Ki value is equivalent to a difference of about 2.728 kcal/mol in $\Delta G$. For this reason, [Equation 21] was used as the filter for each caspase.

$$\Delta PSG_{casp-X} \geq 2.728 \text{ kcal/mol} \quad \text{[Equation 21]}$$

X=7, 8, 9

The above procedures are taken for all the 8000 peptides, and only the peptides that passed all filters of the respective caspases will be evaluated by second screening. Finally, the inhibitor peptides selected by second screening are evaluated as designed peptides in vitro and in vivo.

TABLE 7

Evaluation of Caspase Inhibitor Peptides

|  |  | WEHD | YVAD | DEVD | IETD | AEVD | Rpep. |  |
|---|---|---|---|---|---|---|---|---|
| Caspase-3 | Obs. | −7.79 | −6.82 | −13.15 | −9.15 | −10.06 | 0.94 | ave. |
|  | PSG | −9.07 | −8.83 | −14.28 | −11.67 | −13.23 |  | 0.93 |
| Caspase-7 | Obs. | −6.82 | −6.82 | −12.00 | −7.48 | −8.69 | 0.95 |  |
|  | PSG | −9.55 | −9.33 | −13.28 | −11.03 | −11.54 |  |  |
| Caspase-8 | Obs. | −10.47 | −8.80 | −12.33 | −12.25 | −12.00 | 0.92 |  |
|  | PSG | −10.73 | −10.72 | −12.58 | −12.40 | −12.42 |  |  |
| Caspase-9 | Obs. | −8.59 | −8.20 | −9.85 | −9.50 | −9.98 | 0.93 |  |
|  | PSG | −11.13 | −10.97 | −12.71 | −12.17 | −12.10 |  |  |
|  | Rcasp. | 0.67 | 0.92 | 0.64 | 0.90 | 0.44 |  |  |
|  |  |  | ave. | 0.71 |  |  |  |  |

Unit of measurement: (kcal/mol)

For all of caspase-7, -8, and -9, peptide sequences that satisfy [Equation 20] were selected from among the 8000 peptide sequences. The results are shown in Table 8.

TABLE 8

Evaluation of Caspase-3 Specific Inhibitor Peptides

|  |  | Caspase-3 | Caspase-7 | Caspase-8 | Caspase-9 | R |
|---|---|---|---|---|---|---|
| PPVD | PSG | −13.89 | −9.39 | −11.54 | −10.68 | 0.93 |
|  | ΔGcalc | −12.11 | −9.22 | −10.8 | −10.97 |  |
| QPVD | PSG | −13.61 | −9.7 | −11.07 | −10.51 | 0.98 |
|  | ΔGcalc | −12.85 | −10.09 | −11.05 | −11.17 |  |
| TPVD | PSG | −13.29 | −9.11 | −10.29 | −10.34 | 0.97 |
|  | ΔGcalc | −11.86 | −9.56 | −10.62 | −10.13 |  |
| SPVD | PSG | −12.86 | −9.15 | −9.99 | −10.05 | 0.73 |
|  | ΔGcalc | −11.12 | −8.73 | −10.92 | −10.01 |  |

Unit of measurement: (kcal/mol)

In Table 8, the PSG for each caspase and second screening result ΔGcalc are shown. With regard to the three peptides PPVD (SEQ ID NO:115), QPVD (SEQ ID NO:116), and TPVD (SEQ ID NO:117), a high correlation of 0.93 or more was found between PSG and ΔGcalc. On the other hand, for SPVD (SEQ ID NO:118), compared to the above-described three peptides, the correlation was as low as 0.73. The binding free energy of SPVD for caspase-8 was estimated as −9.99 kcal/mol for PSG and −10.92 kcal/mol for ΔGcalc. Also because the ΔGcalc for caspase-3 was evaluated as being high at −11.20 kcal/mol, the difference in ΔGcalc between caspase-3 and -8 was as small as 0.28 kcal/mol. From this result, it is suggested that SPVD may not function as a caspase-3 specific inhibitor peptide.

For PPVD, QPVD, and TPVD as well, ΔGcalc for caspase-3 was estimated as being higher compared to PSG; therefore, although no difference of two digits in Ki value is expected, they are considered to function well as caspase-3 inhibitor peptides.

As a result, the following three candidate peptides are presented as caspase-3 specific inhibitor peptides.

TABLE 9

|  | P4-P3-P2-P1 |  |  |  |
|---|---|---|---|---|
| pep1 | P | P | V | D |
| pep2 | Q | P | V | D |
| pep3 | T | P | V | D |

Example 5

Designing an Apoptosis-Inducing Peptide Using Fas-Binding Region in FasL

To generate a fragmented peptide library, position 144-281, which correspond to the extracellular region of the Fas Ligand, was first applied to the RBD method, and the Fas-binding region was identified at position 151-176. Next, this limited region was extracted, by four residues at a time, from the N-terminus side to obtain a total of 23 fragmented peptides.

For Fas(Receptor) as well, the FasL-binding region was identified at position 99-102 by the RBD method. With this amino acid sequence SKCR at position 99-102 (SEQ ID NO:119) as the target region, peptides capable of interacting therewith were selected by second screening using a fragmented peptide library.

Figure 19:
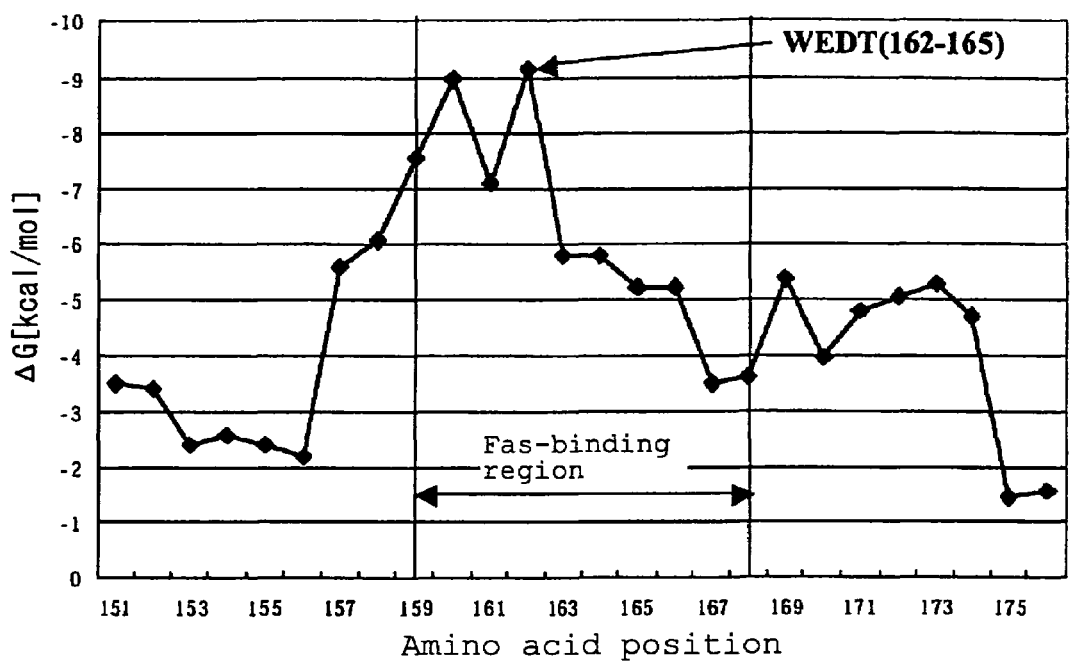
FIG. 19 shows the binding free energy of the Fas Ligand 4-residue peptide for Fas (99-102).

As a result, the amino acid sequence WEDT in the region 162-165 on the Fas Ligand (SEQ ID NO:120) (Ki=0.19 μM) was the sequence of the greatest binding force (FIG. 19). It has been confirmed, also from a Fas-Fas Ligand complex model, that this region is a binding region with FAS.

Next, for third screening, 1-residue amino acid substitution was conducted from the first residue to the fourth residue with WEDT as the lead peptide to introduce variations (Table 10).

TABLE 10

Lead Peptide Variations

|  | W P1 | E P2 | D P3 | T P4 |
|---|---|---|---|---|
| A | 2.73 | 2.67 | 3.48 | 2.19 |
| R | 5.09 | 5.02 | 3.04 | 1.16 |
| N | 2.78 | 1.40 | 3.41 | −0.01 |
| D | 3.42 | 2.41 | 0.00 | 2.09 |
| C | 2.77 | 1.72 | 2.29 | 0.84 |
| Q | 3.14 | 2.88 | 3.74 | 0.34 |
| E | 1.44 | 0.00 | 3.98 | 1.75 |
| G | 2.67 | 0.04 | 0.65 | 2.44 |
| H | 2.16 | 2.71 | 3.68 | 0.41 |
| I | 4.43 | 4.22 | 1.52 | 2.00 |
| L | 3.37 | 1.81 | 2.75 | 3.94 |
| K | 4.08 | 4.12 | 3.80 | 2.61 |
| M | 2.04 | 2.06 | 4.03 | 0.69 |
| F | 4.03 | 2.02 | 1.85 | 0.55 |
| P | 2.61 | 0.85 | 2.57 | 4.04 |
| S | 0.71 | 3.13 | 2.11 | 2.76 |
| T | 2.99 | 0.91 | 0.77 | 0.00 |
| W | 0.00 | 3.44 | −0.52 | 1.20 |
| Y | 4.01 | 3.15 | 4.83 | 2.16 |
| V | 3.00 | 2.72 | 4.10 | 1.50 |

ΔΔG unit (kcal/mol)

As seen in Table 10, the Ki value of WEWT (SEQ ID NO:121) was 0.083 μM. WEWT showed a ΔG value better by 0.52 kcal/mol than WEDT and was predicted as a peptide of greater binding capacity; WEWT was designed as a candidate for physiologically active peptide.

Test Example 4

Induction of Apoptosis with FasL-Like Peptide Tetramer

Figure 20:
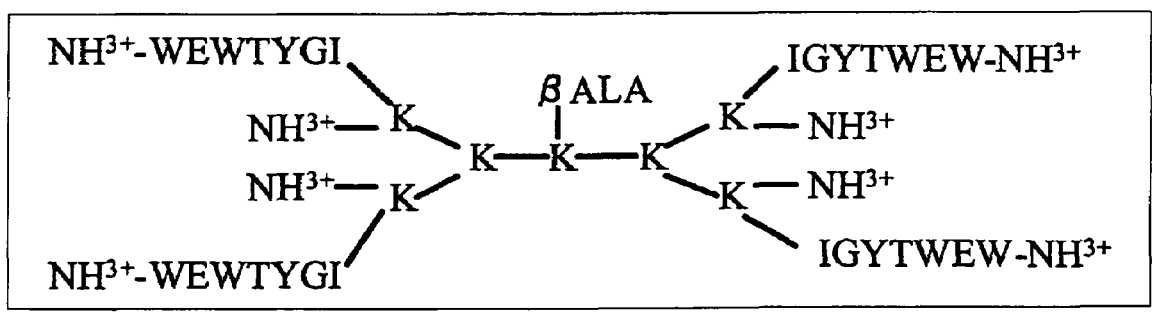
FIG. 20 shows a peptide obtained by binding four WEWT peptides to MAP-8.

Bearing in mind that Fas acts in the form of a trimer, in order to allow the WEWT peptide (SEQ ID NO:121) to fit well to the 37 Å square space formed by the Fas trimer, this peptide was bound to MAP-8 at its 4 branches with the remaining four amino groups protected to generate a candidate peptide (hereinafter abbreviated (FLLP-1)$_4$-MAP$_8$) (FIG. 20). Subsequently, the apoptosis induction potential of (FLLP-1)$_4$-MAP8 was examined using the same method as Test Example 1 above. As a result, (FLLP-1)$_4$-MAP$_8$ induced apoptosis in about 50% of the human ovarian cancer cell line NOS4 at a concentration of about 0.1 μg/ml (Table 11).

TABLE 11

Apoptosis Induction activity of (FLLP-1)$_4$-MAP$_8$

| (FLLP-1)$_4$-MAP$_8$ conc. (μg/ml) | Apoptosis induction Activity (%) |
|---|---|
| 0 | 5 |
| 0.01 | 7 |
| 0.03 | 15 |
| 0.1 | 48 |

TABLE 11-continued

Apoptosis Induction activity of
(FLLP-1)$_4$-MAP$_8$

| (FLLP-1)$_4$-MAP$_8$ conc. (μg/ml) | Apoptosis induction Activity (%) |
|---|---|
| 0.3 | 67 |
| 1 | 78 |

From the above results, it was confirmed that the present technique was extremely useful.

INDUSTRIAL APPLICABILITY

According to the present invention, it is possible to economically, quickly and efficiently design a physiologically active peptide by mathematical calculations without using a cost- and time-consuming biochemical technique or the conventional physiologically active peptide prediction theory, which is poor in reliability and which does not permit narrowing down candidates. Also, according to the present invention, a plurality of evaluation methods can be selected as appropriate for first screening according to the properties of the target protein. Furthermore, according to the present invention, by introducing amino acid substitutions in third screening, and evaluating them, it is possible to obtain a physiologically active peptide having an optimized amino acid sequence.

Free Text for the Sequence Listing

SEQ ID NO:1: amino acid sequence of Fas at position 97-110.

SEQ ID NO:2: amino acid sequence complementary to the amino acid sequence of Fas at position 97-110.

SEQ ID NO:3: amino acid sequence obtained by scrambling the amino acid sequence of SEQ ID NO:2.

SEQ ID NO:4-108: a candidate for an amino acid sequence complementary to the amino acid sequence of caspase-3 at position 206-209.

SEQ ID NO:109: amino acid sequence of caspase-3 at position 206-209.

SEQ ID NO:110: amino acid sequence of caspase inhibitor.
SEQ ID NO:111: amino acid sequence of caspase inhibitor.
SEQ ID NO:112: amino acid sequence of caspase inhibitor.
SEQ ID NO:113: amino acid sequence of caspase inhibitor.
SEQ ID NO:114: amino acid sequence of caspase inhibitor.
SEQ ID NO:115: amino acid sequence of caspase-3-specific inhibitor.
SEQ ID NO:116: amino acid sequence of caspase-3-specific inhibitor.
SEQ ID NO:117: amino acid sequence of caspase-3-specific inhibitor.
SEQ ID NO:118: amino acid sequence of non-caspase-3-specific inhibitor.
SEQ ID NO:119: amino acid sequence of Fas at position 99-102.
SEQ ID NO:120: amino acid sequence of Fas ligand at position 162-165.
SEQ ID NO:121: amino acid sequence of apoptosis-inducing peptide.

The present application is based on Patent Application 2002-258305 filed in Japan (filing date: Sep. 3, 2002), all the teachings of which are understood to be included in the present specification by reference.

---

What is claimed is:

1. A computer-readable recording medium containing a program for designing a physiologically active peptide capable of interacting with a target protein, allowing a computer to execute:
- (a3) a step for exhaustively generating amino acid sequences of constant length, and randomly selecting amino acid sequences from among them for extraction as a library for analysis,
- (b3) a step for calculating an intermolecular energy parameter between each of the amino acid sequences extracted as a library for analysis and a target site of the target protein,
- (c3) a step for generating a score matrix based on amino acid prevalence using the intermolecular energy parameter calculated in step (b3),
- (d3) a step for calculating a score based on amino acid prevalence using the score matrix based on amino acid prevalence generated in step (c3),
- (e3) a step for conducting a correlation analysis between the intermolecular energy parameter calculated in step (b3) and said score to obtain a regression equation,
- (f3) a step for converting the score matrix based on amino acid prevalence generated in step (c3) to a matrix based on an amino acid position-dependent intermolecular energy parameter using said regression equation,
- (g3) a step for calculating an amino acid position-dependent intermolecular energy parameter value from the matrix based on an amino acid position-dependent intermolecular energy parameter converted in step (f3),
- (h3) a step for extracting amino acid not sequences higher than a specified amino acid position-dependent intermolecular energy parameter value,
- (i3) a step for calculating an intermolecular energy parameter with the target site of the target protein, for the amino acid sequences extracted in step (h3),
- (j3) a step for storing the amino acid sequences extracted in step (h3), along with the intermolecular energy parameter calculated in step (i3), in a storage,
- (k3) a step for extracting a specified number of amino acid sequences on the basis of information stored by step (j3), and
- (l3) a step for displaying the amino acid sequences extracted in step (k3) as candidates for a physiologically active peptide.

2. The computer-readable recording medium of claim 1, wherein the program further allows a computer to execute between step (k3) and step (l3):
- (I) a step for generating amino acid sequences with an amino acid variation introduced to the amino acid sequences extracted in step (k3),
- (II) a step for calculating an intermolecular energy parameter between the amino acid sequences generated in step (I) and the target site of the target protein, and
- (III) a step for comparing the intermolecular energy parameter calculated in step (II) with an intermolecular energy parameter between the amino acid sequences extracted in step (k3) and the target site of the target protein as a control, and extracting amino acid sequences having an intermolecular energy parameter that are more stable than the intermolecular energy parameter of the control.

3. The computer-readable recording medium of claim 1, wherein the program further allows a computer to execute the following steps (a1)-(f1):
- (a1) a step for accepting an entry of sequence data on a target amino acid sequence of the target protein,
- (b1) a step for converting said target amino acid sequence to one or more moving average profile waveforms in accordance with one or more specified amino acid indices,
- (c1) a step for generating candidates for an amino acid sequence complementary to the target amino acid sequence of step (a1), and converting them to one or more complementary moving average profile waveforms using the same one or more amino acid indices as those in step (b1),
- (d1) a step for calculating each of complementariness parameters from the same amino acid index between one or more moving average profile waveforms for said target amino acid sequence and one or more complementary moving average profile waveforms of the candidates for a complementary amino acid sequence generated in step (c1),
- (e1) a step for storing the candidates for a complementary amino acid sequence generated in step (c1), along with said complementariness parameter, and
- (f1) a step for extracting a specified number of complementary amino acid sequences on the basis of information stored by step (e1), and/or the following steps (a2)-(b2):
- (a2) a step for identifying the interaction region in a protein that interacts with the target site of the target protein, and
- (b2) a step for extracting amino acid sequences of an optionally chosen length from said interaction region.

4. The computer-readable recording medium of claim 3, wherein said complementariness parameter is the correlation coefficient between a moving average profile waveform for said target amino acid sequence and a complementary moving average profile waveform of a candidate for a complementary amino acid sequence.

5. The computer-readable recording medium of claim 3, wherein said amino acid index is one or more indices selected from among indices based on the degree of hydrophobicity, indices based on an electric property, indices showing the likelihood of taking the α-helix and β-sheet, and indices showing the relative size of side chain volume.

6. The computer-readable recording medium of claim 3, wherein the specified number of complementary amino acid sequences extracted in steps (a1)-(f1) using one or more specified amino acid indices is narrowed down by taking steps (b1)-(f1), in one or more repeats, using one or more other amino acid indices.

7. The computer-readable recording medium of claim 1, wherein the medium is selected from the group consisting of a magnetic tape, magnetic disc, magnetic drum, integrated circuit (IC) card, and optical disc.

8. An apparatus for designing a physiologically active peptide capable of interacting with a target protein, provided with (A3) a first amino acid sequence search portion, (B3) a first intermolecular energy calculation portion, (C3) a score matrix generation portion, (D3) a score calculation portion, (E3) a regression equation generation portion, (F3) a matrix conversion portion, (G3) an amino acid position-dependent energy calculation portion, (H3) a second amino acid sequence search portion, (I3) a second intermolecular energy calculation portion, (J3) an amino acid sequence memory portion, (K3) a third amino acid sequence search portion, and (L3) an amino acid sequence display portion, wherein:

said first amino acid sequence search portion includes (a3) a means of exhaustively generating amino acid sequences of constant length, and randomly selecting amino acid sequences from among them for extraction as a library for analysis, said first intermolecular energy calculation portion includes (b3) a means of calculating an intermolecular energy parameter between each of the amino acid sequences extracted as a library for analysis and a target site of the target antigen, said score matrix generation portion includes (c3) a means of generating a score matrix based on amino acid prevalence using the intermolecular energy parameter calculated by means (b3), said score calculation portion includes (d3) a means of calculating a score based on amino acid prevalence using the score matrix based on amino acid prevalence generated by means (c3), said regression equation generation portion includes (e3) a means of conducting a correlation analysis between the intermolecular energy parameter calculated by means (b3) and said score to obtain a regression equation, said matrix conversion portion includes (f3) a means of converting the score matrix based on amino acid prevalence generated by means (c3) to a matrix based on an amino acid position-dependent intermolecular energy parameter using said regression equation, said amino acid position-dependent energy calculation portion includes (g3) a means of calculating an amino acid position-dependent intermolecular energy parameter value from the matrix based on an amino acid position-dependent intermolecular energy parameter converted by means (f3), said second amino acid sequence search portion includes (h3) a means of extracting amino acid sequences not higher than a specified amino acid position-dependent intermolecular energy parameter value, said second intermolecular energy calculation portion includes (i) a means of calculating an intermolecular energy parameter with the target site of the target protein, for the amino acid sequences extracted by means (h3), said amino acid sequence memory portion includes (ii) a means of storing the amino acid, sequences extracted by means (h3), along with the intermolecular energy parameter calculated by means (i), in a storage, said third amino acid sequence search portion includes (iii) a means of extracting a specified number of amino acid sequences on the basis of information stored by means (ii), and said amino acid sequence display portion includes (iv) a means of displaying the amino acid sequences extracted by means (iii) as candidates for a physiologically active peptide.

9. The apparatus of claim 8, for processing the amino acid sequences extracted by step (f1) and/or (b2) in the second intermolecular energy calculation portion, the amino acid sequence memory portion, the third amino acid sequence search portion, and the amino acid sequence display portion, further provided with the following constitution 1:

(A) a data entry portion, (B) a data editing portion, (C) a complementary amino acid sequence candidate generation portion, (D) a complementariness calculation portion, (E) a complementary amino acid sequence candidate memory portion, and (F) a complementary amino acid sequence search portion, and/or the following constitution 2:

(A2) an interaction region identification portion, and (B2) a first interaction region amino acid sequence search portion, wherein, in said constitution 1:

said data entry portion includes (a1) a means of accepting an entry of sequence data on a target amino acid sequence, said data editing portion includes (b1) a means of converting said target amino acid sequence to one or more moving average profile waveforms in accordance with one or more specified amino acid indices, said complementary amino acid sequence candidate generation portion includes (c1) a means of generating candidates for an amino acid sequence complementary to the target amino acid sequence of means (a1), and converting them to one or more complementary moving average profile waveforms using the same one or more amino acid indices as those for means (b1), said complementariness calculation portion includes (d1) a means of calculating each of complementariness parameters from the same amino acid index between one or more moving average profile waveforms for the target amino acid sequence of means (a1) and one or more complementary moving average profile waveforms of the candidates for complementary amino acid sequence generated by means (c1), said complementary amino acid sequence candidate memory portion includes (e1) a means of storing the candidates for a complementary amino acid sequence generated by means (c1), along with said complementariness parameters, and said complementary amino acid sequence search portion includes (f1) a means of extracting a specified number of complementary amino acid sequences on the basis of information stored by means (e1), and wherein, in said constitution 2:

said interaction region identification portion in said constitution 2 includes (a2) a means of identifying the interaction region in a protein molecule that interacts with the target site of the target protein, and said first amino acid sequence search portion includes (b2) a means of extracting amino acid sequences of an optionally chosen length from said interaction region.

10. A method of designing a physiologically active peptide capable of interacting with a target protein, which method comprises
- (a3) a step for exhaustively generating amino acid sequences of constant length, and randomly selecting amino acid sequences from among them for extraction as a library for analysis, wherein step (a3) is executed by computer,
- (b3) a step for calculating an intermolecular energy parameter between each of the amino acid sequences extracted as a library for analysis and a target site of the target protein, wherein step (b3) is executed by a computer,
- (c3) a step for generating a score matrix based on amino acid prevalence using the intermolecular energy parameter calculated in step (b3), wherein step (c3) is executed by computer,
- (d3) a step for calculating a score based on amino acid prevalence using the score matrix based on amino acid prevalence generated in step (c3), wherein step (d3) is executed by a computer,
- (e3) a step for conducting a correlation analysis between the intermolecular energy parameter calculated in step (b3) and said score to obtain a regression equation, wherein step (e3) is executed by a computer,
- (f3) a step for converting the score matrix based on amino acid prevalence generated in step (c3) to a matrix based on an amino acid position-dependent intermolecular energy parameter using said regression equation, wherein step (f3) is executed by a computer,
- (g3) a step for calculating an amino acid position-dependent intermolecular energy parameter value from the matrix based on an amino acid position-dependent intermolecular energy parameter converted in step (c3), wherein step (g3) is executed by a computer,
- (h3) a step for extracting amino acid sequences not higher than a specified amino acid position-dependent intermolecular energy parameter value, wherein step (h3) is executed by a computer,
- (i3) a step for calculating an intermolecular energy parameter with the target site of the target protein, for the amino acid sequences extracted in step (h3), wherein step (i3) is executed by a computer,
- (j3) a step for storing the amino acid sequences extracted in step (h3), along with the intermolecular energy parameter calculated in step (i3), wherein step (j3) is executed by a computer,
- (k3) a step for extracting a specified number of complementary amino acid sequences on the basis of information stored by step (j3), wherein step (k3) is executed by a computer,
- (I) a step for generating amino acid sequences with an amino acid variation introduced to the amino acid sequences extracted in step (k3), wherein step (I) is executed by a computer,
- (II) a step for calculating an intermolecular energy parameter between the amino acid sequences generated in step (I) and the target site of the target protein, wherein step (II) is executed by a computer, and (III) a step for comparing the intermolecular energy parameter calculated in step (II) with an intermolecular energy parameter between an amino acid sequence extracted in step (k3) and a target site of the target protein as a control, and extracting amino acid sequences having an intermolecular energy parameter that are more stable than the intermolecular energy parameter of the control, wherein step (III) is executed by a computer, and (13) a step for displaying the amino acid sequences extracted by step (III) as candidates for a physiologically active peptide, wherein step (13) is executed by a computer.

11. The method of claim 10, which further comprises extracting, by method 1, complementary amino acid sequences for a target amino acid sequence of the target protein and/or extracting, by method 2, amino acid sequences of an optionally chosen length from the interaction region for the target protein, wherein the method 1 comprises:
- (a1) a step for accepting an entry of sequence data on the target amino acid sequence, wherein step (a1) is executed by a computer,
- (b1) a step for converting the target amino acid sequence to one or more moving average profile waveforms in accordance with one or more specified amino acid indices, wherein step (b1) is executed by a computer,
- (c1) a step for generating candidates for an amino acid sequence complementary to the target amino acid sequence, and converting them to one or more complementary moving average profile waveforms using the same one or more amino acid indices as those in step (b1), wherein step (c1) is executed by a computer,
- (d1) a step for calculating each of complementariness parameters from the same amino acid index between one or more moving average profile waveforms for the target amino acid sequence and one or more complementary moving average profile waveforms of the candidates for a complementary amino acid sequence generated in step (c1), wherein step (d1) is executed by a computer,
- (e1) a step for storing the candidates for a complementary amino acid sequence generated in step (c1), along with said complementariness parameters, in a storage, wherein step (e1) is executed by a computer, and
- (f1) a step for extracting a specified number of complementary amino acid sequences on the basis of information stored by step (e1), wherein step (f1) is executed by a computer, and the method 2 comprises:
- (a2) a step for identifying the interaction region in a protein that interacts with the target site of the target protein, wherein step (a2) is executed by a computer, and
- (b2) a step for extracting amino acid sequences of an optionally chosen length from the interaction region, wherein step (b2) is executed by a computer.

12. The method of claim 11, wherein said complementariness parameter is the correlation coefficient between a moving average profile waveform for said target amino acid sequence and a complementary moving average profile waveform of a candidate for a complementary amino acid sequence.

13. The method of claim 11, wherein said amino acid index is one or more indices selected from among indices based on the degree of hydrophobicity, indices based on an electric property, indices showing the likelihood of taking the α-helix and β-sheet, and indices showing the relative size of side chain volume.

14. The method of claim 11, wherein the specified number of complementary amino acid sequences extracted in steps (a1)-(f1) using one or more specified amino acid indices is narrowed down by taking steps (b1)-(f1), in one or more repeats, using one or more other amino acid indices.

* * * * *

SEQUENCE LISTING

```
<160> NUMBER OF SEQ ID NOS: 121

<210> SEQ ID NO 1
<211> LENGTH: 14
<212> TYPE: PRT
<213> ORGANISM: Homo sapiens

<400> SEQUENCE: 1

Phe Ser Ser Lys Cys Arg Arg Cys Arg Leu Cys Asp Glu Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Amino acid sequence complementary to the amino
      acid sequence of Fas at position 97-110

<400> SEQUENCE: 2

Glu Pro Pro Met Thr Phe Ile Ser Ile His Thr Met Cys His
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Amino acid sequence scrambled for the amino
      acid sequence of SEQ ID No.2
```

-continued

```
<400> SEQUENCE: 3

Thr Phe Ile His Pro Ser Met His Thr Cys Met Pro Glu Ile
1               5                   10

<210> SEQ ID NO 4
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 4

Asn His Phe Lys
1

<210> SEQ ID NO 5
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 5

Glu His Phe Lys
1

<210> SEQ ID NO 6
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 6

Gln Ser Val Lys
1

<210> SEQ ID NO 7
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 7

Gln Ser Leu Lys
1

<210> SEQ ID NO 8
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 8

Asp Ser Val Lys
```

-continued

```
<210> SEQ ID NO 9
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 9

Asp Ser Leu Lys
1

<210> SEQ ID NO 10
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 10

Asp His Ile Lys
1

<210> SEQ ID NO 11
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 11

Glu Thr Trp Lys
1

<210> SEQ ID NO 12
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 12

Asn Thr Trp Lys
1

<210> SEQ ID NO 13
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 13

His His Pro Glu
1

<210> SEQ ID NO 14
```

```
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 14

His His Pro Asn
1

<210> SEQ ID NO 15
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 15

His His Tyr Asp
1

<210> SEQ ID NO 16
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 16

His His Trp Lys
1

<210> SEQ ID NO 17
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 17

Glu His Ala Asp
1

<210> SEQ ID NO 18
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 18

Glu His Gly Gln
1

<210> SEQ ID NO 19
<211> LENGTH: 4
<212> TYPE: PRT
<213> ORGANISM: Artificial Sequence
<220> FEATURE:
```

<223> OTHER INFORMATION: A candidate for amino acid sequence
      complementary to the amino acid sequence of Caspase-3 at position
      206-209

<400> SEQUENCE: 19

Asn His Ala Asp
1

<210> SEQ ID NO 20
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 20

Asn His Met Asp
1

<210> SEQ ID NO 21
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 21

His Ser Met Lys
1

<210> SEQ ID NO 22
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 22

Gln Pro Trp Lys
1

<210> SEQ ID NO 23
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 23

His Ser Ala Lys
1

<210> SEQ ID NO 24
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

-continued

```
<400> SEQUENCE: 24

Gln His Ala Asp
1

<210> SEQ ID NO 25
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 25

Asp Pro Trp Lys
1

<210> SEQ ID NO 26
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 26

Gln His Met Asp
1

<210> SEQ ID NO 27
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 27

Glu Ser Cys Gln
1

<210> SEQ ID NO 28
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 28

Glu His Gly Asn
1

<210> SEQ ID NO 29
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 29

Glu Ser Tyr Gln
1
```

```
<210> SEQ ID NO 30
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 30

Gln Ser Gly Asp
1

<210> SEQ ID NO 31
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 31

Gln His Ala Gln
1

<210> SEQ ID NO 32
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 32

Gln His Met Gln
1

<210> SEQ ID NO 33
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 33

Asn Ser Cys Gln
1

<210> SEQ ID NO 34
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 34

His Glu Phe Lys
1

<210> SEQ ID NO 35
<211> LENGTH: 4
```

-continued

```
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 35

Asn His Gly Asn
1

<210> SEQ ID NO 36
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 36

Glu Pro Met Lys
1

<210> SEQ ID NO 37
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 37

Asn Pro Met Lys
1

<210> SEQ ID NO 38
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 38

Glu Pro Ala Lys
1

<210> SEQ ID NO 39
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 39

His Asn Phe Lys
1

<210> SEQ ID NO 40
<211> LENGTH: 4
<212> TYPE: PRT
<213> ORGANISM: Artificial Sequence
<220> FEATURE:
<223> OTHER INFORMATION: A candidate for amino acid sequence
``` complementary to the amino acid sequence of Caspase-3 at position
206-209

<400> SEQUENCE: 40

His Pro Ile Arg
1

<210> SEQ ID NO 41
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 41

Asp Ser Gly Asp
1

<210> SEQ ID NO 42
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 42

Asp His Met Gln
1

<210> SEQ ID NO 43
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 43

Glu Ser Tyr Asn
1

<210> SEQ ID NO 44
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 44

Asn His Gly Glu
1

<210> SEQ ID NO 45
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 45

Asn Gly Ile Arg
1

<210> SEQ ID NO 46
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 46

Glu Gly Ile Arg
1

<210> SEQ ID NO 47
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 47

Asn Ser Cys Asn
1

<210> SEQ ID NO 48
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 48

Lys Pro Ile Lys
1

<210> SEQ ID NO 49
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 49

Asp Ser Gly Gln
1

<210> SEQ ID NO 50
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 50

Ser Ser Ile Arg
1

```
<210> SEQ ID NO 51
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 51

Asn Ser Tyr Asn
1

<210> SEQ ID NO 52
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 52

His Thr Gly Lys
1

<210> SEQ ID NO 53
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 53

His Asp Ile Lys
1

<210> SEQ ID NO 54
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 54

Asp Ala Ile Arg
1

<210> SEQ ID NO 55
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 55

Glu Thr Tyr Asp
1

<210> SEQ ID NO 56
<211> LENGTH: 4
<212> TYPE: PRT
```

-continued

```
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 56

Asp Met Ile Arg
1

<210> SEQ ID NO 57
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 57

Asn Thr Cys Asp
1

<210> SEQ ID NO 58
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 58

Asn Ser Tyr Glu
1

<210> SEQ ID NO 59
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 59

Gln His Gly Glu
1

<210> SEQ ID NO 60
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 60

Ser His Met Lys
1

<210> SEQ ID NO 61
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
```

```
              206-209

<400> SEQUENCE: 61

Asp His Ala Asn
1

<210> SEQ ID NO 62
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 62

Asp His Met Asn
1

<210> SEQ ID NO 63
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 63

Ser His Ala Lys
1

<210> SEQ ID NO 64
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 64

His Tyr Phe Arg
1

<210> SEQ ID NO 65
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 65

Asn Thr Tyr Asp
1

<210> SEQ ID NO 66
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 66
```

```
Gln Tyr Met Lys
1

<210> SEQ ID NO 67
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 67

His Cys Phe Arg
1

<210> SEQ ID NO 68
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 68

Asp Tyr Met Lys
1

<210> SEQ ID NO 69
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 69

Gln Tyr Ala Lys
1

<210> SEQ ID NO 70
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 70

Asn Thr Tyr Gln
1

<210> SEQ ID NO 71
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 71

Asp Tyr Ala Lys
1
```

```
<210> SEQ ID NO 72
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 72

Asp His Ala Glu
1

<210> SEQ ID NO 73
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 73

Gln Cys Met Lys
1

<210> SEQ ID NO 74
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 74

Gln Ser Cys Asn
1

<210> SEQ ID NO 75
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 75

Asp Cys Met Lys
1

<210> SEQ ID NO 76
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 76

Gln Cys Ala Lys
1

<210> SEQ ID NO 77
<211> LENGTH: 4
<212> TYPE: PRT
<213> ORGANISM: Artificial Sequence
```

```
<220> FEATURE:
<223> OTHER INFORMATION: A candidate for amino acid sequence
      complementary to the amino acid sequence of Caspase-3 at position
      206-209

<400> SEQUENCE: 77

Lys Cys Phe Lys
1

<210> SEQ ID NO 78
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 78

Gln Thr Cys Asp
1

<210> SEQ ID NO 79
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 79

Asp Cys Ala Lys
1

<210> SEQ ID NO 80
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 80

Asn Ala Phe Arg
1

<210> SEQ ID NO 81
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 81

Glu Ala Phe Arg
1

<210> SEQ ID NO 82
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209
```

```
<400> SEQUENCE: 82

Asn Met Phe Arg
1

<210> SEQ ID NO 83
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 83

Glu Met Phe Arg
1

<210> SEQ ID NO 84
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 84

Gln Glu Leu Asp
1

<210> SEQ ID NO 85
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 85

Gln Glu Val Asp
1

<210> SEQ ID NO 86
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 86

Gln Ser Cys Glu
1

<210> SEQ ID NO 87
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 87

Asp Glu Leu Asp
```

```
<210> SEQ ID NO 88
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 88

Asp Glu Val Asp
1

<210> SEQ ID NO 89
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 89

Ser Gln Val Lys
1

<210> SEQ ID NO 90
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 90

Gln Thr Cys Gln
1

<210> SEQ ID NO 91
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 91

Thr Thr Phe Arg
1

<210> SEQ ID NO 92
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 92

Ser Gln Leu Lys
1

<210> SEQ ID NO 93
```

```
-continued

<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 93

Gln Ser Tyr Glu
1

<210> SEQ ID NO 94
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 94

Gln Asn Leu Asp
1

<210> SEQ ID NO 95
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 95

Gln Asn Val Asp
1

<210> SEQ ID NO 96
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 96

Ser Pro Val Arg
1

<210> SEQ ID NO 97
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 97

Asp Asn Leu Asp
1

<210> SEQ ID NO 98
<211> LENGTH: 4
<212> TYPE: PRT
<213> ORGANISM: Artificial Sequence
<220> FEATURE:
```

<223> OTHER INFORMATION: A candidate for amino acid sequence
      complementary to the amino acid sequence of Caspase-3 at position
      206-209

<400> SEQUENCE: 98

Asp Asn Val Asp
1

<210> SEQ ID NO 99
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 99

Glu Tyr Gly Lys
1

<210> SEQ ID NO 100
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 100

His Glu Ala Asp
1

<210> SEQ ID NO 101
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 101

Pro His Ile Arg
1

<210> SEQ ID NO 102
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 102

Gln Thr Tyr Gln
1

<210> SEQ ID NO 103
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

```
<400> SEQUENCE: 103

His Ser Thr Gln
1

<210> SEQ ID NO 104
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 104

Ser Asp Val Lys
1

<210> SEQ ID NO 105
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 105

Ser Asp Leu Lys
1

<210> SEQ ID NO 106
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 106

Asp Glu Leu Gln
1

<210> SEQ ID NO 107
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 107

Asp Glu Val Gln
1

<210> SEQ ID NO 108
<211> LENGTH: 4
<212> TYPE: PRT
<213> ORGANISM: Artificial Sequence
<220> FEATURE:
<223> OTHER INFORMATION: A candidate for amino acid sequence
      complementary to the amino acid sequence of Caspase-3 at position
      206-209

<400> SEQUENCE: 108

Asp Trp Phe Arg
1
```

```
<210> SEQ ID NO 109
<211> LENGTH: 4
<212> TYPE: PRT
<213> ORGANISM: Homo sapiens
<220> FEATURE:
<223> OTHER INFORMATION: An amino acid sequence of Caspase-3 at position
      206-209

<400> SEQUENCE: 109

Trp Arg Asn Ser
1

<210> SEQ ID NO 110
<211> LENGTH: 4
<212> TYPE: PRT
<213> ORGANISM: Artificial Sequence
<220> FEATURE:
<223> OTHER INFORMATION: An amino acid sequence of Caspase inhibitor

<400> SEQUENCE: 110

Trp Glu His Asp
1

<210> SEQ ID NO 111
<211> LENGTH: 4
<212> TYPE: PRT
<213> ORGANISM: Artificial Sequence
<220> FEATURE:
<223> OTHER INFORMATION: An amino acid sequence of Caspase inhibitor

<400> SEQUENCE: 111

Tyr Val Ala Asp
1

<210> SEQ ID NO 112
<211> LENGTH: 4
<212> TYPE: PRT
<213> ORGANISM: Artificial Sequence
<220> FEATURE:
<223> OTHER INFORMATION: An amino acid sequence of Caspase inhibitor

<400> SEQUENCE: 112

Asp Glu Val Asp
1

<210> SEQ ID NO 113
<211> LENGTH: 4
<212> TYPE: PRT
<213> ORGANISM: Artificial Sequence
<220> FEATURE:
<223> OTHER INFORMATION: An amino acid sequence of Caspase inhibitor

<400> SEQUENCE: 113

Ile Glu Thr Asp
1

<210> SEQ ID NO 114
<211> LENGTH: 4
<212> TYPE: PRT
<213> ORGANISM: Artificial Sequence
<220> FEATURE:
<223> OTHER INFORMATION: An amino acid sequence of Caspase inhibitor

<400> SEQUENCE: 114

Ala Glu Val Asp
1
```

<210> SEQ ID NO 115
<211> LENGTH: 4
<212> TYPE: PRT
<213> ORGANISM: Artificial Sequence
<220> FEATURE:
<223> OTHER INFORMATION: An amino acid sequence of Caspase-3 specific
      inhibitor

<400> SEQUENCE: 115

Pro Pro Val Asp
1

<210> SEQ ID NO 116
<211> LENGTH: 4
<212> TYPE: PRT
<213> ORGANISM: Artificial Sequence
<220> FEATURE:
<223> OTHER INFORMATION: An amino acid sequence of Caspase-3 specific
      inhibitor

<400> SEQUENCE: 116

Gln Pro Val Asp
1

<210> SEQ ID NO 117
<211> LENGTH: 4
<212> TYPE: PRT
<213> ORGANISM: Artificial Sequence
<220> FEATURE:
<223> OTHER INFORMATION: An amino acid sequence of Caspase-3 specific
      inhibitor

<400> SEQUENCE: 117

Thr Pro Val Asp
1

<210> SEQ ID NO 118
<211> LENGTH: 4
<212> TYPE: PRT
<213> ORGANISM: Artificial Sequence
<220> FEATURE:
<223> OTHER INFORMATION: An amino acid sequence of Caspase-3
      non-specific inhibitor

<400> SEQUENCE: 118

Ser Pro Val Asp
1

<210> SEQ ID NO 119
<211> LENGTH: 4
<212> TYPE: PRT
<213> ORGANISM: Homo sapiens
<220> FEATURE:
<223> OTHER INFORMATION: An amino acid sequence of Fas at position
      99-102

<400> SEQUENCE: 119

Ser Lys Cys Arg
1

<210> SEQ ID NO 120
<211> LENGTH: 4
<212> TYPE: PRT
<213> ORGANISM: Homo sapiens
<220> FEATURE:
<223> OTHER INFORMATION: An amino acid sequence of Fas Ligand at
      position 162-165

```
<400> SEQUENCE: 120

Trp Glu Asp Thr
1

<210> SEQ ID NO 121
<211> LENGTH: 4
<212> TYPE: PRT
<213> ORGANISM: Artificial Sequence
<220> FEATURE:
<223> OTHER INFORMATION: An amino acid sequence of apoptosis-inducing
      peptide

<400> SEQUENCE: 121

Trp Glu Trp Thr
1
```